US007074929B2

(12) United States Patent
Horvath et al.

(10) Patent No.: US 7,074,929 B2
(45) Date of Patent: Jul. 11, 2006

(54) CERTAIN ALKYLENE DIAMINE-SUBSTITUTED HETEROCYCLES

(75) Inventors: Raymond F. Horvath, Guilford, CT (US); Jennifer Tran, Guilford, CT (US); Stéphane De Lombaert, Madison, CT (US); Kevin J. Hodgetts, Killingworth, CA (US); Philip A. Carpino, Groton, CT (US); David A. Griffith, Old Saybrook, CT (US)

(73) Assignees: Neurogen Corp., Branford, CT (US); Pfizer, Inc., New York, NY (US)

( * ) Notice: Subject to any disclaimer, the term of this patent is extended or adjusted under 35 U.S.C. 154(b) by 0 days.

(21) Appl. No.: 10/705,446

(22) Filed: Nov. 10, 2003

(65) Prior Publication Data
US 2004/0229870 A1    Nov. 18, 2004

Related U.S. Application Data

(62) Division of application No. 10/291,446, filed on Nov. 8, 2002, now Pat. No. 6,696,445, which is a division of application No. 09/676,941, filed on Sep. 29, 2000, now Pat. No. 6,506,762.

(60) Provisional application No. 60/156,870, filed on Sep. 30, 1999.

(51) Int. Cl.
C07D 471/04    (2006.01)
A61K 31/4375   (2006.01)
A61P 15/10     (2006.01)
A61P 3/04      (2006.01)

(52) U.S. Cl. ............... 546/119; 546/117; 546/118; 546/113; 544/276; 544/277; 544/254; 544/281; 544/282; 544/279; 544/262; 544/236; 544/256; 544/80; 544/278; 544/257

(58) Field of Classification Search ............... 546/117, 546/118, 119, 113; 544/276, 277, 254, 281, 544/282, 279, 262, 236, 256, 80, 278, 257; 514/300, 259.4, 259.41, 263.2, 263.21, 263.22, 514/263.23, 263.4, 264.11, 265.1
See application file for complete search history.

(56) References Cited

U.S. PATENT DOCUMENTS

| | | | | |
|---|---|---|---|---|
| 5,273,608 | A | 12/1993 | Nath | 156/301 |
| 5,504,094 | A | 4/1996 | Bruns, Jr. et al. | 514/324 |
| 5,664,057 | A | 9/1997 | Crossman et al. | 704/229 |
| 6,372,743 | B1 | 4/2002 | Darrow et al. | |
| 6,506,762 | B1 | 1/2003 | Horvath et al. | |
| 6,566,367 | B1 | 5/2003 | Bakthavatchalam et al. | |
| 6,696,445 | B1 | 2/2004 | Horvath et al. | |
| 2001/0031474 | A1 | 10/2001 | Kinrade et al. | |
| 2003/0069246 | A1 | 4/2003 | Darrow et al. | |
| 2003/0144290 | A1 | 7/2003 | Blum et al. | |
| 2004/0072847 | A1 | 4/2004 | Bakthavatchalam et al. | |

FOREIGN PATENT DOCUMENTS

| | | |
|---|---|---|
| EP | 0239191 | 9/1987 |
| EP | 0729758 | 9/1996 |
| EP | 0778277 | 6/1997 |
| WO | 9413676 | 6/1994 |
| WO | 9413677 | 6/1994 |
| WO | 9510506 | 4/1995 |
| WO | 9533750 | 12/1995 |
| WO | 9534563 | 12/1995 |
| WO | 9635689 | 11/1996 |
| WO | 9714684 | 4/1997 |
| WO | 9729110 | 8/1997 |
| WO | 9733580 | 9/1997 |
| WO | 9735539 | 10/1997 |
| WO | 9744038 | 11/1997 |
| WO | 9803510 | 1/1998 |
| WO | 9808846 | 3/1998 |
| WO | 9808847 | 3/1998 |
| WO | 9829397 | 7/1998 |
| WO | 9835967 | 8/1998 |
| WO | 9842699 | 10/1998 |
| WO | 9842706 | 10/1998 |
| WO | 9845295 | 10/1998 |
| WO | 9847874 | 10/1998 |
| WO | 9847903 | 10/1998 |
| WO | 9912908 | 3/1999 |
| WO | 9938868 | 8/1999 |
| WO | 9940091 | 8/1999 |
| WO | WO01/23387 | 4/2001 |
| WO | WO01/23389 | 4/2001 |
| WO | WO01/55103 | 8/2001 |
| WO | WO02/48152 | 6/2002 |
| WO | WO03/104255 | 12/2003 |

OTHER PUBLICATIONS

Beck, J.P., et al. "Purin-8-ones As Corticotropin-Releasing Hormone (CRH-R1) Receptor Antagonists" *Bioorganic & Medicinal Chemistry Letters* 9, p. 967-972, (1999).

Arvanitis, A.G., et al. "Non-peptide Corticotropin-Releasing Hormone Antagonists: Syntheses and Structure . . . and -triazines" *J. Med. Chem.*, vol. 42, p. 805-818, (1999).

Hodge, C.N., et al. "Corticotropin-Releasing Hormone Receptor Antagonists: Framework Design and Synthesis . . . Studies" *J. Med. Chem.*, vol. 42, p. 819-832, (1999).

Chorvat, R.J., et al. "Synthesis, Corticotropin-Releasing Factor Receptor Binding Affinity, and Pharmokinetic . . . pyridines" *J. Med. Chem.*, vol. 42, p. 833-848, (1999).

Chen, Y.L., et al. "Synthesis and Oral Efficacy of a 4-(Butylethylamino)pyrrolo[2,3-d]pyrimidine: A Centrally . . . Antagonist" *J. Med. Chem.*, vol. 40, p. 1749-1754, (1997).

Chen, C., et al. "Design and Synthesis of a Series of Non-Peptide High-Affinity Human Corticotropin-Releasing Factor1 Receptor Antagonists" *J. Med. Chem.*, vol. 39, p. 4358-4360, (1996).

Oravcova, J., et al. "Drug-protein Binding Studies New Trends in Analytical and Experimental Methodology" *Journal of Chromatography B*, vol. 677, p. 1-28, (1996).

Chorvat et al. (Journal of Medicinal Chemistry, 1999, vol. 42, No. 5).

Chalmers (TiPS vol. 17, pp. 166-172 Apr. 1996).

Lyrer (Schweiz. Med. Wochenschr., vol. 124, #45, 2005-2012 1994).

Frampton (Drugs and Aging 7 (6) 480-503 (1995).

Primary Examiner—Kahsay Habte
(74) Attorney, Agent, or Firm—Sonia K. Guterman; Lawson & Weitzen, LLP

(57) ABSTRACT

This invention relates to novel compounds, compositions, and methods for the treatment of physiological disorders associated with an excess of neuropeptide Y. The novel compounds encompassed by the present invention are those of the formula II, IV, V, VII–IX and XI

II

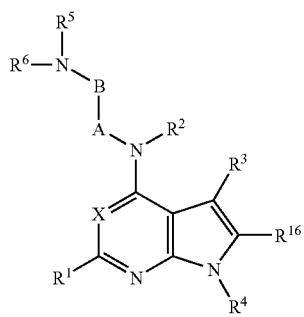

IV

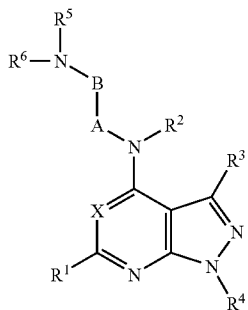

V

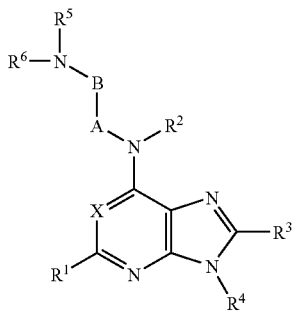

VII

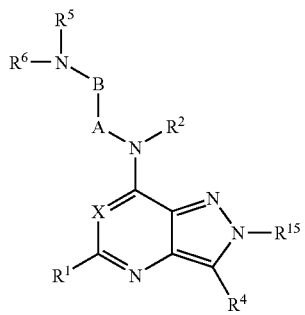

VIII

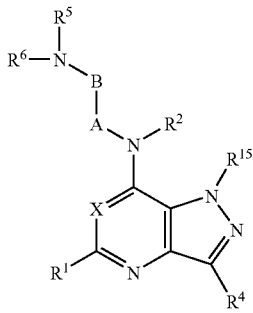

IX

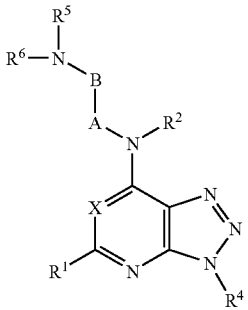

XI

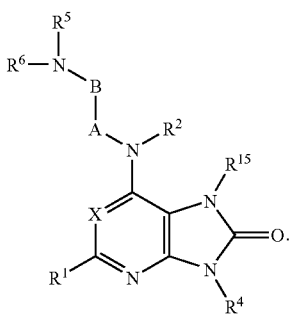

1 Claim, No Drawings

CERTAIN ALKYLENE DIAMINE-SUBSTITUTED HETEROCYCLES

CROSS REFERENCE TO RELATED APPLICATION

This application is a divisional of U.S. patent application Ser. No. 10/291,446, filed on Nov. 8, 2002, now U.S. Pat. No. 6,696,445, issued Feb. 24, 2004, which is a divisional of U.S. patent application Ser. No. 09/676,941, filed on Sep. 29, 2000, now U.S. Pat. No. 6,506,762, issued Jan. 14, 2003. The non-provisional patent application designated above, namely U.S. patent application Ser. No. 09/676,941, filed on Sep. 29, 2000, claims the benefit of U.S. Provisional Patent Application Ser. No. 60/156,870, filed on Sep. 30, 1999, and incorporates the same by reference.

FIELD OF THE INVENTION

This invention relates to certain alkylene diamine-substituted heterocycles which selectively and potently bind mammalian neuropeptide Y (NPY) receptors. This invention also relates to pharmaceutical compositions comprising such compounds. It further relates to the use of such compounds in treating physiological disorders associated with an excess of neuropeptide Y, especially feeding disorders, some psychiatric disorders, and certain cardiovascular diseases.

BACKGROUND OF THE INVENTION

Neuropeptide Y (NPY) is a 36 amino acid peptide first isolated in 1982 and subsequently found to be largely conserved across species. It belongs to a large family of peptides that includes, among others, peptide YY (PYY) and pancreatic peptide (PP). NPY is believed to be the most abundant peptide in the mammalian brain. It is also found in sympathetic neurons, and NPY-containing fibers have been found in peripheral tissues, such as around the arteries in the heart, the respiratory tract, the gastrointestinal tract, and the genitourinary tract. Central injection of NPY elicits a multitude of physiological responses, such as stimulation of feeding, increase in fat storage, elevation of blood sugar and insulin, anxiolytic behaviors, reduction in locomotor activity, hormone release, increase in blood pressure, reduction in body temperature, and catalepsy. In the cardiovascular system, NPY is believed to be involved in the regulation of coronary tone, while in the gastrointestinal tract, PYY is reported to cause inhibition of gastric acid secretion, pancreatic exocrine secretion, and gastrointestinal motility. These effects appear to be selectively mediated by various NPY receptors which currently include the $Y_1$, $Y_2$, $Y_3$, $Y_4$, $Y_5$, and $Y_6$ subtypes, in addition to the hypothetical $Y_{1-like}$ subtype. Selective peptidic agonists and antagonists have been identified for most of the subtypes, but few selective non-peptidic antagonists have been reported. The $Y_1$ and $Y_5$ receptor subtypes appear to be involved in appetite regulation, but their relative contribution to the modulation of food intake and energy expenditure remains unclear. The discovery of non-peptidic antagonists of the $Y_1$ and/or $Y_5$ receptor provides novel therapeutic agents, that are less prone to the shortcomings of the peptide antagonists, namely, for example, poor metabolic stability, low oral bioavailability, and poor brain permeability, for the treatment of obesity and cardiovascular disease.

SUMMARY OF THE INVENTION

The present invention also provides a general method to whereby mono-, bi-, or tricyclic heterocycles may be modified to obtain potent antagonists at the $NPY_1$ receptor.

The present invention provides novel, potent, non-peptidic antagonists of NPY receptors, particularly, the $NPY_1$ receptors, designed from a selection of mono-, bi-, or tri-cyclic heterocyclic cores.

The heterocyclic cores encompassed by the compounds of formula II–XV (shown below) have been previously described. The modifications made to these heterocyclic cores to obtain potent and selective $NPY_1$ antagonists are entirely novel.

Compounds that interact with the $Y_1$ receptor and inhibit the activity of neuropeptide Y at those receptors are useful in treating physiological disorders associated with an excess of neuropeptide Y, including eating disorders, such as, for example, obesity and bulimia, and certain cardiovascular diseases, for example, hypertension.

This invention relates to novel compounds, compositions, and methods for the treatment of physiological disorders associated with an excess of neuropeptide Y. The novel compounds encompassed by the present invention are those of the formula I–XV.

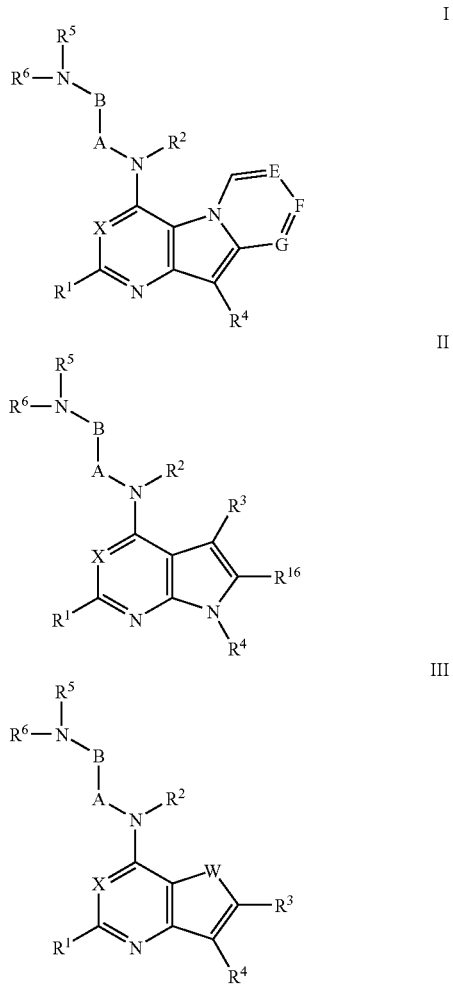

-continued
IV
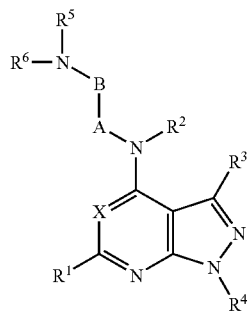
V
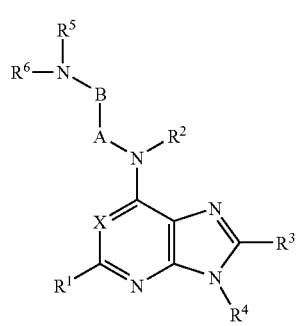
VI
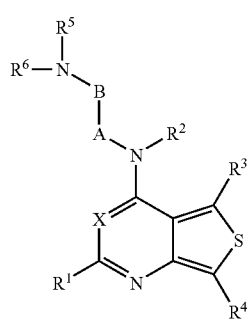
VII
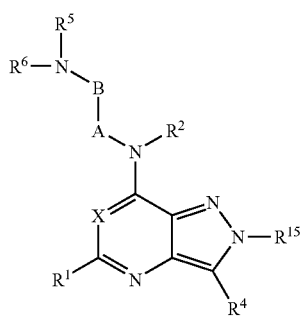
VIII
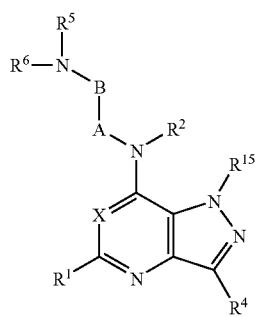
-continued
IX
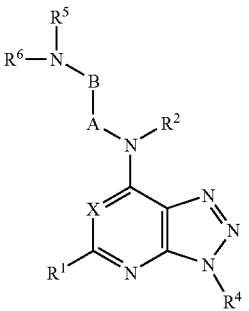
X
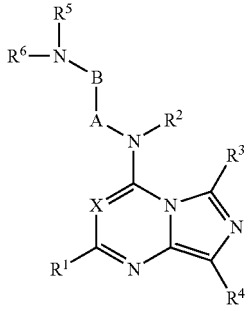
XI
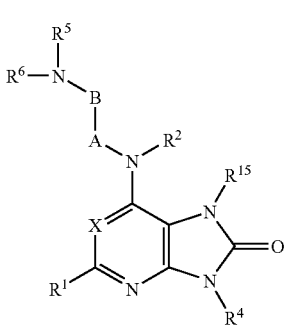
XII
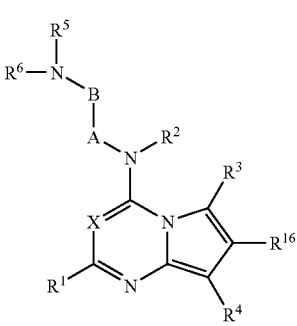
XIII
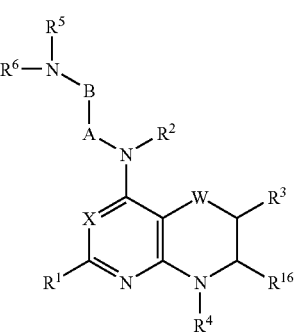

-continued

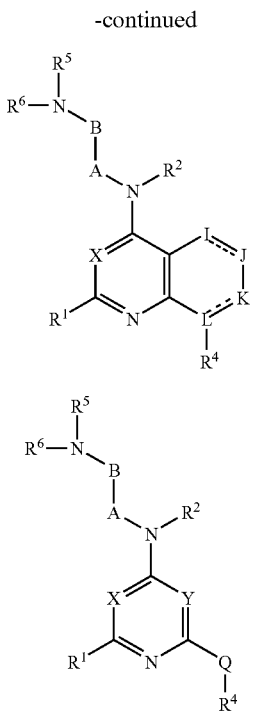

XIV

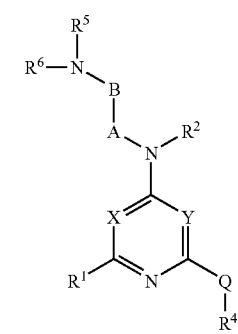

XV wherein
X is N or CR$^{14}$;
W is S, O, or NR$^{15}$;
Y is N or CR$^3$;
E, F, and G are each, independently, CR$^3$ or N;
I and J are each, independently,
  C=O, S, O, CR$^3$R$^{16}$ or NR$^{15}$ when single bonded to both adjacent ring atoms, or
  N, or CR$^3$ when double bonded to an adjacent ring atom;
K is
  N or CR$^3$ when double bonded to L or J, or
  O, S, C=O, CR$^3$R$^{16}$, or NR$^{15}$ when single bonded to both adjacent ring atoms, or
  N or CR$^3$ when double bonded to an adjacent ring atom;
L is
  N or CR$^{16}$ when single bonded to all atoms to which it is attached, or
  C (carbon) when double bonded to K;
The 6- or 7-membered ring that contains I, J, K, and L may contain from 1 to 3 double bonds, from 0 to 2 heteroatoms, and from 0 to 2 C=O groups, wherein the carbon atom of such groups are part of the ring and the oxygen atom is a substituent on the ring;
Q is O or NR$^{15}$;
R$^1$ is selected from H, C$_1$–C$_6$ alkyl, C$_3$–C$_{10}$ cycloalkyl, (C$_3$–C$_{10}$ cycloalkyl) C$_1$–C$_6$ alkyl, C$_2$–C$_6$ alkenyl, C$_2$–C$_6$ alkynyl, cyano, halo, C$_1$–C$_6$ haloalkyl, OR$^7$, C$_1$–C$_6$ alkyl-OR$^7$; C$_1$–C$_6$ cyanoalkyl, NR$^8$R$^9$, C$_1$–C$_6$ alkyl-NR$^8$R$^9$;
R$^2$ is H,
  C$_1$–C$_6$ alkyl which optionally forms a C$_3$–C$_6$ aminocarbocycle or a C$_2$–C$_5$ aminoheterocycle with A or B, each optionally substituted at each occurrence with R$^7$, C$_3$–C$_{10}$ cycloalkyl, or
  (C$_3$–C$_{10}$ cycloalkyl) C$_1$–C$_6$ alkyl;
  or R$^2$ and R$^6$ jointly form with the 2 nitrogen atoms to which they are bound a C$_2$–C$_5$ aminoheterocycle optionally substituted at each occurrence with R$^7$;

A is (CH$_2$)$_m$ where m is 1,2 or 3 and is optionally mono- or di-substituted on each occurrence with C$_1$–C$_6$ alkyl, C$_3$–C$_{10}$ cycloalkyl, (C$_3$–C$_{10}$ cycloalkyl) C$_1$–C$_6$ alkyl, C$_1$–C$_6$ alkenyl, C$_1$–C$_6$ alkynyl, cyano, halo, C$_1$–C$_6$ haloalkyl, OR$^7$, C$_1$–C$_6$ alkyl-OR$^7$; C$_1$–C$_6$ cyanoalkyl, NR$^8$R$^9$, C$_1$–C$_6$ alkyl-NR$^8$R$^9$,
  or A and B jointly form a C$_3$–C$_6$ carbocycle, optionally substituted at each occurrence with R$^7$
  or, as mentioned above, A and R$^2$ jointly form a C$_3$–C$_6$ aminocarbocycle or a C$_2$–C$_5$ aminoheterocycle optionally substituted at each occurrence with R$^7$;
B is (CH$_2$)$_n$ where n is 1,2 or 3 and is optionally mono- or di-substituted on each occurrence with C$_1$–C$_6$ alkyl, C$_3$–C$_{10}$ cycloalkyl, (C$_3$–C$_{10}$ cycloalkyl) C$_1$–C$_6$ alkyl, C$_2$–C$_6$ alkenyl, C$_2$–C$_6$ alkynyl, cyano, halo, C$_1$–C$_6$ haloalkyl, OR$^7$, C$_1$–C$_6$ alkyl-OR$^7$; C$_1$–C$_6$ cyanoalkyl, NR$^8$R$^9$, C$_1$–C$_6$ alkyl-NR$^8$R$^9$,
  or, as mentioned above, B and A jointly form a C$_3$–C$_6$ carbocycle, optionally substituted at each occurrence with R$^7$
  or, as mentioned above, B and R$^2$ jointly form a C$_3$–C$_6$ aminocarbocycle or a C$_2$–C$_5$ aminoheterocycle optionally substituted at each occurrence with R$^7$;
R$^3$ and R$^{16}$ are selected independently at each occurrence from H, C$_1$–C$_6$ alkyl, C$_3$–C$_{10}$ cycloalkyl, (C$_3$–C$_{10}$ cycloalkyl) C$_1$–C$_6$ alkyl, C$_2$–C$_6$ alkenyl, C$_2$–C$_6$ alkynyl, cyano, halogen, C$_1$–C$_6$ haloalkyl, OR$^7$, C$_1$–C$_6$ alkyl-OR$^7$, C$_1$–C$_6$ cyanoalkyl, NR$^8$R$^9$, C$_1$–C$_6$ alkyl-NR$^8$R$^9$;
R$^4$ is selected from aryl or heteroaryl, each optionally substituted with 1 to 5 substituents independently selected at each occurrence from C$_1$–C$_6$ alkyl, C$_3$–C$_{10}$ cycloalkyl, C$_3$–C$_{10}$ cycloalkenyl, (C$_3$–C$_{10}$ cycloalkyl) C$_1$–C$_6$ alkyl, C$_1$–C$_6$ alkenyl, halogen, C$_1$–C$_6$ haloalkyl, trifluromethylsulfonyl, OR$^7$, C$_1$–C$_6$ alkyl-OR$^7$, NR$^8$R$^9$, C$_1$–C$_6$ alkyl-NR$^8$R$^9$, CONR$^8$R$^9$, C$_1$–C$_6$ alkyl-CONR$^8$R$^9$, COOR$^7$, C$_1$–C$_6$ alkyl-COOR$^7$, CN, C$_1$–C$_6$ alkyl-CN, SO$_2$NR$^8$R$^9$, SO$_2$R$^7$, aryl, heteroaryl, heterocycloalkyl, 3-, 4-, or 5-(2-oxo-1,3-oxazolidinyl), with the proviso that at least one of the positions ortho or para to the point of attachment of the aryl or heteroaryl ring to the heterocyclic core is substituted;
R$^5$ is selected from:
  C$_1$–C$_6$ alkyl, (C$_3$–C$_{10}$ cycloalkyl) C$_1$–C$_6$ alkyl, C$_2$–C$_6$ alkenyl, C$_2$–C$_6$ alkynyl, each of which is substituted with 1 to 5 groups independently selected at each occurrence from halo, C$_1$–C$_2$ haloalkyl, OR$^7$, cyano, NR$^8$R$^9$, CONR$^8$R$^9$, COOR$^7$, SO$_2$NR$^8$R$^9$, SO$_2$R$^7$, NR$^{11}$COR$^{12}$, NR$^{11}$SO$_2$R$^7$;
  C$_1$–C$_6$ arylalkyl, C$_1$–C$_6$ heteroarylalkyl, C$_5$–C$_8$ arylcycloalkyl, or C$_5$–C$_8$ heteroarylcycloalkyl, where aryl is phenyl or naphthyl, and heteroaryl is 2-,3-, or 4-pyridyl, 2-, 4- or 5-pyrimidinyl, triazinyl, 1-, 2- or 4-imidazolyl, 2-, 4-, or 5-oxazolyl, isoxazolyl, indolyl, pyrazolyl, quinolyl, isoquinolyl, 2-, 4-, or 5-thiazolyl, benzothiadiazolyl, 1-, 3- or 4-pyrazolyl, 1-, 3- or 4-triazolyl, 2-triazinyl, 2-pyrazinyl, 2-, or 3-furanyl, 2-, or 3-thienyl, 2-, or 3-benzothienyl, or 1-, 2- or 5-tetrazolyl, each of which is optionally substituted with 1 to 5 substituents independently selected at each occurrence from C$_1$–C$_6$ alkyl, C$_3$–C$_{10}$ cycloalkyl, C$_3$–C$_{10}$ cycloalkenyl, (C$_3$–C$_{10}$ cycloalkyl) C$_1$–C$_6$ alkyl, C$_1$–C$_6$ alkenyl, halogen, C$_1$–C$_6$ haloalkyl, trifluromethylsulfonyl, OR$^7$, NR$^8$R$^9$, C$_1$–C$_6$ alkyl-OR$^7$, C$_1$–C$_6$ alkyl-NR$^8$R$^9$, CONR$^8$R$^9$, COOR$^7$, CN, SO$_2$NR$^8$R$^9$, SO$_2$R$^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring;

$C_3$–$C_{10}$ cycloalkyl, ($C_3$–$C_{10}$ cycloalkyl) $C_1$–$C_6$ alkyl, $C_3$–$C_{10}$ cycloalkenyl, $C_2$–$C_6$ alkenyl, $C_2$–$C_6$ alkynyl, each of which is optionally with 1 to 6 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, with the proviso that when two $OR^7$ or $NR^8R^9$ substituents are geminally located on the same carbon $R^7$ is not H and they can form together a $C_2$–$C_4$ ketal, oxazoline, oxazolidine, imidazoline, or imidazolidine heterocycle, $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring;

aryl or heteroaryl, optionally substituted with 1 to 5 substituents independently selected at each occurrence from halogen, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring; or 3- or 4-piperidinyl, 3-pyrrolidinyl, 3- or 4-tetrahydropyranyl; 3-tetrahydrofuranyl, 3- or 4-tetrahydropyranyl, 3-tetrahydrofuranyl, 3- or 4-tetrahydrothiopyranyl, 3- or 4-(1,1-dioxo)tetrahydrothiopyranyl, 1-azabicyclo[4.4.0]decyl, 8-azabicyclo[3.2.1]octanyl, norbornyl, quinuclidinyl, each optionally substituted with 1 to 5 substituents independently selected at each occurrence from $R^7$, $C_1$–$C_6$ alkyl-$OR^7$, $C_1$–$C_6$ alkyl-$NR^8R^9$, $CONR^8R^9$, $COOR_7$;

$R^6$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_1$–$C_6$ arylalkyl, $C_1$–$C_6$ heteroarylalkyl where aryl or heteroaryl are optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^7$, CN, $SO_2NR^8R^9$, $SO_2R^7$, or $R^6$ and $R^2$, as mentioned above, jointly form, with the 2 nitrogen atoms to which they are bound, a $C_2$–$C_5$ aminoheterocycle optionally substituted at each occurrence with $R^7$;

$R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that when $R^7$ is $SO_2R^{13}$, $R^{13}$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that for $SO_2NR^8R^9$, $SO_2R^{13}$, $R^{13}$ cannot be H;

$R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN;

$R^{15}$ is selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_2$–$C_6$ alkyl-$OR^7$, $C_2$–$C_6$ cyanoalkyl, $C_2$–$C_6$ alkyl-$NR^8R^9$;

or a pharmaceutically acceptable salt, hydrate, or prodrug thereof

Preferred compounds of the present invention are those where X is N or CH, $R^1$ is H, $C_1$–$C_6$ alkyl, $C_3$–$C_{10}$ cycloalkyl, or ($C_3$–$C_{10}$ cycloalkyl) $C_1$–$C_6$ alkyl; and $R^6$ is H, $C_1$–$C_6$ alkyl, $C_3$–$C_{10}$ cycloalkyl, or ($C_3$–$C_{10}$ cycloalkyl) $C_1$–$C_6$ alkyl. Additional prefered compounds are those wherein $R^6$ is phenethyl optionally substituted with one or two substituents selected from alkyl and alkoxy, tetrahydropyranyl and piperidinyl optionally substituted by a heterocycle. Other preferred compounds are those wherein $R^4$ is phenyl, optionally substituted in one, two or three positions by alkyl, alkoxy or halogen.

This invention also encompasses, in additional embodiments, the novel compounds of formula I–XV, and the salts and solvates thereof, as well as pharmaceutical formulations comprising a compound of formula I–XV, or a pharmaceutically acceptable salt or solvate thereof, in combination with one or more pharmaceutically acceptable carriers, excipients, or diluents thereof.

This invention also encompasses methods to treat physiological disorders associated with an excess of neuropeptide Y, such as eating and cardiovascular disorders, which method comprises administering to a mammal in need of said treatment an effective amount of a compound of the formula I–XV.

This invention also encompasses methods of selectively inhibiting binding of $NPY_1$ receptors, which comprises contacting a compound of formula I–XV with neuronal cells, wherein the compound is present in an amount effective to produce a concentration sufficient to inhibit binding of $NPY_1$ receptors in vitro.

As such, the present invention also provides a method to convert heterocyclic cores of formula Ia to XVa where X, E, F, G, W, I, J, K, L, Q, $R^1$, $R^3$, $R^4$, $R^{15}$ and $R^{16}$ are defined above, into compounds that potently and selectively interact with $NPY_1$ receptors by substituting the n-position of heterocycles of formula Ia–XVIa with a diamine group of formula $N[R^2]$-A-B—$N[R^6]$—$R^5$ where $R^2$, A, B, $R^6$, and $R^5$ are defined above.

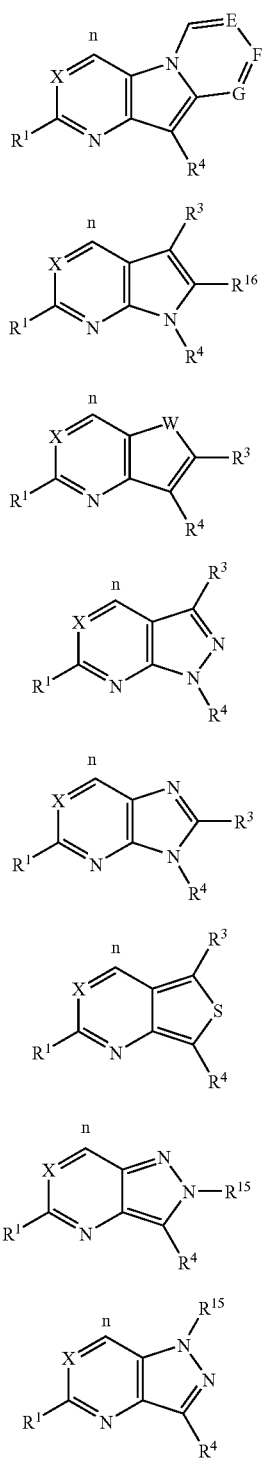

Ia

IIa

IIIa

IVa

Va

VIa

VIIa

VIIIa

-continued

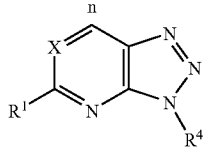

IXa

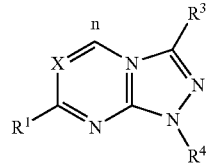

Xa

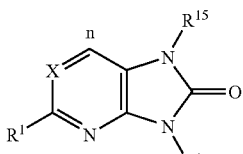

XIa

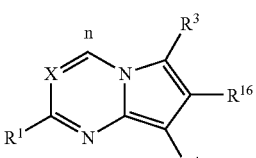

XIIa

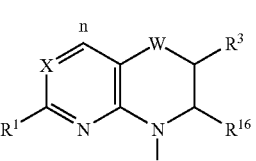

XIIIa

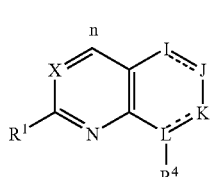

XIVa

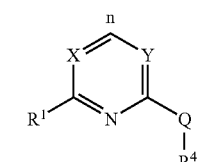

XVa

DETAILED DESCRIPTION OF THE INVENTION

This invention relates to certain alkylene diamine-substituted heterocycles which selectively and potently bind mammalian neuropeptide Y (NPY) receptors., those of formula I–XV, which are novel and useful neuropeptide Y receptor antagonists.

In the present description, the compounds of formula I–XV may be generically described under formula A, where $R^1$, $R^2$, $R^4$, $R^5$, $R^6$, X, Y, A, and B are defined above.

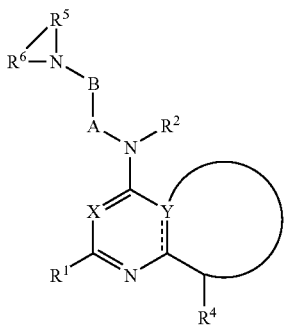

In certain situations, the compounds of formula I–XV may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by formula I–XV, include, but are not limited to the compounds in Examples 1–56 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)$n-COOH where n is 0–4, and the like. Those skilled in the art will recognize a wide variety of non-toxic pharmaceutically acceptable addition salts.

The present invention also encompasses the acylated prodrugs of the compounds of formula I–XV. "Prodrugs" are considered to be any covalently bonded carriers which release the active parent drug of formula I–XV in vivo when such prodrug is administered to a mammalian subject. Prodrugs of the compounds of the invention are prepared by modifying functional groups present in the compounds in such a way that the modifications are cleaved, either in routine manipulation or in vivo to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include,.but are not limited to, acetate, formate, and benzoate derivatives of alcohol and amine functional groups in the compounds of formula I–XV; and the like. Those skilled in the art will recognize various synthetic methodologies which may be employed to prepare non-toxic pharmaceutically acceptable addition salts and acylated prodrugs of the compounds encompassed by formula I–XV.

Where a compound exists in various tautomeric forms, the invention is not limited to any one of the specific tautomers. The invention includes all tautomeric forms of a compound.

By "heteroatom" in the present invention is meant oxygen or sulfur, or a nitrogen atom optionally substituted by $C_1$–$C_6$ lower alkyl, $C_1$–$C_6$ arylalkyl, $C_1$–$C_{10}$ cycloalkyl, ($C_3$–$C_{10}$ cycloalkyl) $C_1$–$C_6$ alkyl, $C_2$–$C_8$ alkanoyl, $C_1$–$C_6$ sulfonyl.

By "alkyl", "lower alkyl", or "$C_1$–$C_6$ alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "cycloalkyl", or "$C_3$–$C_{10}$ cycloalkyl" in the present invention is meant alkyl groups having 3–10 carbon atoms forming a mono-, bi-, or polycyclic ring system, such as, for example, cyclopropyl, cyclobutyl, cyclopentyl, cyclohexyl, cycloheptyl, norbornyl, and, the like.

By "(cycloalkyl)alkyl", "lower (cycloalkyl)alkyl" or ($C_3$–$C_{10}$ cycloalkyl) $C_1$–$C_6$ alkyl in the present invention is meant a straight or branched alkyl substituent formed of 1 to 6 carbon atoms attached to a mono-, bi, or polycyclic ring system having 3–10 carbon atoms, such as, for example, cyclopropylmethyl, cyclobutylmethyl, cyclopentylmethyl, cyclohexylmethyl, cycloheptylmethyl, and the like.

The term "$C_2$–$C_6$ alkenyl" in the present invention means hydrocarbon chains having 2 to 6 carbons in a straight or branched arrangement and containing one or more unsaturated carbon-carbon double bonds which may occur in any stable point along the chain, such as, for example, ethenyl, allyl, isopropenyl, and the like.

By "cycloalkenyl" or "$C_3$–$C_{10}$ cycloalkenyl" in the present invention is meant alkyl groups having 3–10 carbon atoms forming a mono-, bi, or polycyclic ring system having 3–10 carbon atoms and containing one or more carbon-carbon double bonds which may occur in any stable point in the ring, such as, for example, cyclopentenyl, cyclohexenyl, or cycloheptenyl.

The term "$C_2$–$C_6$ alkynyl" in the present invention means hydrocarbon chains having 2 to 6 carbons in a straight or branched arrangement and containing one or more unsaturated carbon-carbon triple bonds which may occur in any stable point along the chain, such as, for example, ethynyl, propargyl, and the like.

The term "aryl" in the present invention means a monocyclic or bicyclic aromatic group having preferably 6 to 10 carbon atoms, such as, for example, phenyl or naphthyl.

The term "heteroaryl" in the present invention means an aryl group in which one or more of the ring(s) carbon atoms have been replaced with a heteroatom. Such groups preferably have 4 to 10 carbon atoms and 1 to 4 heteroatoms, such as, for example, pyridyl, pyrimidinyl, triazinyl, imidazolyl, oxazolyl, isoxazolyl, indolyl, pyrrolyl, pyrazolyl, quinolinyl, isoquinolinyl, thiazolyl, benzothiadiazolyl, triazolyl, triazinyl, pyrazinyl, furanyl, thienyl, benzothienyl, benzofuranyl, tetrazolyl.

The term "heterocyclyl", "heterocycle" or "heterocycloalkyl" in the present invention means a saturated or partially saturated heteroaryl group.

By "$C_1$–$C_6$ arylalkyl" or "$C_1$–$C_6$ heteroarylalkyl" in the present invention is meant a branched or straight-chain alkyl group having 1–6 carbon atoms and substituted on one of the carbon atoms by an optionally substituted aryl or heteroaryl ring, such as, for example, benzyl, phenethyl, methylpyridyl, ethylpyridyl, and the like.

By "$C_5$–$C_8$ arylcycloalkyl" in the present invention is meant cycloalkyl groups having 5–8 carbon atoms and fused to an aryl group, such as, for example, 1,2,3,4 tetrahydronaphthalenyl, 2,3-dihydrobenzothienyl, or 2,3-dihydobenzofuranyl.

By "$C_5$–$C_8$ heteroarylcycloalkyl" in the present invention is meant cycloalkyl groups having 5–8 carbon atoms fused to a heteroaryl group, such as, for example, 1,2,3,4 tetrahydroquinolyl, 2,3-dihydrobenzothienyl, 2,3-dihydobenzofuranyl, or indolinyl.

By "alkoxy", "$C_1$–$C_6$ alkoxy", or "$C_1$–$C_6$ alkyloxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "cycloalkoxy", "$C_3$–$C_{10}$ cycloalkoxy", or "$C_3$–$C_{10}$ cycloalkyloxy" in the present invention is meant a group formed by an oxygen atom attached to a mono-, bi, or polycyclic ring system having 3–10 carbon atoms, such as, for example, cyclopropoxy, cyclobutoxy, cyclopentoxy, cyclohexoxy, or cycloheptoxy.

By "(cycloalkyl)alkyloxy", "($C_3$–$C_{10}$ cycloalkyl) $C_1$–$C_6$ alkoxy", or "($C_3$–$C_{10}$ cycloalkyl) $C_1$–$C_6$ alkyloxy" in the present invention is meant a group formed by an oxygen atom attached to a 1–6 carbon chain linked to a mono-, bi, or polycyclic ring system having 3–10 carbon atoms, such as, for example, cyclopropylmethyloxy, cyclobutylmethyloxy, cyclopentylmethyloxy, cyclohexylmethyloxy, cycloheptylmethyloxy, and the like.

By "$C_3$–$C_6$ aminocarbocycle" is meant a cyclic amino group formed by a nitrogen contained in a ring having 3 to 6 carbon atoms, such as, for example, azetidino, pyrrolidino, piperidino, perhydroazepino.

By "$C_2$–$C_5$ aminoheterocycle" is meant a cyclic amino group formed by a nitrogen contained in a ring having 2 to 5 carbon atoms and one other heteroatom, such as, for example, morpholino, thiomorpholino, piperazino.

By the terms "halo" or "halogen" in the present invention is meant fluoro, chloro, bromo, and iodo.

"Haloalkyl" is intended to include both branched and straight-chain alkyl having the specified number of carbon atoms substituted with 1 or more halogens.

The term "$C_2$–$C_8$ alkanoyl" means an acyl group with 2 to 8 carbon atoms in a linear, branched, or $C_3$–$C_{10}$ cycloalkyl arrangement, optionally substituted with 1 to 5 substituents independently selected at each occurrence from halogen, trifluoromethyl, $OR^7$, $NR^8R^9$, $CONR^8R^9$, $COOR^7$, or CN.

The term "$C_1$–$C_6$ alkyl sulfonyl" means an alkylsulfonyl group containing 1 to 6 carbon atoms in a linear, branched, or $C_3$–$C_7$ cycloalkyl arrangement.

The term "substituted" means that one or more hydrogen on the designated atom is replaced by the specified group, provided that the valence on the designated atom is not exceeded, and that a chemically stable compound results from the substitution.

A stable compound is defined herein as one that can be isolated, characterized, and tested for biological activity.

The term "oxo" (i.e. =O) indicates that two geminal hydrogen atoms are replaced by a double-bond oxygen group.

By "heterocyclic core" in the present invention is meant one of the following structures of formula Ia to XVa, where X, E, F, G, W, I, J, K, L, Q, $R_1$, $R^3$, $R^4$, $R^{15}$ and $R^{16}$ are defined above.

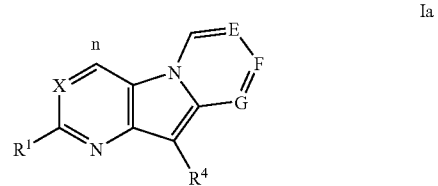

Ia

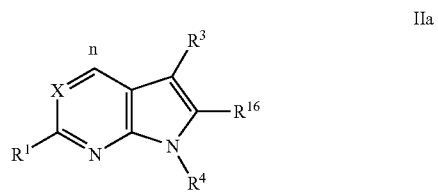

IIa

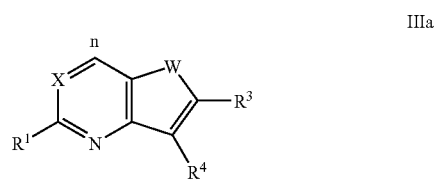

IIIa

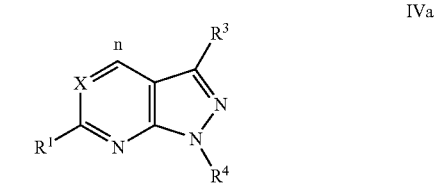

IVa

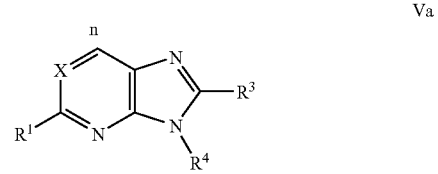

Va

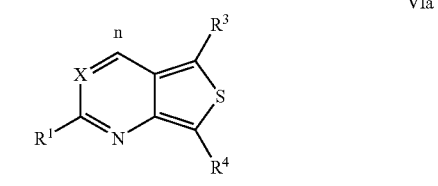

VIa

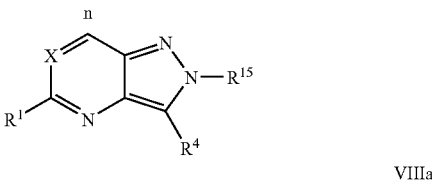

VIIa

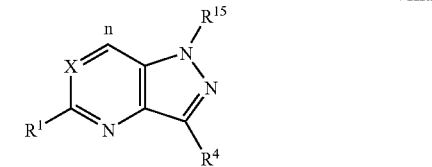

VIIIa

-continued

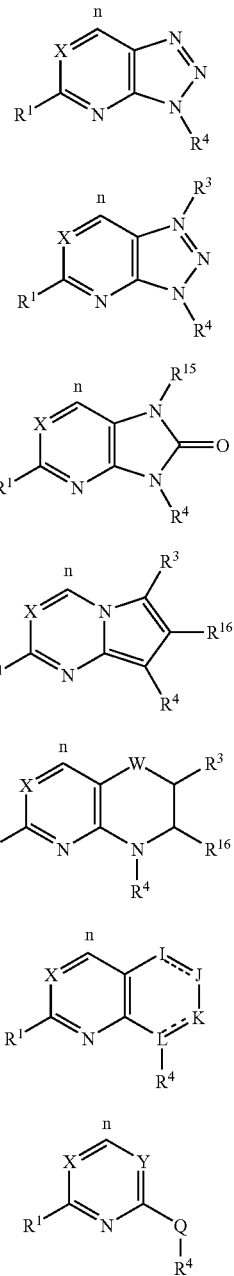

In the present invention, some of the groups specifically mentioned above are defined as follows

| | |
|---|---|
| 2-one-1,3-oxazolidinyl is | 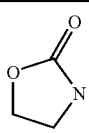 |
| 1-aza-bicyclo[4.4.0]decyl is | 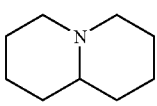 |
| 8-azabicyclo[3.2.1]octanyl is |  |
| (1,1-dioxo)tetrahydrothiopyranyl is | 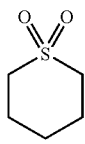 |
| norbornyl is |  |
| quinuclidinyl is | 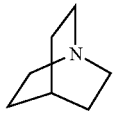 |

Unless specified, the point of attachment may occur in any stable point along the above-mentioned rings.

In the present invention, the term "potent" in the context of NPY1 receptor antagonists qualifies a binding affinity with a Ki of less than 10 micromolar, preferably less than 1 micromolar, and more preferably less than 100 nanomolar in the human NPY1 binding assay.

In the present invention, the term "selective" in the context of NPY1 receptor antagonists qualifies a binding affinity with a Ki in the human $NPY_1$ binding assay that is 10-fold, preferably 100-fold, and more preferably 1000-fold, less than the Ki of the same compound measured in another receptor binding assay, in particular the $NPY_5$ and $CRF_1$ receptor binding assays. Binding assays for the $NPY_5$ and $CRF_1$ receptors have been described, for example, in *J. Clin. Invest.*, 102, 2136 (1998) and in *Endocrinology* 116, 1653 (1985), respectively.

As the compounds of formula I–XV are antagonists of the Y1 receptor, they are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of formula I–XV or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present locally. These physiological disorders may include: disorders or diseases pertaining to the heart, blood vessels or the renal system, such as vasospasm, heart failure, shock, cardiac hypertrophy increased blood pressure, angina, myocardial infarction, sudden cardiac death, arrhythmia, peripheral vascular disease,-and abnormal renal conditions such as impaired flow of fluid, abnormal mass transport, or renal failure; conditions related to increased sympathetic nerve activity for example, during or after coronary artery surgery, and operations and surgery in the gastrointestinal tract; cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia; conditions related to pain or nociception; diseases related to abnormal gastrointestinal motility and secretion, such as different forms of ileus, urinary incontinence, and Crohn's disease; abnormal drink and food intake disorders, such as obesity, anorexia, bulimia, and metabolic disorders; diseases related to sexual dysfunction and reproductive disorders; conditions or disorders associated with inflammation; respiratory diseases, such as asthma and conditions related to asthma and bronchoconstriction; and diseases related to abnormal hormone release, such as leutinizing hormone, growth hormone, insulin, and prolactin. See U.S. Pat. No. 5,504,094.

Pharmaceutical Preparations

The compounds of general Formula I–XV may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I–XV and a pharmaceutically acceptable carrier. One or more compounds of general Formula I–XV may be present in association with one or more non-toxic pharmaceutically acceptable carriers and/or diluents and/or adjuvants and if desired other active ingredients. The pharmaceutical compositions containing compounds of general Formula I–XV may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachid oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachid oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotopic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I–XV may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I–XV may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 50 mg per kilogram of body weight per day are useful in the treatment of the above-indicated conditions (about 0.5 mg to about 3 g per patient per day), although in some circumstances higher amoounts, fo example upto 140 mg/kg/day may be appropriate. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most eating disorders, a dosage regimen of 4 times daily or less is preferred. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (*Journal of Chromatography B* 1996, 677, 1–27).

Compound half-life is inversely proportional to the frequency of dosage of a compound. In vitro half-lives of compounds may be predicted from assays of microsomal half-life as described by Kuhnz and Gieschen (*Drug Metabolism and Disposition* 1998, 26, 1120–1127).

As discussed above, preferred compounds of the invention exhibit good activity in standard in vitro NPY receptor binding assays, specifically the assay as specified in Example 261, which follows. References herein to "standard in vitro receptor binding assay" are intended to refer to that protocol as defined in Example 261 which follows. Generally preferred compounds of the invention exhibit a $K_i$ of about 1 micromolar or less, still more preferably and $K_i$ of about 100 nanomolar or less even more preferably an $K_i$ of about 10 nanomolar or less or even 1 nanomolar or less in such a defined standard in vitro NPY receptor binding assay as exemplified by Example 261 which follows.

In appropriate case, the compounds of the invention may be employed in combination with other active agents. The invention therefore also provides pharmaceutical combination compositions comprising a therapeutically effective amount of a composition comprising: (a) first compound, said first compound being a compound as described above a prodrug thereof, or a pharmaceutically acceptable salt of said compound or of said prodrug; and (b) a second compound, said second compound being a $\beta_3$ agonist, a thyromimetic, an eating behavior modifying agent or a NPY antagonist; and a pharmaceutical carrier, vehicle, diluent. To this end therefore the invention also provides a kit comprising: (a) first compound, said first compound being a compound as described above, a prodrug thereof, or a pharmaceutically acceptable salt of said compound or of said prodrug; (b) a second compound, said second compound being a $\beta_3$ agonist, a thyromimetic, an eating behavior modifying agent or a NPY antagonist; and a pharmaceutical carrier, vehicle, diluent; and (c) means for containing said first and second unit dosage forms wherein the amounts of the first and second compounds result in a therapeutic effect.

Preparation of Alkylene Diamnine-Substituted Heterocycles of Formula I–XV

The preparation of these heterocyclic cores, identified in formula II–XV, can be carried out according to the methods described in the following references and those cited therein:

Formula II: WO 9413676, WO 9534563, WO 9845295, EP 729758, *J. Med. Chem.*, 40(11), 1749–1754 (1997), *Bioorg. Med. Chem. Lett.*, 9(7), 967–972 (1999), *J. Med. Chem.*, 42(5), 819–832 (1999); *J. Med. Chem.* 42(5), 833–848 (1999);

Formula III: WO 9635689, WO 9729110, WO 9808847, WO 9847903, WO 9940091, U.S. Pat. No. 5,664,057;

Formula IV: WO 9413677, WO 9534563, EP 0729758;

Formula V: WO 9533750, *J. Med. Chem.* 42(5), 833–848 (1999); *Bioorg. Med. Chem. Lett.*, 9(7), 967–972 (1999);

Formula VI: WO 9808847, WO 9829397;

Formula VII: EP 239191, U.S. Pat. No. 5,273,608;

Formula VIII: U.S. Pat. No. 5,273,608;

Formula IX: WO 9510506, WO 9735539, WO 9808847, WO 9842706, *J. Med. Chem.* 42(5), 833–848 (1999);

Formula X: WO 9808847, WO 9835967;

Formula XI: WO 9533750, *Bioorg. Med. Chem. Lett.*, 9(7), 967–972 (1999);

Formula XII: WO 9808847, WO 9835967;

Formula XIII: WO 9744038;

Formula XIV: WO 9808846; WO 9829397, WO 9835967, WO 9847874, WO 9912908;

Formula XV: WO 9510506, WO 9533750, WO 9714684, WO 9735580, WO 9842699, EP 778277, *J. Med. Chem.* 39(22), 4358–4360 (1996), *J. Med. Chem.* 42(5), 805–818 (1999), *J. Med. Chem.* 42(5), 833–848 (1999);

An illustration of preparation methods of compounds of the present invention is given in the Schemes below. In particular displacement of a leaving group Z, as in formula 10 (scheme 1) by the appropriate substituted amine or appropriate substitution of an heterocyclic amino group, as in formula 21 (scheme 7), provides general methods to convert the heterocyclic cores of the present invention into compounds that potently interact with the $NPY_1$ receptor. Such transformations may require several consecutive chemical steps. Those having skill in the art will recognize that the starting materials may be varied and additional steps employed to produce compounds encompassed by the present invention. The disclosures of all articles and references mentioned in this application, including patents, are incorporated herein by reference.

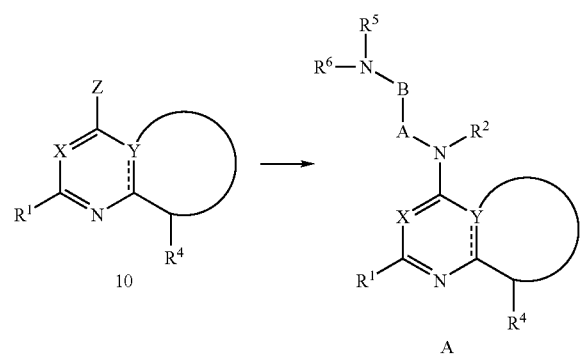

SCHEME 1

As illustrated in scheme 1, compounds of formula A can be prepared from intermediate compounds of formula 10, where Z is halogen (preferably chloro or bromo), alkane sulfonyloxy, aryl sulfonyloxy or haloalkane sulfonyloxy, and where $R^1$, $R^2$, $R^4$, $R^5$, $R^6$, X, Y, A, and B are defined above, using the procedures outlined below.

Compounds of formula 10 react with an amine of formula $H_2N$-A-B—$N[R^6]$—$R^5$, where A, B, $R^5$ and $R^6$ are defined as above, in the presence or absence of a base in the presence or absence of an inert solvent at reaction temperatures ranging from −78° C. to 250° C. to generate compounds of formula A. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably $CH_2Cl_2$). Preferred reaction temperatures range from 0° C. to 140° C.

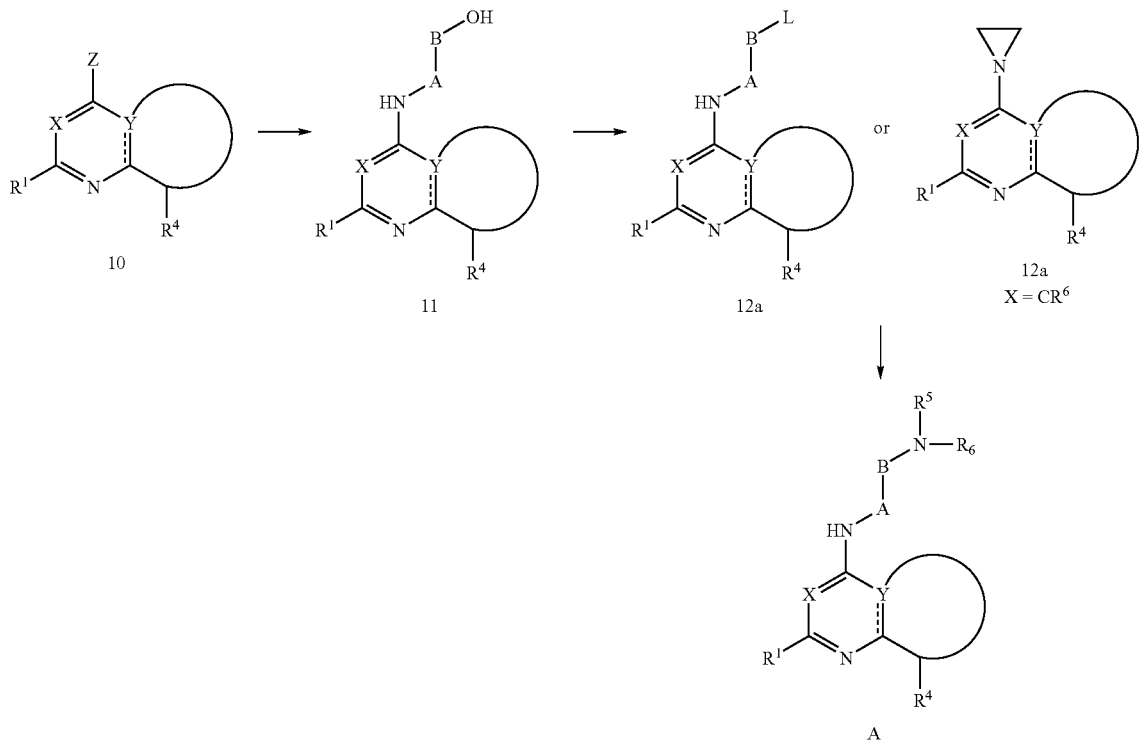

SCHEME 2

Alternatively, as illustrate in scheme 2, compounds of formula A can be obtained by first reacting a compound of formula 10 with an amino alcohol of formula H₂N-A-B—OH, where A and B are defined as above, in the presence or absence of a base in the presence or absence of an inert solvent at reaction temperatures ranging from −78° C. to 250° C. to generate intermediates of formula 11. Reacting a compound of formula 11 with a halogenating agent or sulfonylating agent in the presence or absence of a base in the presence or absence of an inert solvent at reaction temperatures ranging from −78° C. to 250° C. to afford products of formula 12a (where Z is halogen, alkane sulfonyloxy, aryl sulfonyloxy or haloalkane sulfonyloxy) or 12b when A and B are both CH₂ and X is CR¹⁴. Halogenating agents include, but are not limited to, SOCl₂, POCl₃, PCl₃, PCl₅, POBr₃, PBr₃, PBr₅., CCl₄PPh₃. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably CH₂Cl₂). Preferred reaction temperatures range from −20° C. to 100° C. Compounds of formula 12a or 12b can then be reacted with an amine of formula HN[R⁶]—R⁵, where R⁵ and R⁶ are defined as above, to give a compound of formula A Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably CH₂Cl₂). Preferred reaction temperatures range from 0° C. to 140° C.

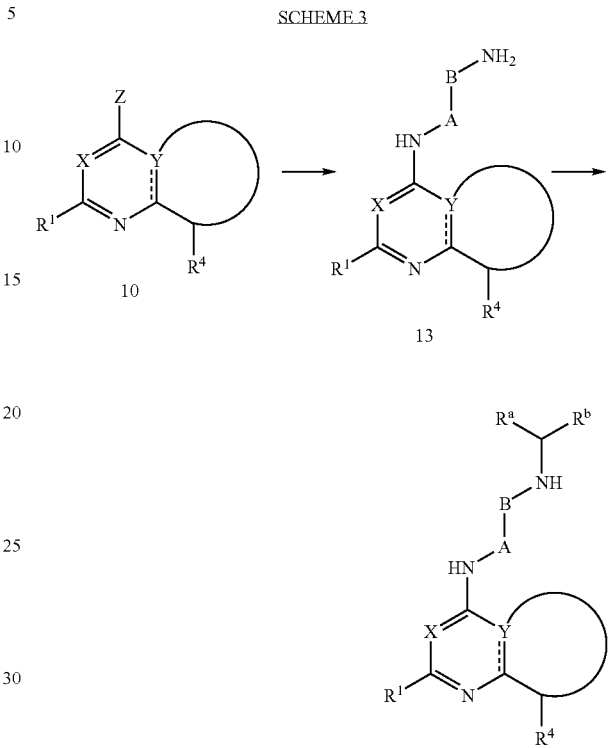

SCHEME 3

A subset of compounds of formula A, described under formula A1 (scheme 3), can be obtained by first reacting a compound of formula 10 with a diamine of formula H₂N-A-B—NH₂, where A and B are defined as above, in the presence or absence of a base in the presence or absence of an inert solvent at reaction temperatures ranging from −78° C. to 250° C. to generate intermediates of formula 13. Reaction of a compound of formula 13 with a ketone of Formula Rᵃ—C=O—Rᵇ in the presence of a reducing agent provides a compound of formula A1, where the grouping Rᵃ—CH—Rᵇ corresponds to R⁵ in formula A, as defined above. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethyl amine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene). Preferred reaction temperatures range from −78° C. to 100° C.

SCHEME 4

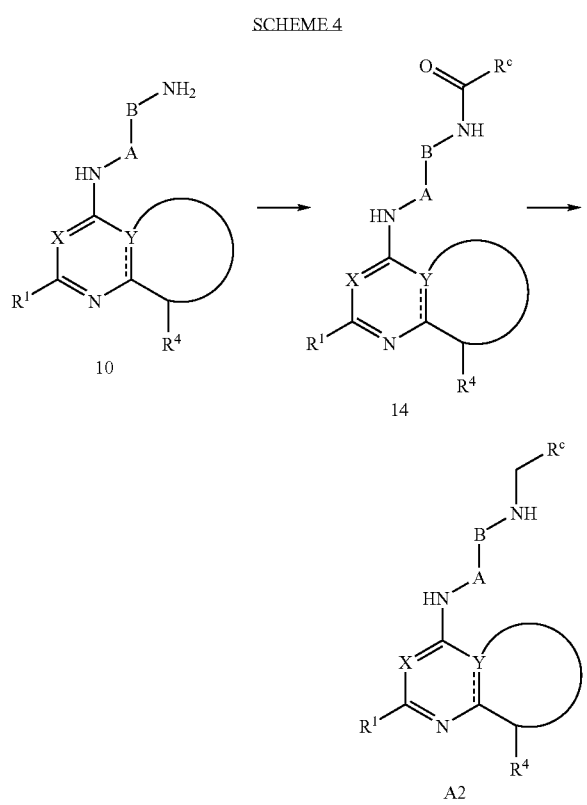

Alternatively, a subset of compounds of formula A, described under formula A2 (scheme 4), can be obtained by first reacting a compound of formula 13 with an activated acid of formula $R^c$—C=O-Z, where Z is halo (preferably chloro), O-acyl (preferably O—C=O—$R^c$), in the presence or absence of a base in the presence or absence of an inert solvent at reaction temperatures ranging from −78° C. to 250° C. to generate an amide intermediate of formula 14. Reaction of a compound of formula 14 with a reducing agent provides a compound of formula A2, where the grouping $R_c$—$CH_2$ corresponds to $R^5$ in formula A, as defined above. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy) aluminum hydrides (such as triethoxyaluminum hydride), dialkyl aluminum hydrides (such as di-isobutyl aluminum hydride), alane (preferably complexed with dimethyl amine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene). Preferred reaction temperatures range from −78° C. to 100° C.

SCHEME 5

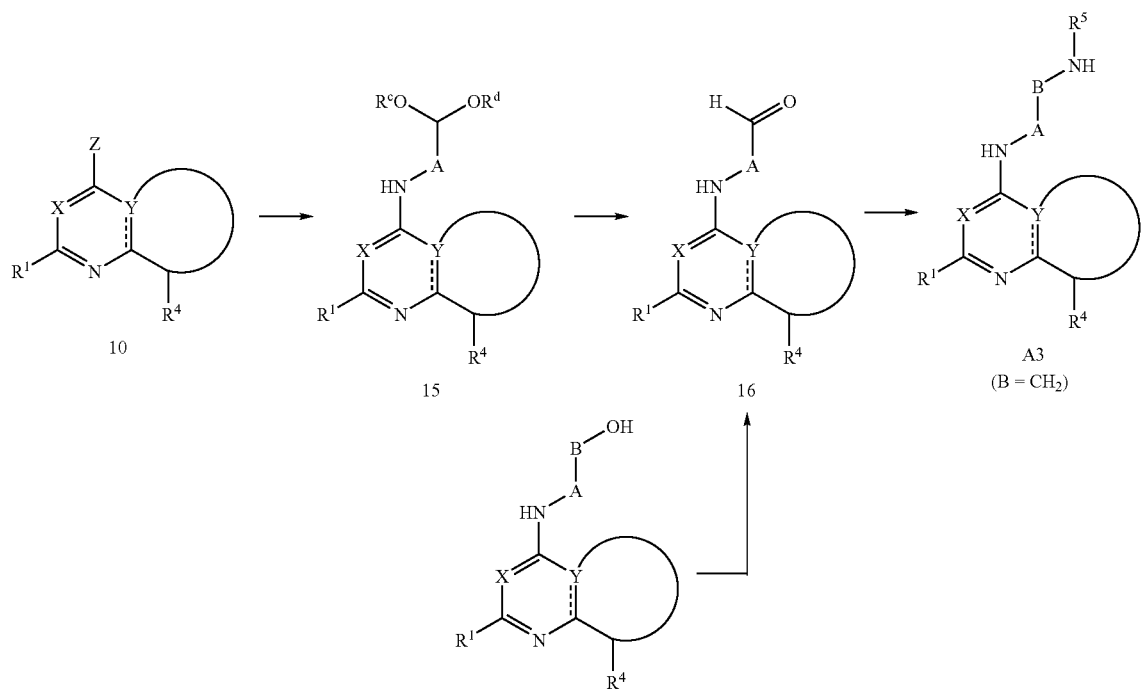

Alternatively, a subset of compounds of formula A, described under formula A3 (scheme 5), can be obtained by first reacting a compound of formula 10 with an amine of formula $H_2N$-A-CH($OR^c$)($OR^d$), where A is defined above, and $R^c$ and $R^d$ are $C_1$–$C_6$ lower alkyls or, taken together, complete a ketal group, such as, for example a dioxane or dioxolane group, in the presence or absence of a base in the presence or absence of an inert solvent at reaction temperatures ranging from −78° C. to 250° C. to generate compounds of formula 15. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably $CH_2Cl_2$). Compounds of formula 15 react with a protic acid in the presence or absence of an inert solvent at reaction temperatures ranging from −78° C. to 250° C., followed by aqueous work-up to generate compounds of formula 16. Inert solvents may include, but are not limited to dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably $CH_2Cl_2$). Protic acids include, but are not limited to, formic acid, acetic acid, trifluoroacetic acid, hydrochloric acid, methane sulfonic acid. Alternatively, compounds of formula 16 can be obtained by oxidation of compounds of formula 11 where B=$CH_2$. Oxidizing agents include, but are not limited to, transition metal oxides, such as $CrO_3$ or $MnO_2$, pyridine-chromium complexes, such as $CrO_3.C_5H_5N$, pyridinium dichromate or pyridinium chlorochromate, or an oxalyl chloride-DMSO-triethylamine reagent (Swern oxidation). Compounds of formula 16 react with amines of formula $H_2N$—$R^5$, where $R^5$ is defined above, in the presence of a reducing agent in the presence or absence of an inert solvent in the presence or absence of a protic acid at temperatures ranging from −78° C. to 100° C., to give compounds of formula A3. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethyl amine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene).

Compounds of formula 10, encompassing the heterocyclic cores of formula I–XV, are prepared according to procedures described in the references listed below.

Compounds of formula 10a, used as starting material for the preparation of compounds of formula 1, can be obtained according to scheme 6.

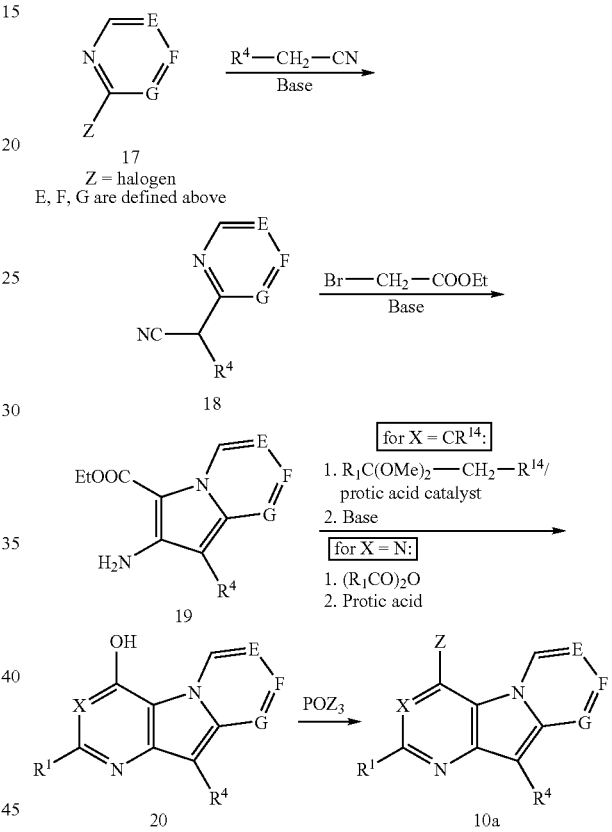

SCHEME 6

Compounds of formula 17, where E, F, and G are defined above and Z is a halogen, react with a compound of formula $R^4$—$CH_2$—CN, where $R^4$ is defined above, in the presence of base, in the presence or absence of an inert solvent, at reaction temperatures ranging from −78° C. to 100° C., to generate compounds of formula 18. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), dialkyl ethers (preferably diethyl ether), cyclic ethers (preferably tetrahydrofuran or 1,4-dioxane), or dialkylsulfoxides (preferably dimethylsulfoxide). Preferred reaction temperatures range from 0° C. to 100° C. Compounds of formula 18 then react with a compound of formula Z-CH$_2$—COOR$^c$, where Z is halogen (preferably chloro or bromo), alkane sulfonyloxy, aryl sulfonyloxy or haloalkane sulfonyloxy and R$^c$ is C$_1$–C$_6$ alkyl in the presence of base, in the presence or absence of an inert solvent, at reaction temperatures ranging from −78° C. to 100° C., to generate compounds of formula 19. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), dialkyl ethers (preferably diethyl ether), cyclic ethers (preferably tetrahydrofuran or 1,4-dioxane), or dialkylsulfoxides (preferably dimethylsulfoxide). Preferred reaction temperatures range from 0° C. to 100° C. Compounds of formula 20, where X is CR$^{14}$ and R$^1$ is defined above, can be obtained in two consecutive steps from compounds of formula 19 can be first reacted with a compound of formula R$^1$C(OR$^c$)—CH$_2$—R$^{14}$, where R$^c$ is methyl or ethyl, in the presence of base, in the presence or absence of an inert solvent, at reaction temperatures ranging from −78° C. to 100° C., to generate an non-isolated imine intermediate. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), dialkyl ethers (preferably diethyl ether), cyclic ethers (preferably tetrahydrofuran or 1,4-dioxane), or dialkylsulfoxides (preferably dimethylsulfoxide). Preferred reaction temperatures range from 0° C. to 100° C. In a second step, the imine intermediates are cyclized to a compound of formula 20 (X═CR$^{14}$) in the presence of base, in the presence or absence of an inert solvent, at reaction temperatures ranging from −78° C. to 100° C. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), dialkyl ethers (preferably diethyl ether), cyclic ethers (preferably tetrahydrofuran or 1,4-dioxane), or, dialkylsulfoxides (preferably dimethylsulfoxide). Preferred reaction temperatures range from 0° C. to 100° C.

Compounds of formula 20, where X is N and R$^1$ is defined above, can be obtained by reacting compounds of formula 19 with a compound of formula R$^1$—C═O—R$^c$, and R$^c$ is halogen, cyano, lower alkoxy (1–6 carbons), or lower alkanoyloxy (1–6 carbons), in the presence of a base in an inert solvent at reaction temperatures ranging from −78° C. to 200° C. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene). Compounds of formula 10a, where Z is halogen, alkane sulfonyloxy, aryl sulfonyloxy or haloalkane sulfonyloxy and X is N, can be prepared by reacting a compound of formula 20 with a halogenating agent or sulfonylating agent in the presence or absence of a base in the presence or absence of an inert solvent at reaction temperatures ranging from −78° C. to 250° C. Halogenating agents include, but are not limited to, SOCl$_2$, POCl$_3$, PCl$_3$, PCl$_5$, POBr$_3$, PBr$_3$, or PBr$_5$. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably CH$_2$Cl$_2$). Preferred reaction temperatures range from −20° C. to 100° C.

Alternatively, some of the compounds of formula A can be obtained from compounds of formula 21, as illustrated in scheme 7.

SCHEME 7

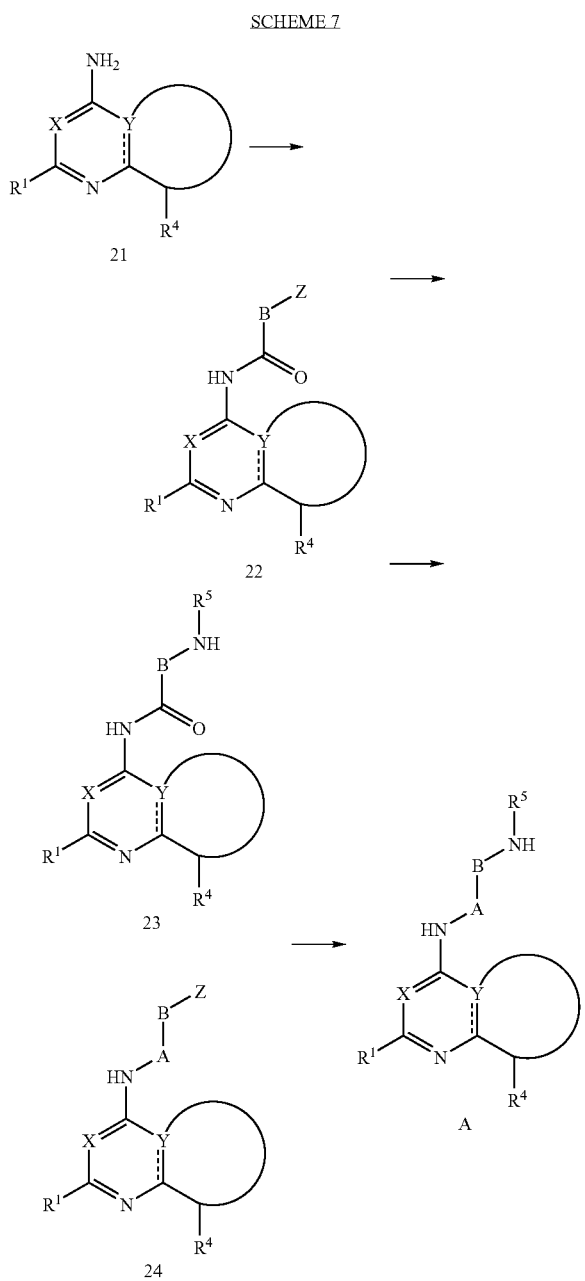

Compounds of formula 21, where X, $R^1$ and $R^4$ are defined above, react with a compound of formula Z-B—(C=O)—$R^c$, where B is defined above, Z is halogen (preferably chloro or bromo), alkane sulfonyloxy, aryl sulfonyloxy or haloalkane sulfonyloxy, and $R^c$ is halogen, cyano, lower alkoxy (1–6 carbons), or lower alkanoyloxy (1–6 carbons), in the presence or absence of a base, in the presence or absence of an inert solvent at reaction temperatures ranging from –78° C. to 200° C., to produce compounds of formula 22. Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably $CH_2Cl_2$). Preferred reaction temperatures range from –20° C. to 100° C.

Amides of formula 22 can be reacted with an amine of formula $NH[R^6]R^5$, where $R^6$ and $R^5$ are defined above, in the presence or absence of a base, in the presence or absence of an inert solvent at reaction temperatures ranging from –78° C. to 200° C., to produce compounds of formula 23. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably $CH_2Cl_2$). Preferred reaction temperatures range from 0° C. to 140° C.

Compounds of formula 23 can be reacted with a reducing agent in the presence or absence of an inert solvent to provide compounds of formula A, as defined above. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy) aluminum hydrides (such as triethoxyaluminum hydride), dialkyl aluminum hydrides (such as di-isobutyl aluminum hydride), alane (preferably complexed with dimethyl amine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene). Preferred reaction temperatures range from –78° C. to 100° C.

Alternatively, compounds of formula 22 can be reduced first, under experimental conditions similar to those used for the conversion of compounds of formula 23 to compounds of formula A, to generate compounds of formula 24. Compounds of formula 24 can then be reacted with compounds of formula $NH[R^6]R^5$, as defined above, under experimental conditions similar to those used for the conversion of compounds of formula 22 to compounds of formula 23, to generate compounds of formula A.

Other compounds of formula 10 and of formula 21, used as starting material for the preparation of compounds of formula II–XV, can be obtained according to procedures described in the following references:

Formula II: WO 9413676, WO 9534563, WO 9845295, EP 729758, *J. Med. Chem.*, 40(11), 1749–1754 (1997), *Bioorg. Med. Chem. Lett.*, 9(7), 967–972 (1999), *J. Med. Chem.*, 42(5), 819–832 (1999); *J. Med. Chem.* 42(5), 833–848 (1999);

Formula III: WO 9635689, WO 9729110, WO 9808847, WO 9847903, WO 9940091, U.S. Pat. No. 5,664,057;

Formula IV: WO 9413677, WO 9534563, EP 0729758;

Formula V: WO 9533750, *J. Med. Chem.* 42(5), 833–848 (1999); *Bioorg. Med. Chem. Lett.*, 9(7), 967–972 (1999);

Formula VI: WO 9808847, WO 9829397;

Formula VII: EP 239191, U.S. Pat. No. 5,273,608;

Formula VIII: U.S. Pat. No.5,273,608;

Formula IX: WO 9510506, WO 9735539, WO 9808847, WO 9842706, *J. Med. Chem.* 42(5), 833–848 (1999);

Formula X: WO 9808847, WO 9835967;

Formula XI: WO 9533750, *Bioorg. Med. Chem. Lett.*, 9(7), 967–972 (1999);

Formula XII: WO 9808847, WO 9835967;

Formula XIII: WO 9744038;

Formula XIV: WO 9808846; WO 9829397, WO 9835967, WO 9847874, WO 9912908;

Formula XV: WO 9510506, WO 9533750, WO 9714684, WO 9735580, WO 9842699, EP 778277, *J. Med. Chem.* 39(22), 4358–4360 (1996), *J. Med. Chem.* 42(5), 805–818 (1999), *J. Med. Chem.* 42(5), 833–848 (1999).

EXAMPLES

The following examples are which a provided to further illustrate the reaction schemes are not to be construed as limiting the invention.

The preparation of the compounds of the present invention by the above-mentioned methods is illustrated further by the following examples and those delineated in the Tables which are not to be construed as limiting the invention in scope or spirit to the specific procedures and compounds described in them. Commercial reagents were used without further purification. THF refers to tetrahydrofuran. LDA refers to lithium diisopropylamide and DBU refers to 1,8-diazabicyclo[5.4.0]undec-7-ene. Room or ambient temperature refers to 20° C. to 25° C. Concentration implies the use of a rotary evaporator. TLC refers to thin layer chromatography. Mass spectral data were obtained either by CI or APCI methods. Commonly used abbreviations are: Ph is phenyl, Me is methyl, Et is ethyl, Pr is n-propyl, iPr is isopropyl, Bu is butyl, iBu is isobutyl ($CH_2$—$CHMe_2$), tBu is tert-butyl, cBu is cyclobutyl, Pent is n-pentyl, cPent is cyclopentyl, cHex is cyclohexyl, Py is pyridyl, MeOH means methanol, EtOH means ethanol, EtOAc means ethyl acetate, $Et_2O$ means diethyl ether, $CH_2Cl_2$ means methylene chloride, DMSO means dimethyl sulfoxide, NMP means N-methyl pyrrolidone, THF means tetrahydrofuran, DMF means dimethyl formamide, EX means example. The specific heterocyclic cores, generically described under formula A, are indicated in the table under Formula, which refers to the heterocyclic core defined in formula I–XV.

Example 1

A. 2-(2-Pyridinyl)-2-(2,4,6-trimethylphenyl) ethanenitrile

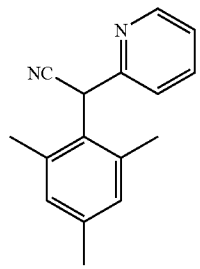

Add dropwise over a 1-hour period a mixed solution of 2-(2,4,6-trimethylphenyl)ethanenitrile (20 g; 0.126 mol) and 2-bromopyridine (35 g; 0.22 mol) in DMSO (25 mL) to a solution of potassium t-butoxide (35 g; 0.31 mol) dissolved in DMSO (125 mL). After the addition, stir the mixture for 4 h at ambient temperature and slowly pour into a stirred, ice-cold solution of $NH_4Cl$ with vigorous stirring. Filter the resulting tan precipitate, wash with MeOH, and air-dry to obtain the title compound as a pale yellow solid: $^1$H NMR (400 MHz, $CDCl_3$) δ 2.30 (s, 6H), 2.32 (s, 3H), 5.76 (s, 1H), 6.93 (s, 2H), 7.12 (d, 1H), 7.21 (dd, 1H), 7.63 (t, 1H), 8.63 (d, 1H).

B. Ethyl 2-amino-1-(2,4,6-trimethylphenyl)indolizine-3-carboxylate

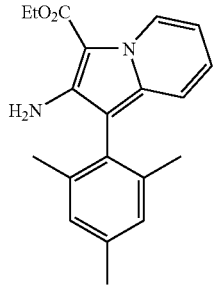

Slowly add dropwise ethyl bromoacetate (23 mL; 0.21 mol) over a 3-hour period to a mixture of 2-(2-pyridinyl)-2-(2,4,6-trimethylphenyl)-ethanenitrile (22.3 g; 0.094 mol) and potassium carbonate (78 g; 0.57 mol) suspended in DMSO (100 mL). Stir the mixture for 1 day, pour into an aqueous $NH_4Cl$ solution (ca. 1 L), and extract with 3×200 mL of $Et_2O$. Wash the combined extracts with saturated brine, dry over $Na_2SO_4$, filter, and concentrate in vacuo. Dissolve the residue in THF (200 mL), cool to 0° C., and add slowly in portions potassium t-butoxide (12 g; 0.11 mol) over a 10-minute period. After 30 minutes at 0° C., dilute the mixture with aqueous $NH_4Cl$ and extract with 2×150 mL of 50% $Et_2O$ in hexane. Wash the combined extracts with saturated brine, dry over $Na_2SO_4$, filter, concentrate in vacuo, and purify by column chromatography on silica gel (eluent: 5 to 10% EtOAc in hexane) to obtain the title compound as an oil: $^1$H NMR (400 MHz, $CDCl_3$) δ 1.47 (t, 3H), 2.06 (s, 6H), 2.35 (s, 3H), 4.46 (br q, 2H), 6.6 (br t, 1H), 6.75 (d, 1H), 6.9 (br t, 1H), 7.00 (s, 2H), 9.4 (1H).

C. 2-Methyl-9-(2,4,6-trimethylphenyl)pyrido[2,3-b]-indolizin-4-ol

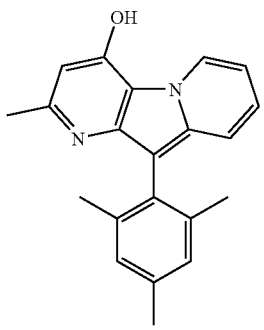

To a solution of 2-ethyl 2-amino-1-(2,4,6-trimethylphenyl)indolizine-3-carboxylate (19.2 g; 59.6 mmol) in 2,2-dimethoxypropane (100 mL), add dl-camphorsulfonic acid (0.2 g). Stir the mixture at reflux for 30 min and then distill slowly to remove ca. 60 mL of volatiles over a 30-minute period. Cool the solution to ambient temperature under inert atmosphere, dilute with anhydrous toluene (50 mL), and concentrate in vacuo. Dissolve the residue in toluene (50 mL) and add dropwise over a 1-hour period a 0.5 M solution of potassium bis(trimethylsilyl)amide in toluene (250 mL; 125 mmol) to the stirred solution. After the addition, stir the mixture for 2 h at ambient temperature, concentrate in vacuo to a small volume and dilute with aqueous $NH_4Cl$. Filter the resulting biphasic mixture and wash successively with water, MeOH, and $Et_2O$. Dry under vacuum to obtain the title compound as a pale yellow solid.

D. 4-Chloro-2-methyl-9-(2,4,6-trimethylphenyl)pyridino[2,3-b]-indolizine

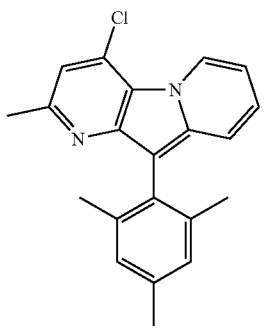

Heat at 100° C. for 1 h a solution of 4-hydroxy-2-methyl-10-(2,4,6-trimethylphenyl)pyridino-[2,3-b]indolizine 2-methyl-9-(2,4,6-trimethylphenyl)pyrido[2,3-b]-indolizin-4-ol (10.1 g; 32 mmol) in phosphorus oxychloride (60 mL), cool to ambient temperature, and concentrate in vacuo. Partition the residue into ice water and $CH_2Cl_2$. Separate the aqueous phase, extract twice with $CH_2Cl_2$, and wash the combined organic extracts with a 1 N aqueous sodium hydroxide solution and then with water. Dry the solution over $Na_2SO_4$, filter, and concentrate in vacuo. Filter the dark residue through a short pad of silica gel and wash with 25% EtOAc in hexane. Concentrate the filtrate in vacuo to obtain the title compound as a yellow solid: $^1H$ NMR (400 MHz, $CDCl_3$) δ 2.00 (s, 6H), 2.37 (s, 3H), 2.64 (s, 3H), 6.58 (t, 1H), 6.95 (dd, 1H), 7.00 (s, 2H), 7.07 (s, 1H), 7.08 (d, 1H), 9.26 (d, 1H).

E. (2-Aminoethyl)[2-methyl-9-(2,4,6-trimethylphenyl)-pyridino[2,3-b]indolizin-4-yl]amine

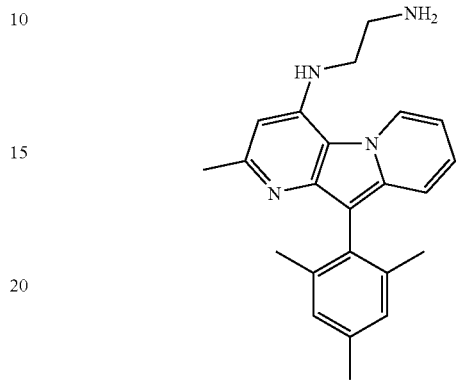

Heat a solution of 4-chloro-2-methyl-9-(2,4,6-trimethylphenyl)pyridino[2,3-b]-indolizine (0.35 g, 1.04 mmol), and ethylene diamine (0.32 g, 1.04 mmol) in dry NMP (3 mL) at 100° C. for 5 h. Pour the cooled mixture onto water (30 mL) and extract twice with EtOAc (30 mL). Wash the combined extract with brine (30 mL), dry, and evaporate in vacuo. Purify by preparative TLC (20% MeOH in $CH_2Cl_2$ with 1% ammonium hydroxide) to obtain the title compound as a colorless oil.

F. 2-(4-Ethoxy-3-methoxy-phenyl)-N-{2-[2-methyl-9-(2,4,6-trimethyl-phenyl)-pyridino[2,3-b]indolizin-4-ylamino]-ethyl}-acetamide

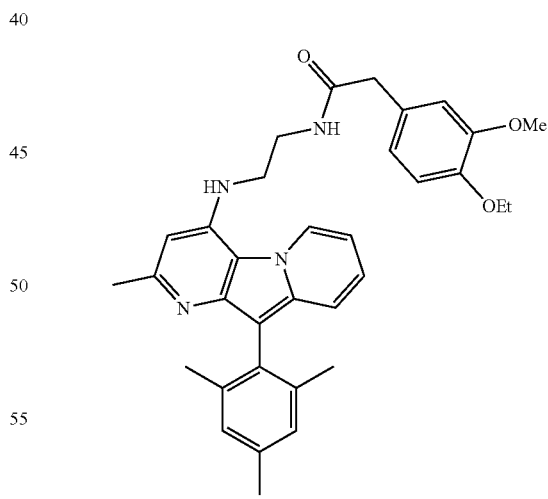

Treat a solution of (2-aminoethyl)[2-methyl-9-(2,4,6-trimethylphenyl)-pyridino[2,3-b]indolizin-4-yl]amine (0.08 g, 0.22 mmol), 4-ethoxy, 3 methoxy phenylacetic acid (0.05 g, 0.22 mmol) and N,N diisopropylethyl amine (0.04 mL, 0.24 mmol) in $CH_2Cl_2$ (10 mL) with benzotriazol-1-yloxy-tris-(dimethylamino)phosphonium hexafluorophosphate (0.1 g, 0.24 mmol) and stir at ambient temperature for 14 h. Dilute the resulting mixture with $CH_2Cl_2$ (20 mL), water (20 mL), and saturated aq NaCl (20 mL). Dry the organic layer over Na$_2$SO$_4$, filter and concentrate in vacuo. Purify by preparative TLC (10% MeOH in CH$_2$Cl$_2$) to obtain the title compound as a solid.

G. (2-{[2-(4-Ethoxy-3-methoxyphenyl)ethyl]amino}ethyl)[2-methyl-9-(2,4,6-trimethylphenyl)pyridino[2,3-b]indolizin-4-yl]amine

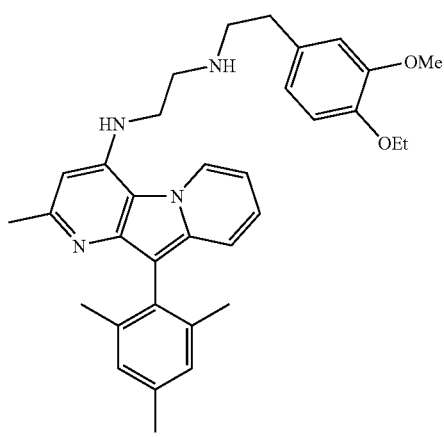

Treat a solution of 2-(4-ethoxy-3-methoxy-phenyl)-N-{2-[2-methyl-9-(2,4,6-trimethyl-phenyl)-pyridino[2,3-b]indolizin-4-ylamino]-ethyl}-acetamide (0.08 g, 0.145 mmol) in THF (5 mL) with AlH$_3$.NMe$_2$Et (3 mL, 1.45 mmol) and heat to reflux for 14 h. Cool the resulting mixture to ambient temperature, quench with Na$_2$CO$_3$.10H$_2$O (0.3 g) and stir at ambient temperature for 15 min. Filter the solution through Celite and wash with several portions of CH$_2$Cl$_2$. Concentrate the filtrate in vacuo to dryness and purify by preparative TLC (10% MeOH in CH$_2$Cl$_2$ with 0.5% ammonium hydroxide) to the title compound as a solid.

Example 2

A. 2-Methyl-9-(2,4,6-trimethylphenyl)pyrimidino[4,5-b]indolizin-4-ol

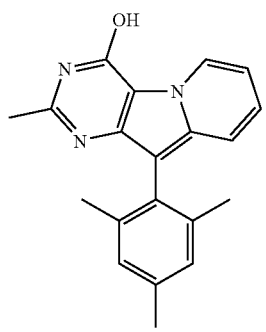

Heat to 100° C. for 1 h a solution of 2-amino-3-cyano-1-(2,4,6-trimethylphenyl)indolizine (220 mg) in an acetic anhydride (0.5 mL)—acetic acid (2 mL) mixture. Cool the mixture to ambient temperature before concentrating in vacuo. Heat the residue in 85% phosphoric acid (5 mL) at 100° C. for 1.5 h, allow to cool to ambient temperature, dilute with water, and neutralize to pH 7 by adding aqueous NaOH. Extract the resulting yellow suspension twice with CH$_2$Cl$_2$ and dry the combined extracts on Na$_2$SO$_4$, filter, concentrate, and purify by column chromatography on silica gel (eluent: 50% EtOAc in hexane to 10% MeOH in EtOAc) to obtain the title compound as a yellow solid.

B. 4-Chloro-2-methyl-9-(2,4,6-trimethylphenyl)pyrimidino[4,5-b]indolizine

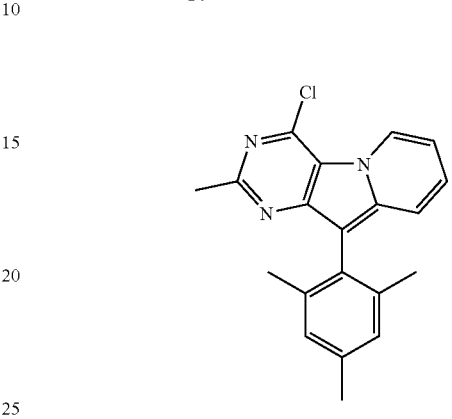

Heat at 100° C. for 2 h a solution of 2-methyl-9-(2,4,6-trimethylphenyl)pyrimidino[4,5-b]indolizin-4-ol (120 mg) in phosphorus oxychloride (2 mL), cool to ambient temperature, and concentrate in vacuo. Partition the residue into ice water and CH$_2$Cl$_2$. Extract the aqueous phase twice with CH$_2$Cl$_2$ and wash the combined organic extracts with a saturated NaHCO$_3$ solution. Dry the solution over Na$_2$SO$_4$, filter, and concentrate in vacuo. Purify the dark residue by column chromatography on silica gel (eluent: 10% to 20% EtOAc in hexane) to obtain the title compound as a greenish yellow foam: $^1$H NMR (400 MHz, CDCl$_3$) δ 1.99 (s, 6H), 2.38 (s, 3H), 2.79 (s, 3H), 6.80 (m, 1H), 7.00 (s, 2H), 7.19 (m, 2H), 9.27 (d, 1H).

C. (2-Aminoethyl)[2-methyl-9-(2,4,6-trimethylphenyl)pyrimidino[4,5-b]indolizin-4-yl]amine

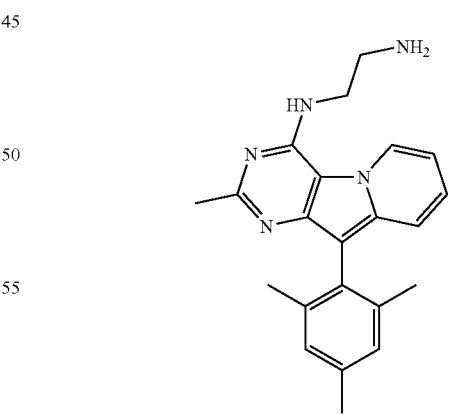

Heat a solution of 4-chloro-2-methyl-9-(2,4,6-trimethylphenyl)pyrimidino[4,5-b]indolizine (0.3 g, 0.89 mmol), and ethylene diamine (0.6 mL, 8.93 mmol) in dry NMP (3 mL) at 100° C. for 14 h. Pour the cooled mixture onto water (30 mL) and extracte twice with EtOAc (30 mL). Wash the combined extracts with brine (30 mL), dry, and evaporate in vacuo. Purify by preparative TLC (20% MeOH in CH₂Cl₂ with 0.5% ammonium hydroxide) to obtain the title compound as a yellow oil.

D. [2-(Cyclopentylamino)ethyl][2-methyl-9-(2,4,6-trimethylphenyl)pyrimidino[4,5-b]indolizin-4-yl]amine

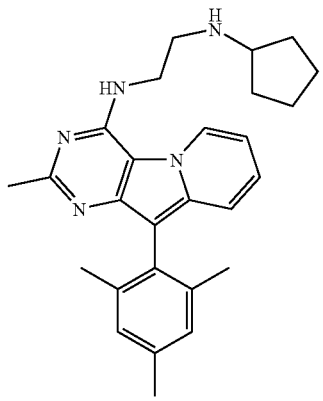

Treat a solution of (2-aminoethyl)[2-methyl-9-(2,4,6-trimethylphenyl)pyrimidino[4,5-b]indolizin-4-yl]amine (0.07 g, 0.19 mmol), cyclopentanone (0.02 mL, 0.19 mmol) and acetic acid (0.01 mL, 0.19 mmol) in dry dichloroethane (3 mL) with sodium triacetoxyborohydride (0.06 g, 0.27 mmol) and stir at ambient temperature for 14 h. Dilute the resulting mixture with CH₂Cl₂ (20 mL) and wash with saturated aq NaCl (50 mL). Dry the organic portion over Na₂SO₄, filter, and concentrate under reduced pressure. Purify by preparative TLC (10% MeOH in CH₂Cl₂ with 0.5% ammonium hydroxide) to obtain the title compound as a yellow solid.

Example 3

A. N-(2-Amino-ethyl)-2-(4-ethoxy-3-methoxy-phenyl)-acetamide

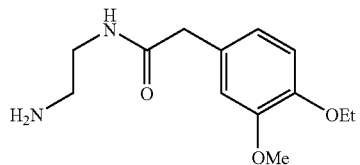

Dissolve 4-ethoxy-3-methoxy-phenyl acetic acid (26 g, 119 mol) in dichloroethane (300 mL, anhydrous) and cool to 0° C. Dropwise add oxalyl chloride (130 mL, 2.0 M in CH₂Cl₂) and DMF (2 mL), then allow to warm to ambient temperature for 14 h. Concentrate under reduced pressure to a tan oil. Dissolve in dichloroethane (200 mL) and cool to 0° C. while stirring under N₂. Dropwise, over 45 minutes, add a second solution of N-tBOC-ethylenediamine (20 g) and triethylamine (20 mL) in dichloroethane (100 mL). Partition between CH₂Cl₂ (500 mL) and 1.0 N HCl (200 mL), separate the layers, and wash the organic phase with 1.0 N HCl (200 mL). Wash the organic layer with saturated K₂CO₃ (2×200 mL), then dry the CH₂Cl₂ layer over Na₂SO₄, filter, and evaporate to tan solid. Triturate with Et₂O (200 mL) and stir vigorously to fragment solid, then filter and wash copiously with Et₂O to obtain a white solid. Dissolve the white solid (3.0 g, 8.52 mmol) in a 1:1 mixture of trifluoracetic acid and CH₂Cl₂ (10 mL) and stir at ambient temperature 1 h. Concentrate under reduced pressure and partition between CH₂Cl₂ (25 mL) and 1.0 N NaOH (25 mL), then separate the layers, and extract the aqueous layer with CH₂Cl₂ (25 mL). Pool the organic layers, dry over Na₂SO₄, filter and concentrate in vacuo to a white solid.

B. N-(4-Ethoxy-3-methoxy-phenethyl)-ethylenediamine

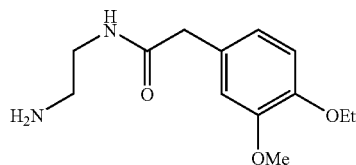

Treat a solution of N-(2-amino-ethyl)-2-(4-ethoxy-3-methoxy-phenyl)acetamide (0.7 g, 2.77 mmol) in THF (10 mL) with AlH₃.NMe₂Et (55 mL, 27.74 mmol) and heat to reflux for 14 h. Cool the resulting mixture to ambient temperature, quench with Na₂CO₃.10H₂O (0.5 g) and stir at ambient temperature for 15 min. Filter the solution through Celite and wash with several portions of CH₂Cl₂. Concentrate the filtrate in vacuoo and purify by preparative TLC (10% MeOH in CH₂Cl₂) to obtain the title compound as a white oil.

C. (2-{[2-(4-Ethoxy-3-methoxyphenyl)ethyl]aminol}ethyl)[2,5,6-trimethyl-7-(2,4,6-trimethylphenyl)pyrrolo[3,2-e]pyrimidin-4-yl]amine

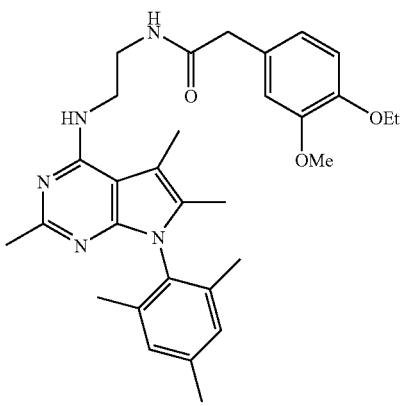

Heat a solution of 4-chloro-2,5,6-trimethyl-7-(2,4,6-trimethyl-phenyl)-7H-pyrrolo[2,3-d]pyrimidine (340 mg, 1.1 mmol) and N-(4-ethoxy-3-methoxy-phenethyl)-ethylenediamine in NMP (2 mL) for 14 h at 130° C. Pour into water (5 mL) and extract with EtOAc (2×10 mL). Dry the combined organic extracts over Na₂SO₄, filter, and concentrate under reduced pressure. Purify by preparative TLC, eluting with 10% MeOH in CH₂Cl₂. Dissolve the residue in a minimum amount of MeOH then add HCl in EtOAc (2 mL) and triturate with Et₂O to obtain the title-compound as a solid (HCl salt).

Example 4

A. 2-(4-Methoxyphenyl)-N-(2-{[7-(4-methoxy-2,6-dimethylphenyl)-2,5-dimethylpyrrolo[2,3-e]pyrimidin-4-yl]amino}ethyl)acetamide

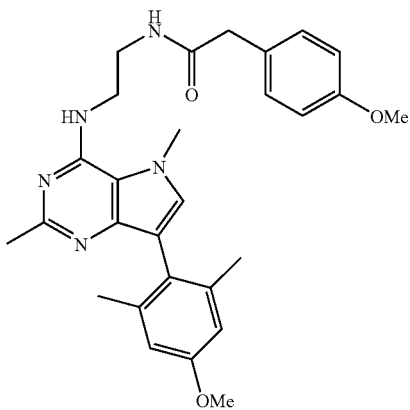

Heat a solution of 4-chloro-7-(4-methoxy-2,6-dimethylphenyl)-2,5-dimethyl-5H-pyrrolo[3,2-d]pyrimidine (120 mg, 0.38 mmol) and N-(2-amino-ethyl)-2-(4-methoxyphenyl)-acetamide (125 mg) in NMP (2 mL) for 14 h at 130° C. Pour into water (5 mL) and extract with EtOAc (2×10 mL). Dry the combined organic extracts over Na₂SO₄, filter, and concentrate under reduced pressure to obtain the title compound which is used without further purification.

B. (2-{[2-(4-Methoxyphenyl)ethyl]amino}ethyl)[7-(4-methoxy-2,6-dimethylphenyl)-2,5-dimethylpyrrolor[2,3-e]pyrimidin-4-yl]amine

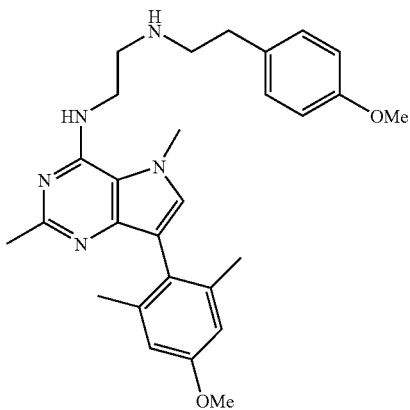

Dissolve 2-(4-methoxyphenyl)-N-(2-{[7-(4-methoxy-2,6-dimethylphenyl)-2,5-dimethylpyrrolo[2,3-e]pyrimidin-4-yl]aminoethyl)acetamide in anhydrous THF (5 mL) and stir under N₂. Add borane-dimethylsulfide complex (0.2 mL, 10.0 M in THF) and heat to reflux for 14 h. Quench by addition of N,N'-dimethyl-1,2-ethylenediamine (0.21 mL) in MeOH (5 mL) and stir for 1 h at ambient temperature. Concentrate under reduced pressure and purify the residue by preparative TLC, eluting with 10% MeOH in CH₂Cl₂. Dissolve the residue in a minimum amount of MeOH then add HCl in EtOAc (2 mL) and triturate with Et₂O to obtain the title compound as a solid (HCl salt).

Example 5

A. 4-Chloro-6-methyl-3-nitro-pyridin-2-ol

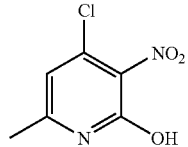

Add 1-ethylpropylamine (9.00 g, 76.4 mmol) to a solution of 4-hydroxy-6-methyl-3-nitropyridone (10.0 g, 58.8 mmol) in anhydrous MeOH (20 mL). Stir the mixture until clear, then concentrated in vacuo. Add the residue portionwise to phosphorus oxychloride (70 mL), Stir at ambient temperature for 10 h, and pour onto ice-water. After stirring for 20 min, filter the precipitate, and dry over Na₂SO₄ to obtain the title compound as a yellow solid.

B. 4-Benzylamino-6-methyl-3-nitro-pyridin-2-ol

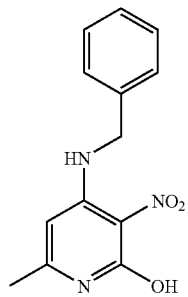

Stir a solution of 4-chloro-6-methyl-3-nitro-pyridin-2-ol (10.0 g, 53.0 mmol) and benzyl amine (17.3 g, 159 mmol) in EtOH (30 mL) at ambient temperature for 12 h, then concentrate in vacuo. Pour the resulting residue into water, acidify to pH 3 with 1N HCl and filter. Wash the precipitate several times with water to obtain the title compound as a yellow solid.

C. 4-Benzylamino-6-methyl-3-nitro-2-chloro-pyridine

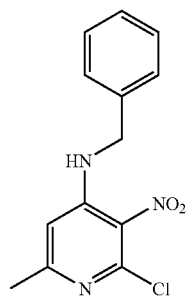

Heat a solution of 4-benzylamino-6-methyl-3-nitro-pyridin-2-ol (13.70 g, 52.8 mmol) and tetramethylammonium chloride (6.0 g, 52.8 mmol) to reflux in phosphorus oxychloride (15 mL) for 5 h. After cooling, remove the excess phosphorus oxychloride in vacuo. Triturate the residue in ice-water (400 mL) to obtain the title compound as a brown solid.

D. 6-Methyl-3-nitro-4-[benzylamino](2-pyridyl)}(2,4,6-trimethylphenyl)amine

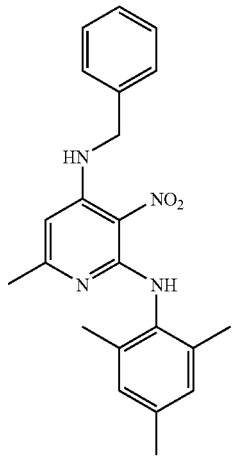

Add p-toluene sulfonic acid (11.0 g, 56.3 mmol) to a solution of 4-benzylamino-6-methyl-3-nitro-2-chloro-pyridine (13.0 g, 46.8 mmol) and 2,4,6-trimethylaniline (6.58 g, 46.8 mmol) in 350 mL of toluene. Heat the resulting mixture for 14 h under reflux using a Dean-Stark trap. After cooling to ambient temperature, dilute the solution with EtOAc (200 mL) and wash successively with saturated aq NaHCO₃ and saturated aq NaCl. Separate the organic layer, dry over Na₂SO₄, filter, and concentrate in vacuo. Purify by flash column chromatography (2% methanol in CH₂Cl₂) to obtain obtain the title compound as a dark yellow solid.

E. 3-Amino-6-methyl-4-[benzylamino](2-pyridyl)(2,4,6-trimethylphenyl)amine

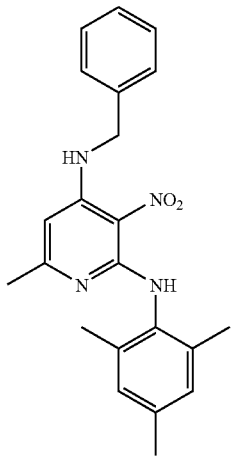

Add iron powder (7.0 g) to a solution of 6-methyl-3-nitro-4-[benzylamino](2-pyridyl)(2,4,6-trimethylphenyl)amine (8.75 g, 23.2 mmol) in acetic acid (14 mL) and MeOH (70 mL). Heat the resulting mixture at 70° C. for 1 h, cool to ambient temperature, and filter through a pad of celite. Evaporate the filtrate to dryness under reduced pressure. Treat he residue with 1N aq NaOH and extract with EtOAc. Wash the EtOAc extract with water and saturated aq NaCl. Separate the organic layer, dry over Na₂SO₄, filter, and concentrate to obtain the title compound as a brown solid which is used without further purification.

F. [5-methyl-3-(2,4,6-trimethylphenyl)imidazolo[5,4-b]pyridin-7-yl]benzylamine

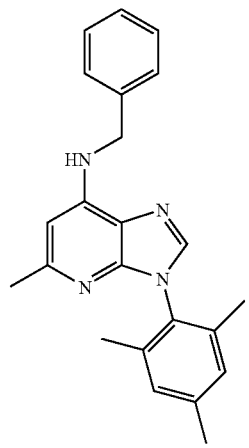

Treat a solution of 3-amino-6-methyl-4-[benzylamino](2-pyridyl)(2,4,6-trimethylphenyl)amine (0.80 g, 2.31 mmol) and triethyl orthoformate (8.0 mL, 48.5 mmol) in dimethylacetamide (9 mL) with 12 M HCl (0.4 mL). Stir the mixture at ambient temperature for 14 h, dilute with EtOAc (50 mL), and wash with aq NaHCO₃ (50 mL) and saturated aq NaCl (50 mL). Dry the organic layer over Na₂SO₄, filter, and concentrate. Purify by preparative TLC (10% methanol in CH$_2$Cl$_2$ with 0.1% ammonium hydroxide) to obtain the title compound as a solid.

G. 5-methyl-3-(2,4,6-trimethylphenyl)imidazolo[5,4-b]pyridin-7-ylamine

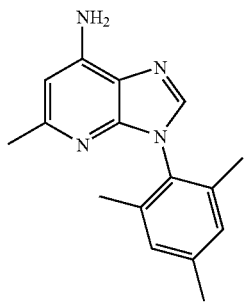

Add palladium hydroxide (0.05 g) to a solution of [2,5-dimethyl-3-(2,4,6-trimethylphenyl)imidazolo[5,4-b]pyridin-7-yl]benzylamine (0.15 g, 0.42 mmol) in acetic acid (10 mL). Hydrogenate the mixture at a pressure of 50 psi for 20 hr. Filter the reaction mixture through celite, evaporate to dryness under reduced pressure, dilute with EtOAc and successively wash with aq NaHCO$_3$ and aq NaCl. Dry the organic layer over Na$_2$SO$_4$, filter, and concentrate. Purify by flash column chromatography (3% MeOH in CH$_2$Cl$_2$) to obtain the title compound as a brown solid.

H. N-[5-methyl-3-(2,4,6-trimethylphenyl)imidazolo[5,4-b]pyridin-7-yl]-2-chloroacetamide

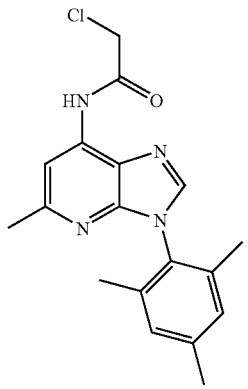

Treat a solution of 5-methyl-3-(2,4,6-trimethylphenyl)imidazolo[5,4-b]pyridin-7-ylamine (0.05 g, 1.9 mmol), and N,N-diisopropylethylamine, (0.04 mL, 0.21 mmol) in 1,2-dichloroethane (5 mL) with chloroacetyl chloride (0.017 mL, 0.21 mmol). Heat the solution to reflux for 3 h, cool to ambient temperature, and pour into an aqueous potassium carbonate solution. Extract the resulting mixture with CH$_2$Cl$_2$ and wash with saturated aq NaCl. Separate the organic layer, dry over Na$_2$SO$_4$, filter, and concentrate. Purify by preparative TLC (5% MeOH in CH$_2$Cl$_2$) to obtain the title compound as a yellow solid.

I. (2-Chloroethyl)[5-methyl-3-(2,4,6-trimethylphenyl)imidazolo[5,4-b]pyridin-7-yl]-amine

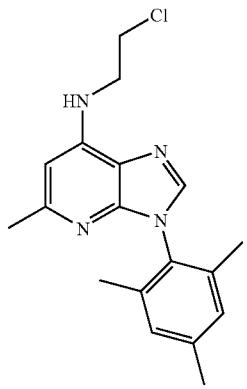

Treat a solution of N-[5-methyl-3-(2,4,6-trimethylphenyl)imidazolo[5,4-b]pyridin-7-yl]-2-chloroacetamide (0.04 g, 0.10 mmol) in THF (5 mL) with borane-methyl sulfide complex (0.03 mL, 0.30 mmol). Heat the mixture to reflux for 8 h and quench at ambient temperature with a large excess of MeOH, followed by 6 N HCl (2 mL). Re-heat the mixture to reflux for 1 h, then concentrate under reduced pressure to obtain the title compound as a yellow solid.

J. (2-{[2-(4-Ethoxy-3-methoxyphenyl)ethyl]amino}ethyl[5-methyl-3-(2,4,6-trimethylphenyl)imidazolo[5,4-b]pyridin-7-yl]amine

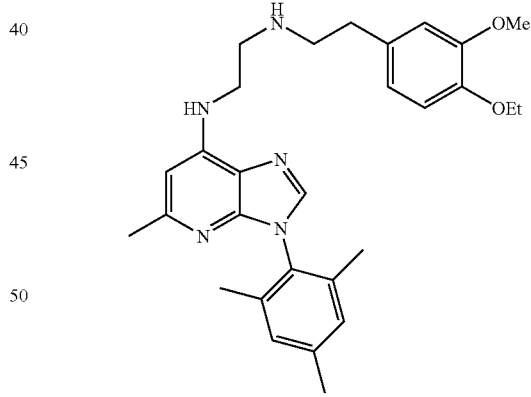

Heat a solution of (2-chloroethyl)[5-methyl-3-(2,4,6-trimethylphenyl)imidazolo[5,4-b]pyridin-7-yl]-amine (0.030 g, 0.09 mmol) and 4-ethoxy-3-methoxy phenethylamine (0.10 g, 0.55 mmol) in dry NMP (2 mL) at 110° C. for 16 h. Pour the cooled mixture onto water (20 mL) and extract twice with EtOAc (20 mL). Wash the combined extracts with brine (30 mL), dry, and evaporate in vacuo. Purify by flash column chromatography (10% MeOH in CH$_2$Cl$_2$ with 0.1% ammonium hydroxide) to obtain the title compound as a solid.

Example 6

A. [2,5-dimethyl-3-(2,4,6-trimethylphenyl)imidazolo[5,4-b]pyridin-7-yl]benzylamine

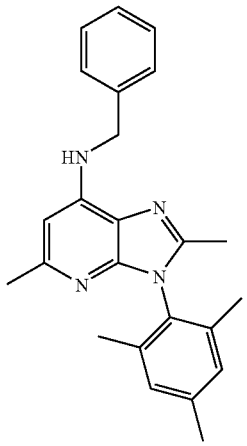

Heat a solution of 3-amino-6-methyl-4-[benzylamino](2-pyridyl)(2,4,6-trimethylphenyl)amine (2.50 g, 7.21 mmol), triethyl orthoacetate (2.6 mL, 14.4 mmol) and camphorsulfonic acid (250 mg) in toluene (50 mL) to reflux for 14 h. After cooling to ambient temperature, concentrate the mixture in vacuo, dilute with water (100 mL), and extract with EtOAc. Wash the EtOAc extract successively with water and saturated aq NaCl, dry over $Na_2SO_4$, filter, and concentrate. Purify by flash column chromatography (5% methanol in $CH_2Cl_2$) to obtain the title compound as a white solid.

B. 2,5-Dimethyl-3-(2,4,6-trimethylphenyl)imidazolo[5,4-b]pyridine-7-ylamine

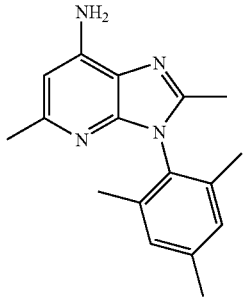

Add palladium hydroxide (2.0 g) to a solution of [2,5-dimethyl-3-(2,4,6-trimethylphenyl)imidazolo[5,4-b]pyridin-7-yl]benzylamine (1.50 g, 4.05 mmol) in acetic acid (10 mL). Hydrogenate the mixture at a pressure of 40 psi for 20 hr. Filter the reaction mixture through celite, evaporate to dryness under reduced pressure, dilute with EtOAc and successively wash with aq. $NaHCO_3$ and aq NaCl. Dry the organic layer over $Na_2SO_4$, filter, and concentrate. Purify by flash column chromatography (3% MeOH in $CH_2Cl_2$) to obtain the title compound as a white solid.

C. N-[2,5-Dimethyl-3-(2,4,6-trimethylphenyl)imidazolo[5,4-b]pyridin-7-yl]-2-chloroacetamide

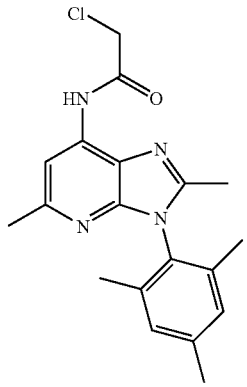

Treat a solution of 2,5-dimethyl-3-(2,4,6-trimethylphenyl)imidazolo[5,4-b]pyridine-7-ylamine (0.8 g, 2.85 mmol), and N,N-diisopropylethylamine, (0.54 mL, 3.13 mmol) in 1,2-dichloroethane (10 mL) with chloroacetyl chloride (0.25 mL, 3.13 mmol). Heat the solution to reflux for 5 h, cool to ambient temperature, and pour into an aqueous potassium carbonate solution. Extract the resulting mixture with $CH_2Cl_2$ and wash with saturated aq NaCl. Separate the organic layer, dry over $Na_2SO_4$, filter and concentrate. Purify by preparative TLC (5% MeOH in $CH_2Cl_2$) to obtain the title compound as a brown solid.

D. [2,5-Dimethyl-3-(2,4,6-trimethylphenyl)imidazolo[5,4-b]pyridin-7-yl](2-chloroethyl)amine

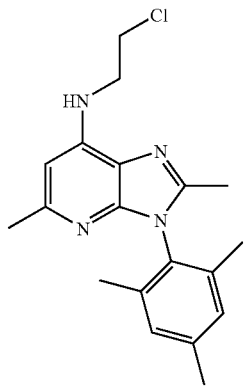

Treat a solution of N-[2,5-dimethyl-3-(2,4,6-trimethylphenyl)imidazolo[5,4-b]pyridin-7-yl]-2-chloroacetamide (0.91 g, 2.55 mmol) in THF (5 mL) with borane-methyl sulfide complex (0.8 mL, 7.65 mmol). Heat the mixture to reflux for 18 h and quench at ambient temperature with a large excess of MeOH, followed by 6N HCl (5 mL). Re-heat the mixture to reflux for 1 h, then concentrate under reduced pressure to obtain the title compound as a white crystalline solid.

E. [2,5-Dimethyl-3-(2,4,6-trimethylphenyl)imidazolo[5,4-b]pyridin-7-yl][2-(cyclohexylamino)ethyl]amine

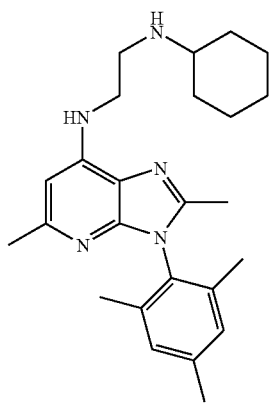

Heat a solution of [2,5-dimethyl-3-(2,4,6-trimethylphenyl)imidazolo[5,4-b]pyridin-7-yl](2-chloroethyl)amine (0.04 g, 0.12 mmol), and cyclohexyl amine (0.13 mL g, 1.16 mmol) in dry NMP (2 mL) at 80° C. for 20 h. Pour the cooled mixture onto water (20 mL) and extract twice with ethyl acetate (20 mL). Wash the combined extracts with brine (20 mL), dry, and evaporate in vacuo. Purify by flash column chromatography (10% methanol in $CH_2Cl_2$ with 0.1% ammonium hydroxide) to obtain the title compound as a white solid.

Example 7

A. 3-(2,4-dichlorophenyl)-2,5-dimethylimidazolo[5,4-b]pyridin-7-ylamine

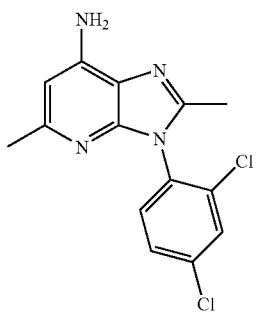

Stir a solution of [3-(2,4-dichlorophenyl)-2,5-dimethylimidazolo[5,4-b]pyridin-7-yl](4-methoxybenzyl)amine (4.23 g, 10 mmol), anisole (3.2 mL, 29.6 mmol), trifluoroacetic acid (80 mL), and concentrated sulfuric acid (2 mL) at ambient temperature for 14 h. Add the resulting mixture dropwise to ice-water and dilute with $NaHCO_3$. Filter the resulting precipitate and wash thoroughly with water to obtain the title compound as a brown solid.

B. N-[3-(2,4-dichlorophenyl)-2,5-dimethylimidazolo[5,4-b]pyridin-7-yl]-2-chloroacetamide

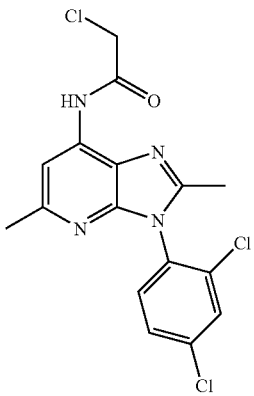

Treat a solution of 3-(2,4-dichlorophenyl)-2,5-dimethylimidazolo[5,4-b]pyridin-7-ylamine (0.2 g, 0.65 mmol), and N,N-diisopropylethylamine, (0.12 mL, 0.72 mmol) in 1,2-dichloroethane (10 mL) with chloroacetyl chloride (0.06 mL, 30.72 mmol). Heat the solution to reflux for 2 h, cool to ambient temperature, and pour into an aqueous potassium carbonate solution. Extract the resulting mixture with $CH_2Cl_2$ and wash with saturated aq NaCl. Separate the organic layer, dry over $Na_2SO_4$, filter, and concentrate. Purify by preparative TLC (5% methanol in $CH_2Cl_2$) to obtain the title compound as a yellow solid.

C. [3-(2,4-dichlorophenyl)-2,5-dimethylimidazolo[5,4-b]pyridin-7-yl](2-chloroethyl)amine

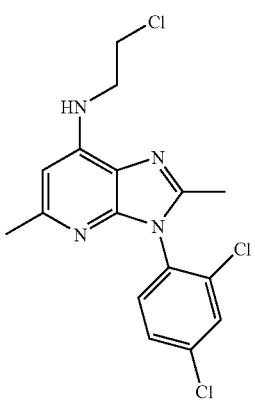

Treat a solution of N-[3-(2,4-dichlorophenyl)-2,5-dimethylimidazolo[5,4-b]pyridin-7-yl]-2-chloroacetamide (1.0 g, 2.6 mmol) in THF (5 mL) with borane-methyl sulfide complex (0.8 mL, 7.8 mmol). Heat the mixture to reflux for 3 h and quench at ambient temperature with a large excess of MeOH followed by 5 N HCl (2 mL). Re-heat the mixture to reflux for 1 h, then concentrate under reduced pressure. Purify by flash column chromatography (50% EtOAc-hexane) to obtain the title compound as a beige solid.

D. [3-(2,4-dichlorophenyl)-2,5-dimethylimidazolo[5,4-b]pyridin-7-yl][2-(cyclopentylamino)ethyl]amine

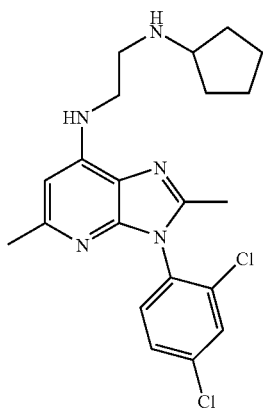

Heat a solution of [3-(2,4-dichlorophenyl)-2,5-dimethylimidazolo[5,4-b]pyridin-7-yl](2-chloroethyl)amine (0.08 g, 0.22 mmol), and cyclopentyl amine (0.2 mL g, 0.22 mmol) in dry NMP (3 mL) at 80° C. for 20 h. Pour the cooled mixture onto water (30 mL) and extract twice with EtOAc (50 mL). Wash the combined extracts with brine (50 mL), dry, and evaporate in vacuo. Purify by preparative TLC (10% MeOH in $CH_2Cl_2$) to obtain the title compound as a yellow oil.

Example 8

A. Ethyl 4-(2,6-dichlorophenyl)-2,4-dioxobutanoate

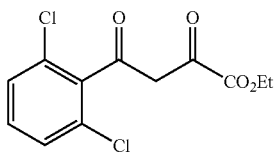

To a solution of 2',6'-dichloroacetophenone (12.5 g, 66 mmol) and diethyl oxalate (14.6 g, 100 mmol) in 450 mL of anhydrous toluene, cautiously add sodium hydride (60% dispersion in mineral oil, 2.8 g, 70 mmol). Cautiously heat the reaction mixture to reflux under $N_2$ for 1 h, cool to ambient temperature and pour onto ice-cold 1M HCl. Separate the layers and extract the aqueous phase with EtOAc (2×200 mL). Wash the combined organic extracts with brine, dry over $MgSO_4$ and evaporate to obtain the title compound which is used in the next step without further purification.

B. Ethyl 4-(2,6-dichlorophenyl)-3-(hydroxyimino)-2,4-dioxobutanoate

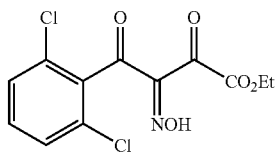

Slowly bubble $N_2O_3$ gas (generated by the dropwise addition of concentrated HCl into an aqueous solution of sodium nitrite) into a stirred solution of ethyl 4-(2,6-dichlorophenyl)-2,4-dioxobutanoate (14.4 g, 50 mmol) in EtOH (300 mL) until the reaction is complete (as determined by TLC). Remove the EtOH by evaporation under reduced pressure and partition the residue between EtOAc and water. Dry the organic extract over $MgSO_4$ and evaporate in vacuo to obtain the title compound which is used in the next step without further purification.

C. Ethyl 4-amino-5-(2,6-dichlorophenyl)-1-methylpyrazole-3-carboxylate

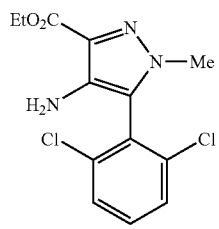

To a solution of ethyl 4-(2,6-dichlorophenyl)-3-(hydroxyimino)-2,4-dioxobutanoate (14 g, 44 mmol) in MeOH (400 mL) at 0° C., add dropwise-concentrated HCl (10 mL) followed by methyl hydrazine (2.02 g, 44 mmol). Stir the reaction mixture at ambient temperature for 8 h and concentrate in vacuo. Partition the residue between EtOAc (400 mL) and saturated aqueous $NaHCO_3$ (150 mL) and separate the layers. Add water (200 mL) to the organic layer, followed by sodium hydrosulfite (150 g) and stir the resulting mixture vigorously for 4 h. Separate the organic phase, wash with water (200 mL), brine (200 mL), dry over $MgSO_4$ and evaporate to obtain the title compound.

D. 3-(2,6-Dichlorophenyl)-2.5-dimethyl-6-hydropyrazolo[4,3-d]pyrimidin-7-one

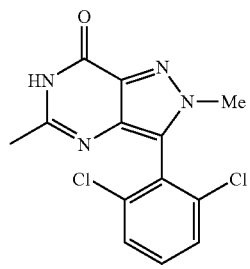

Saturate a solution of ethyl 4-amino-5-(2,6-dichlorophenyl)-1-methylpyrazole-3-carboxylate (6 g, 20 mmol) in acetonitrile (150 mL) with HCl gas, stir at ambient temperature for 14 h and then concentrate. Partition the residue partition between EtOAc (150 mL) and aqueous NaHCO₃ (150 mL) and separate the layers. Wash the organic layer with brine (100 mL), dry over MgSO₄ and concentrate. Triturate the residue with Et₂O, and collect the yellow solid by filtration to obtain the title compound.

E. 3-(2,6-Dichlorophenyl)-7-chloro-2,5-dimethylpyrazolo[4,3-d]pyrimidine

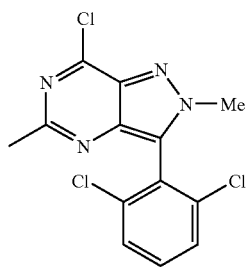

Heat a solution of 3-(2,6-dichlorophenyl)-2,5-dimethyl-6-hydropyrazolo[4,3-d]pyrimidin-7-one (3.09 g, 10 mmol), POCl₃ (35 mL) and N,N-dimethylaniline (1.44 g, 12 mmol) at 90° C. for 8 h. Remove the volatiles by evaporation, re-dissolve the residue in CH₂Cl₂ (100 mL) and wash with aqueous NaHCO₃ (2×50 mL). Dry the organic layer over MgSO₄ and concentrate under reduced pressure. Purify the residue by flash column chromatography (silica, eluent 50% Et₂O in hexane) to obtain the title compound.

F. (2-Aminoethyl)[3-(2,6-dichlorophenyl)-2,5-dimethylpyrazolo[3,4-e]pyrimidin-7-yl]amine

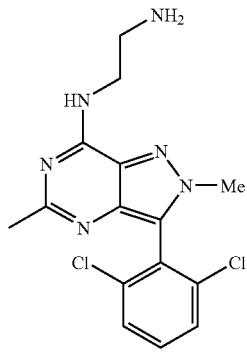

To a stirred solution of 3-(2,6-dichlorophenyl)-7-chloro-2,5-dimethylpyrazolo[4,3-d]pyrimidine (652 mg, 2.0 mmol) in acetonitrile (50 mL) at 50° C., add ethylene diamine (2.4 g, 40 mmol) in one portion. Maintain the reaction at 50° C. for 2 h, cool to ambient temperature and remove the volatiles by evaporation. Partition the residue between CH₂Cl₂ (50 mL) and 1N NaOH (50 mL) and extract the aqueous layer with CH₂Cl₂ (2×30 mL). Wash the combined organic extracts with water (30 mL), brine (30 mL), dry over MgSO₄ and evaporate to obtain the title compound.

G. [3-(2,6-Dichlorophenyl)-2,5-dimethylpyrazolo[3,4-e]pyrimidin-7-yl][2-cyclopentylamino)ethyl]amine

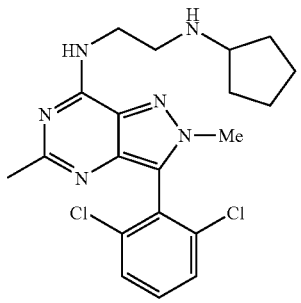

To (2-aminoethyl)[3-(2,6-dichlorophenyl)-2,5-dimethylpyrazolo[3,4-e]pyrimidin-7-yl]amine (140 mg, 0.4 mmol) in dichloroethane (5 mL), add cyclopentanone (34 mg, 0.4 mmol), sodium triacetoxyborohydride (106 mg, 0.5 mmol) and glacial acetic acid (24 mg, 0.4 mmol). Stir the reaction mixture at ambient temperature for 2 h and pour into 1N NaOH (10 mL). Separate the layers and extract the aqueous phase with CH₂Cl₂ (2×10 mL). Wash the combined organic extracts with water (10 mL), brine (10 mL), dry over MgSO₄ and evaporate in vacuo. Purify by preparative TLC (eluent 10% MeOH in chloroform) to obtain the title compound.

Example 9

A. N-(2-{[3-(2,6-Dichlorophenyl)-2,5-dimethylpyrazolo[3,4-e]pyrimidin-7-yl]amino}-2-(4-ethoxy-3-methoxyphenyl)acetamide

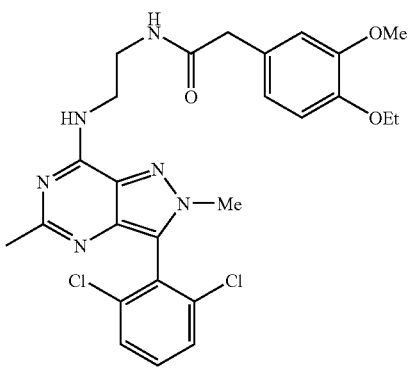

To a stirred solution of (2-aminoethyl)[3-(2,6-dichlorophenyl)-2,5-dimethylpyrazolo[3,4-e]pyrimidin-7-yl]amine (175 mg, 0.5 mmol) in N,N-dimethylacetamide (5 mL), add 4-methylmorpholine (101 mg, 1.0 mmol), 2-(4-ethoxy-3-methoxyphenyl)acetic acid (115 mg, 0.55 mmol) and bis(2-oxo-3-oxazolidinyl)phosphinic chloride (331 mg, 0.75 mmol). Stir the reaction mixture at ambient temperature for 14 h and dilute with EtOAc (15 mL). Wash the organic extracts successively with water (10 mL), brine (10 mL), saturated NH₄Cl (10 mL), 2N NaOH (10 mL), brine (10 mL), dry over MgSO₄ and evaporate under reduced pressure to obtain the title compound.

B. [3-(2,6-dichlorophenyl)-2,5-dimethylpyrazolo[3,4-e]pyrimidin-7-yl](2-{[2-(4-ethoxy-3-methoxyphenyl)ethyl]amino}ethyl)amine

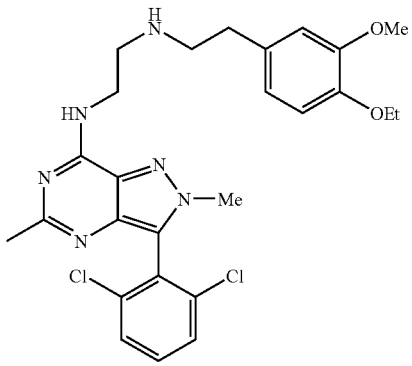

To a stirred solution of N-(2-{[3-(2,6-dichlorophenyl)-2,5-dimethylpyrazolo[3,4-e]pyrimidin-7-yl]amino}-2-(4-ethoxy-3-methoxyphenyl)acetamide (175 mg, 0.5 mmol) in THF (5 mL), add borane-dimethylsulfide complex (1M in THF, 0.25 mL, 2.5 mmol). Heat the reaction mixture to reflux for 14 h, cool to ambient temperature and quench by careful addition of MeOH (3 mL). Remove the volatile by evaporation and re-dissolve the residue in MeOH (5 mL). Add HCl in Et$_2$O (1M, 2 mL) and heat the solution to reflux for 1 h. Remove the volatiles by evaporation under reduced pressure, dissolve the residue in CH$_2$Cl$_2$ (20 mL) and wash with saturated NaHCO$_3$ (20 mL) and brine (10 mL). Dry the organic layer over MgSO$_4$ and concentrate in vacuo. Purify of the residue by preparative TLC (eluent 20% MeOH in chloroform) to obtain the title compound.

Example 10

A. [5-Methyl-3-(2,4,6-trimethylphenyl)(1,2,3-triazolino[5,4-b]pyridin-7-yl)]benzylamine

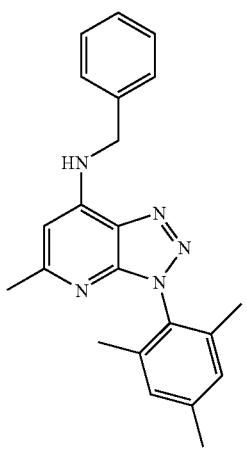

Treat a solution of 3-amino-6-methyl-4-[benzylamino](2-pyridyl)(2,4,6-trimethylphenyl)amine (1.70 g, 4.91 mmol) in THF (25 mL) with tetrafluoroboric acid (0.86 g, 9.81 mmol) at 0° C. Add dropwise isoamyl nitrite (0.86 g, 7.36 mmol) to the reaction mixture, stir at ambient temperature for 30 min, dilute with EtOAc (30 mL), wash with aq NaHCO$_3$ (40 mL), then with saturated aq NaCl (30 mL). Dry the organic layer over Na$_2$SO$_4$, filter, and concentrate in vacuo. Purify by flash column chromatography (50% ethyl acetate-hexane) to obtain the title compound as a solid.

B. 5-Methyl-3-(2,4,6-trimethylphenyl)-1,2,3-triazolino[5,4-b]pyridine-7-ylamine

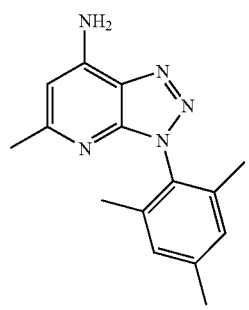

Add palladium hydroxide (0.5 g) to a solution of [5-methyl-3-(2,4,6-trimethylphenyl)(1,2,3-triazolino[5,4-b]pyridin-7-yl)]benzylamine (0.75 g, 2.10 mmol) in acetic acid (10 mL). Hydrogenate the mixture at a pressure of 50 psi for 17 h. Filter the mixture through celite, evaporate to dryness under reduced pressure, dilute with EtOAc and successively wash with aq NaHCO$_3$ and aq NaCl. Dry the organic layer over Na$_2$SO$_4$, filter, and concentrate in vacuo. Purify by flash column chromatography (3% MeOH in CH$_2$Cl$_2$) to obtain the title compound as a solid.

C. 2-Chloro-N-[5-methyl-3-(2,4,6-trimethylphenyl)(1,2,3-triazolino[5,4-b]pyridin-7-yl)]acetamide Treat a solution of 5-methyl-3-(2,4,6-trimethylphenyl)-1,2,3-triazolino[5,4-b]pyridine-7-ylamine (1.0 g, 3.74 mmol), and N,N-diisopropylethylamine, (0.7 mL, 4.11 mmol) in 1,2-dichloroethane (10 mL) with chloroacetyl chloride (0.33 mL, 4.11 mmol). Heat the solution to reflux for 3 h, cool to ambient temperature, and pour into an aqueous potassium carbonate solution. Extract the resulting mixture with CH$_2$Cl$_2$ and wash with saturated aq NaCl. Separate the organic layer, dry over Na$_2$SO$_4$, filter and concentrate. Purify by flash column chromatography (30% ethyl acetate-hexane)to obtain the title compound as a white crystalline solid.

D. (2-Chloroethyl)[5-methyl-3-(2,4,6-trimethylphenyl)(1,2,3-triazolino[5,4-b]pyridin-7-yl)]amine

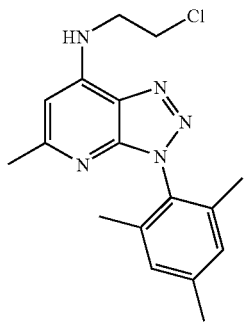

Treat a solution of 2-chloro-N-[5-methyl-3-(2,4,6-trimethylphenyl)(1,2,3-triazolino[5,4-b]pyridin-7-yl)]acetamide (0.80 g, 2.33 mmol) in THF (7 mL) with borane-methyl sulfide complex (0.7 mL, 7.0 mmol). Heat the mixture to reflux for 8 h and quench at ambient temperature with a large excess of methanol. Re-heat the mixture to reflux for 1 h, then concentrate under reduced pressure to obtain the title compound as a yellow solid.

E. (2-{[2-(4-Ethoxy-3-methoxyphenyl)ethyl]amino}ethyl)[5-methyl-3-(2,4,6-trimethylphenyl)(1,2,3-triazolino[5,4-b]pyridin-7-yl)]amine

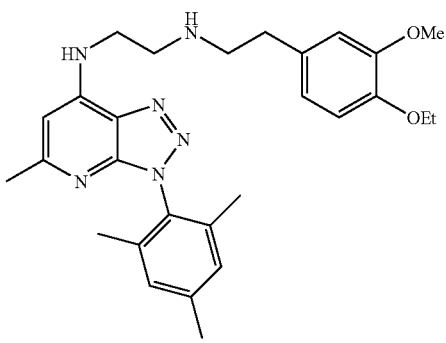

Heat a solution of (2-chloroethyl)[5-methyl-3-(2,4,6-trimethylphenyl)(1,2,3-triazolino[5,4-b]pyridin-7-yl)]amine (0.150 g, 0.45 mmol) and 4-ethoxy-3-methoxy phenethylamine (0.53 g, 2.73 mmol) in dry NMP (3 mL) at 80° C. for 14 h. Pour the cooled mixture onto water (50 mL) and extract twice with EtOAc (30 mL). Wash the combined extracts with brine (30 mL), dry, and evaporate in vacuo. Purify by flash column chromatography (10% MeOH in $CH_2Cl_{2-0.1}$% ammonium hydroxide) to obtain the title compound as a solid.

Example 11

A. [2-(Cyclopentylamino)ethyl][5-methyl-3-(2,4,6-trimethylphenyl)(1,2,3-triazolino[5,4-b]pyridin-7-yl)]amine

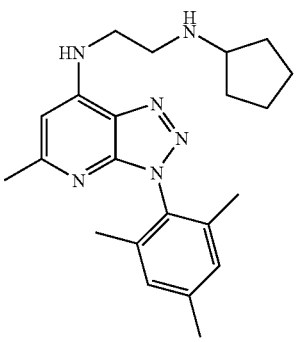

Heat a solution of (2-chloroethyl)[5-methyl-3-(2,4,6-trimethylphenyl)(1,2,3-triazolino[5,4-b]pyridin-7-yl)]amine (0.06 g, 0.18 mmol), and cyclopentyl amine (0.53 g, 1.82 mmol) in dry NMP (3 mL) at 80° C. for 14 h. Pour the cooled mixture onto water (30 mL) and extract twice with EtOAc (20 mL). Wash the combined extracts with brine (20 mL), dry, and evaporate in vacuo. Purify by flash column chromatography (10% methanol-$CH_2Cl_{2-0.1}$% ammonium hydroxide) to obtain the title compound as a solid.

Example 12

A. 4,6-Dichloro-2-methyl-5-amino-pyrimidine

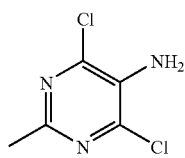

Add iron powder (6.0 g) to a solution of 4,6 dichloro-2-methyl-5-nitro-pyrimidine (6.50 g, 31 mmol) in acetic acid (11 mL) and MeOH (50 mL). Heat the resulting mixture at 65° C. for 1 h. After cooling, to ambient temperature, filter the mixture through a pad of celite, and evaporate the filtrate to dryness under reduced pressure. Treat the residue with 1N aq NaOH, and extract with EtOAc. Wash the EtOAc extract with water and saturated aq NaCl, dry over $Na_2SO_4$, filter, and concentrate in vacuo to obtain the title compound as a solid.

B. (5-Amino-6-chloro-2-methylpyrimidin-4-yl)[(2-bromo-4-isopropyl)phenyl]amine

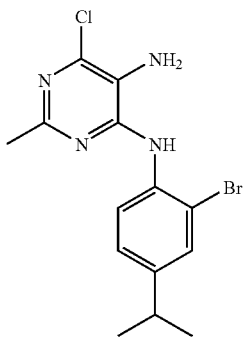

Heat a solution of 4,6-dichloro-2-methyl-5-amino-pyrimidine (2.0 g, 11.2 mmol) and 2-bromo-4-isopropylamine (2.4 g, 11.2 mmol) at 140° C. for 1 h. After cooling to ambient temperature, dilute the mixture with EtOAc (25 mL), and wash with 1N NaOH (50 mL) and saturated aq NaCl (20 mL). Dry the organic layer over $Na_2SO_4$, filter, and concentrate under reduced pressure to obtain the title compound as a dark oil which is used without further purification.

C. 9-[(2-Bromo-4-isopropyl)-phenyl]-6-chloro-2-methyl-7-hydropurin-8-one

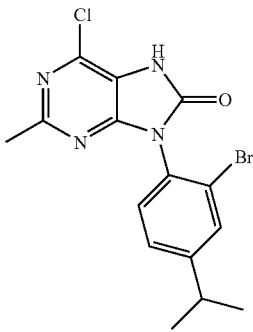

Treat a solution of (5-amino-6-chloro-2-methylpyrimidin-4-yl)[(2-bromo-4-isopropyl)phenyl]amine (1.0 g, 2.88 mmol) and triethyl amine (0.27 mL, 1.97 mmol) in THF (10 mL) with triphosgene (0.3 g, 0.98 mmol) and stir at ambient temperature for 14 h.

Quench the reaction mixture with water and dilute with EtOAc (20 mL). Separate the organic layer, wash with brine (20 mL), dry over $Na_2SO_4$, filter, and concentrate under reduced pressure. Purify by flash column chromatography (50% EtOAc-hexane) to obtain the title compound as a dark brown solid.

D. 6-[(2-Aminoethyl)amino]-9-[(2-bromo-4-isopropyl)phenyl]-2-methyl-7-hydropurin-8-one

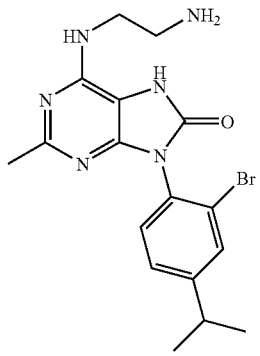

Heat a solution of 9-[(2-bromo-4-isopropyl)-phenyl]-6-chloro-2-methyl-7-hydropurin-8-one. (0.34 g, 0.89 mmol), and ethylenediamine (0.32 g, 5.37 mmol) in dry NMP (2 mL) at 85° C. for 14 h. Pour the cooled mixture onto water (50 mL) and extract twice with EtOAc (30 mL). Wash the combined extracts with brine (30 mL), dry, and evaporate in vacuo to obtain the title compound which is used without further purification.

E. 9-[(2-Bromo-4-isopropyl)phenyl]-6-{[2-(cyclohexylamino)ethyl]amino}-2-methyl-7-hydropurin-8-one

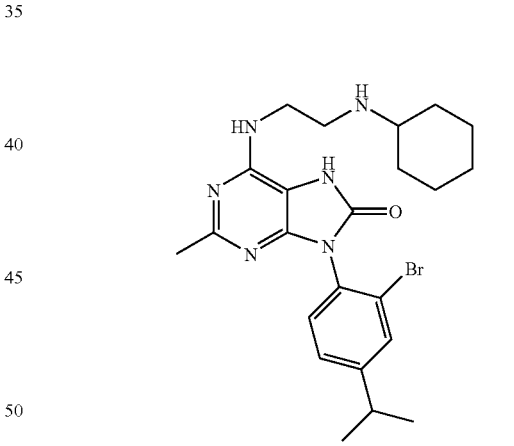

Treat a solution of 6-[(2-aminoethyl)amino]-9-[(2-bromo-4-isopropyl)phenyl]-2-methyl-7-hydropurin-8-one (0.100 g, 0.248 mmol), cyclohexanone (0.03 mL, 0.248 mmol) and acetic acid (0.01 mL, 0.248 mmol) in dry dichloroethane (3 mL) with sodium triacetoxyborohydride (0.07 g, 0.347 mmol) and stir at ambient temperature for 10 h. Dilute the resulting mixture with $CH_2Cl_2$ (20 mL) and wash with saturated aq NaCl (50 mL). Dry the organic phase over $Na_2SO_4$, filter, and concentrate under reduced pressure. Purify by preparative TLC (10% methanol in $CH_2Cl_2$ with 0.5% ammonium hydroxide) to obtain the title compound as a yellow solid.

Example 13

A. (2-Aminoethyl)[2-methyl-8-(2,4,6-trimethylphenyl)(4-quinolyl)]amine

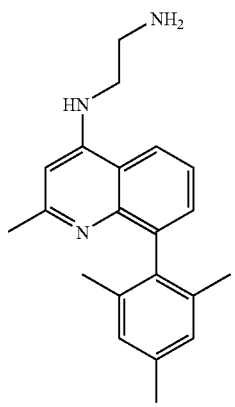

In a sealed tube, heat 4-bromo-2-methyl-8-(2,4,6-trimethyl-phenyl)-quinoline (100 mg, 0.29 mmol) at 140° C. in a mixture of ethylene glycol (1 mL) and ethylene diamine (0.3 mL). After 4 h, cool the reaction mixture and partition between saturated aqueous NaHCO$_3$ and chloroform. Dry the combined organic extracts on Na$_2$SO$_4$ and concentrate under reduced pressure to obtain the title compound as a yellow glass: +APcI MS (M+1)$^+$ 320; $^1$H NMR (methanol-d$_4$) δ: 7.78 (dd, 1H), 7.39 (t, 1H), 7.34 (dd, 1H), 6.95 (s, 2H), 6.31 (s, 1H), 3.34 (t, 2H), 3.11 (t, 2H), 2.43 (s, 3H), 2.34 (s, 3H), 1.89 (s, 6H).

B. [2-Methyl-8-(2,4,6-trimethylphenyl)(4-quinolyl)][2-(2-1,2,3,4-tetrahydronaphthylamino)ethyl]amine hydrochloride

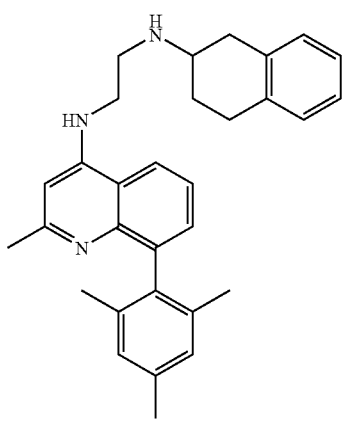

To a stirred solution of (2-aminoethyl)[2-methyl-8-(2,4,6-trimethylphenyl)(4-quinolyl)]amine (21 mg, 0.066 mmol) and 1,2,3,4-tetrahydro-2-naphthalenone (42 mg, 0.29 mmol) in MeOH (1 mL)/acetic acid (0.01 mL), add sodium cyanoborohydride (4 mg, 0.3 mmol). After stirring 4 h, concentrate the reaction mixture under reduced pressure and partition between saturated aqueous NaHCO$_3$ and chloroform. Dry the combined organic extracts on Na$_2$SO$_4$, concentrate under reduced pressure, and purify by column chromatography on silica gel (eluent: 32:1 EtOAc/triethylamine) to obtain the title compound as a colorless glass. Treat a methanolic solution of the product with concentrated aqueous hydrochloric acid to generate the hydrochloride salt. Concentrate the solution under reduced pressure and triturate the residue in Et$_2$O to obtain the title compound as a colorless solid: +APcI MS (M+1)$^+$ 450; $^1$H NMR (methanol-d$_4$) δ: 8.52 (dd, 1H), 7.78 (t, 1H), 7.62 (dd, 1H), 7.15–7.00 (m, 7H), 4.06 (t, 2H), 2.66 (s, 3H), 2.38 (s, 3H), 1.87 (s, 6H).

Example 14

A. 2-(3,4-Dimethoxyphenyl)-N-(2-{[3,6-dimethyl-2-(2,4,6-trimethylphenoxy)(4-pyridyl)]amino}ethyl)acetamide

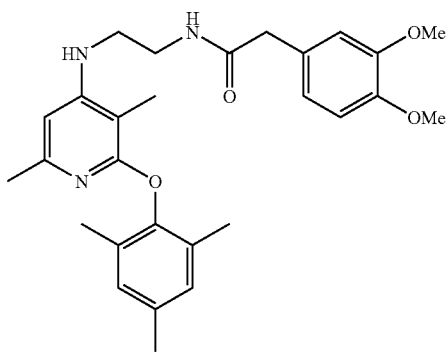

Stir a solution of [3,6-dimethyl-2-(2,4,6-trimethyl-phenoxy)-4-pyridyl][2-(methylamino)ethyl]amine (68 mg, 0.23 mmol), 3,4-dimethoxyphenylacetic acid (59 mg, 0.3 mmol), EDC (59 mg, 0.3 mmol) and HOBT (41 mg, 0.3 mmol) in DMF (1.0 mL) for 12 h. Dilute the reaction mixture with EtOAc (10 mL) and wash with saturated aq NaHCO$_3$ (2×10 mL) and saturated aq brine (2×10 mL), dry and concentrate in vacuo to obtain the title compound as an oily residue. M+1: 478.

B. (2-{[2-(3,4-Dimethoxyphenyl)ethyl]amino}ethyl)[3,6-dimethyl-2-(2,4,6-trimethylphenoxy)(4-pyridyl)]amine

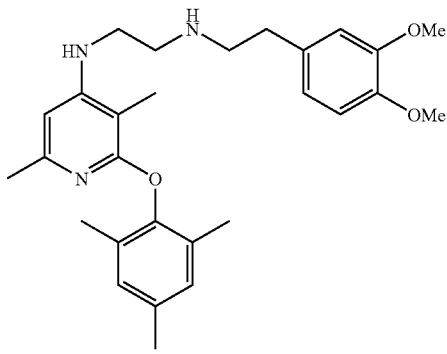

Add BH$_3$ in THF (1 M solution, 0.3 mmol, 0.3 mL) to a solution of the crude 2-(3,4-dimethoxyphenyl)-N-(2-{[3,6-dimethyl-2-(2,4,6-trimethylphenoxy)(4-pyridyl)]amino}ethyl) acetamide in THF (2.0 mL) at ambient temperature. Heat the reaction mixture under reflux for 15 h, dilute with a solution of 10% aq HCV/MeOH (1:1, 2 mL) and heat again under reflux (1 h). Dilute the reaction mixture with CHCl$_3$ (10 mL), wash with saturated aq NaHCO$_3$ (1×5 mL), dry and concentrate in vacuo. Chromatograph the crude residue on SiO$_2$-gel using a gradient of 100% EtOAc to 10% Et$_2$NH/EtOAc to obtain the title compound as a colorless oil. Immediately dissolve the product in Et$_2$O (1 mL), treat with excess 4 M HCl/dioxane and concentrate in vacuo to obtain the hydrochloride salt of the title compound as a colorless solid. $^1$H NMR (d$_4$-MeOH, Unity 400): d 6.99–6.77 (6H, m), 3.81 (3H, s), 3.78 (3H, s), 3.62 (2H, m), 2.98 (2H, t), 2.39 (3H, s), 2.29 (3H, s), 2.16 (3H, s), 2.07 (6H, s). M+1: 464.

Example 15

A. (2-Aminoethyl){2-methyl-6-[(2,4,6-trimethylphenyl)amino]pyrimidin-4-yl}amine

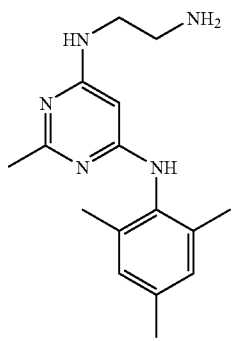

Heat a solution of 6-chloro-2-methyl-pyrimidin-4-yl)-(2,4,6-trimethyl-phenyl)-amine (0.50 g, 1.91 mmol), and ethylenediamine (1.28 mL, 19.10 mmol) in dry NMP (5 mL) at 100° C. for 14 h. Pour the cooled mixture onto water (50 mL) and extract twice with EtOAc (30 mL). Wash the combined extracts with brine (30 mL), dry, and evaporate in vacuo. Purify by preparative TLC (10% methanol-CH$_2$Cl$_2$–0.5% ammonium hydroxide) to obtain the title compound.

B. 2-(4-Ethoxy-3-methoxy-phenyl)-N-{2-[2-methyl-6-(2,4,6-trimethyl-phenylamino)-pyrimidin-4-ylamino]ethyl}-acetamide

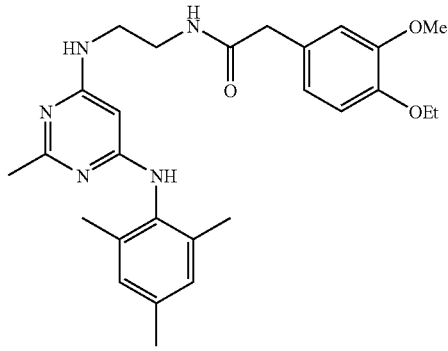

To a solution of (2-aminoethyl){2-methyl-6-[(2,4,6-trimethylphenyl)amino]pyrimidin-4-yl}amine (0.36 g, 1.26 mmol), 4-ethoxy-3-methoxyphenethylamine (0.26 g, 1.26 mmol)) and N,N diisopropylethyl amine (0.24 ml, 1.38 mmol in CH$_2$Cl$_2$ (5 mL), add benzotriazol-1-yloxytris-(dimethylamino)phosphonium hexafluorophosphate (0.61 g, 1.38 mmol) and stir at ambient temperature for 14 h. Dilute the resulting mixture with CH$_2$Cl$_2$ (20 mL), and wash with water (20 mL) and saturated aq NaCl (20 mL). Dry the organic layer over Na$_2$SO$_4$, filter and concentrate in vacuo. Purify by preparative TLC (7% methanol-CH$_2$Cl$_2$) to obtain the title compound.

C. (2-{[2-(4-Ethoxy-3-methoxyphenyl)ethyl]amino}ethyl){2-methyl-6-[(2,4,6-trimethylphenyl)amino]pyrimidin-4-yl}amine

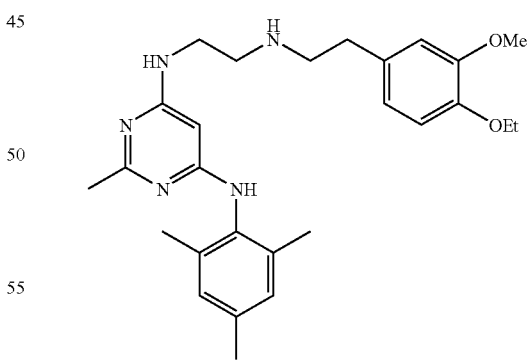

Heat a solution of 2-(4-ethoxy-3-methoxy-phenyl)-N-{2-[2-methyl-6-(2,4,6-trimethyl-phenylamino)-pyrimidin-4-ylamino]ethyl}-acetamide (0.324 g, 0.68 mmol) in THF (10 mL) with AlH$_3$.NMe$_2$Et (14 mL, 6.78 mmol) to reflux for 14 h. Cool the resulting mixture to ambient temperature, quench with Na$_2$CO$_3$.10H$_2$O (1.0 g) and stir at ambient temperature for 15 min. Filter the solution through Celite and wash with several portions of CH$_2$Cl$_2$. Concentrate the filtrate in vacuo to dryness and purify by preparative TLC (10% MeOH in CH$_2$Cl$_2$) to obtain the title compound.

The preparation of the compounds of the present invention by the above-mentioned methods is illustrated further by the following examples, delineated in the TABLE which are not to be construed as limiting the invention in scope or spirit to the specific procedures and compounds described in them. Commonly used abbreviations are: Ph is phenyl, Me is methyl, Et is ethyl, Pr is n-propyl, iPr is isopropyl, cPr is cyclopropyl, Bu is butyl, iBu is isobutyl (CH$_2$—CHMe$_2$), tBu is tert-butyl, cBu is cyclobutyl, Pent is n-pentyl, cPent is cyclopentyl, cHex is cyclohexyl, Py is pyridyl, Bn is benzyl (CH$_2$Ph), Ac is acetyl (CH$_3$—(C=O)), tBOC is tert-butyloxycarbonyl (tBuO—(C=O)). EX means example.

TABLE 1

Tables of Examples

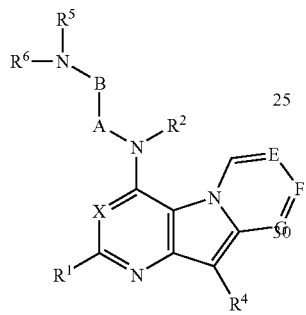

| EX | X | R1 | R2 | E | F | G | R4 | A—B—N[R$^6$]—R$^5$ |
|---|---|---|---|---|---|---|---|---|
| 16. | CH | Me | H | CH | CH | CH | 2,6-diMe-4-OMe—Ph | (CH2)2—NH—(CH2)2—(3,4-diOMe—Ph) |
| 17. | CH | Me | H | CH | CH | CH | 2,4,6-triMe—Ph | (CH2)2—NH—(CH2)2—(3,4-diOMe—Ph) |
| 18. | CH | Me | H | CH | CH | CH | 2,4,6-triMe—Ph | (CH2)2—NH—(CH2)2—(4-OCF3—Ph) |
| 19. | CH | Me | H | CH | CH | CH | 2,4,6-triMe—Ph | (CH2)2—NH-cPent |
| 20. | CH | Me | H | CH | CH | CH | 2,4,6-triMe—Ph | (CH2)2—NH-cHex |
| 21. | CH | Me | H | CH | CH | CH | 2,4,6-triMe—Ph | (CH2)2—NH-(4-OH-cHex) |
| 22. | CH | Me | H | CH | CH | CH | 2,4,6-triMe—Ph | (CH2)2—NH-(tetrahydropyran-4-yl) |
| 23. | CH | Me | H | CH | CH | CH | 2,4,6-triMe—Ph | (CH2)2—NH-(1-(pyrimidin-2-yl)-piperidin-4-yl) |
| 24. | CH | Me | H | CH | CH | CH | 2,6-diCl-4-OMe—Ph | (CH2)2—NH-cPent |
| 25. | CH | Me | H | CH | CH | CH | 2,6-diCl-4-OMe—Ph | (CH2)2—NH-cHex |
| 26. | CH | Me | H | CH | CH | CH | 2,6-diCl-4-OMe—Ph | (CH2)2—NH-(4-OH-cHex) |
| 27. | CH | Me | H | CH | CH | CH | 2,6-diCl-4-OMe—Ph | (CH2)2—NH-(tetrahydropyran-4-yl) |
| 28. | CH | Me | H | CH | CH | CH | 2,6-diCl-4-OMe—Ph | (CH2)2—NH-(1-(pyrimidin-2-yl)-piperidin-4-yl) |
| 29. | CH | Me | H | CH | CH | CH | 2,6-diCl-4-OMe—Ph | (CH2)2—NH—(CH2)2—(3-OMe-4-EtO—Ph) |
| 30. | N | Me | H | CH | CH | CH | 2,4,6-triMe—Ph | (CH2)2—N(cPent)2 |
| 31. | N | Me | H | CH | CH | CH | 2,4,6-triMe—Ph | (CH2)2—NH—(CH2)2—(3,4-diOMe—Ph) |
| 32. | N | Me | H | CH | CH | CH | 2,4,6-triMe—Ph | (CH2)2—NH—(CH2)2—(3-OMe-4-EtO—Ph) |
| 33. | N | Me | H | CH | CH | CH | 2,4,6-triMe—Ph | (CH2)2—NH-cHex |
| 34. | N | Me | H | CH | CH | CH | 2,4,6-triMe—Ph | (CH2)2—NH-(4-OH-cHex) |
| 35. | N | Me | H | CH | CH | CH | 2,4,6-triMe—Ph | (CH2)2—NH-(tetrahydropyran-4-yl) |
| 36. | N | Me | H | CH | CH | CH | 2,4,6-triMe—Ph | (CH2)2—NH-(1-(pyrimidin-2-yl)-piperidin-4-yl) |
| 37. | N | Me | H | CH | CH | CH | 2,6-diCl-4-OMe—Ph | (CH2)2—NH-cPent |
| 38. | N | Me | H | CH | CH | CH | 2,6-diCl-4-OMe—Ph | (CH2)2—NH-cHex |
| 39. | N | Me | H | CH | CH | CH | 2,6-diCl-4-OMe—Ph | (CH2)2—NH-(4-OH-cHex) |
| 40. | N | Me | H | CH | CH | CH | 2,6-diCl-4-OMe—Ph | (CH2)2—NH-(tetrahydropyran-4-yl) |
| 41. | N | Me | H | CH | CH | CH | 2,6-diCl-4-OMe—Ph | (CH2)2—NH-(1-(pyrimidin-2-yl)-piperidin-4-yl) |
| 42. | N | Me | H | CH | CH | CH | 2,6-diCl-4-OMe—Ph | (CH2)2—NH—(CH2)2—(3-OMe-4-EtO—Ph) |
| 43. | N | Me | H | CH | CH | CH | 2,6-diCl-4-OEt—Ph | (CH2)2—NH-cPent |
| 44. | N | Me | H | CH | CH | CH | 2,6-diCl-4-OEt—Ph | (CH2)2—NH-cHex |
| 45. | N | Me | H | CH | CH | CH | 2,6-diCl-4-OEt—Ph | (CH2)2—NH-(4-OH-cHex) |
| 46. | N | Me | H | CH | CH | CH | 2,6-diCl-4-OEt—Ph | (CH2)2—NH-(tetrahydropyran-4-yl) |
| 47. | N | Me | H | CH | CH | CH | 2,6-diCl-4-OEt—Ph | (CH2)2—NH-(1-(pyrimidin-2-yl)-piperidin-4-yl) |
| 48. | N | Me | H | CH | CH | CH | 2,6-diCl-4-OEt—Ph | (CH2)2—NH—(CH2)2—(3-OMe-4-EtO—Ph) |

TABLE 2

| EX | X | R1 | R2 | R3 | R16 | R4 |
|---|---|---|---|---|---|---|
| 49. | CH | Me | H | Me | H | 2,4,6-triMe—Ph |
| 50. | CH | Me | H | Me | H | 2,4,6-triMe—Ph |
| 51. | CH | Me | H | Me | H | 2,4,6-triMe—Ph |
| 52. | CH | Me | H | Me | H | 2,4;6-triMe—Ph |
| 53. | CH | Me | H | Me | H | 2,4,6-triMe—Ph |
| 54. | CH | Me | H | Me | H | 2,4,6-triMe—Ph |
| 55. | CH | Me | H | Me | H | 2,4,6-triMe—Ph |
| 56. | CH | Me | H | Me | H | 2,6-diCl-4-OMe—Ph |
| 57. | CH | Me | H | Me | H | 2,6-diCl-4-OMe—Ph |
| 58. | CH | Me | H | Me | H | 2,6-diCl-4-OMe—Ph |
| 59. | CH | Me | H | Me | H | 2,6-diCl-4-OMe—Ph |
| 60. | CH | Me | H | Me | H | 2,6-diCl-4-OMe—Ph |
| 61. | CH | Me | H | Me | H | 2,6-diCl-4-OEt—Ph |
| 62. | CH | Me | H | Me | H | 2,6-diCl-4-OEt—Ph |
| 63. | CH | Me | H | Me | H | 2,6-diCl-4-OEt—Ph |
| 64. | CH | Me | H | Me | H | 2,6-diCl-4-OEt—Ph |
| 65. | CH | Me | H | Me | H | 2,6-diCl-4-OEt—Ph |
| 66. | N | Me | H | Me | H | 2,4,-diMe-4-Br—Ph |
| 67. | N | Me | H | Me | Me | 2,4,6-triMe—Ph |
| 68. | N | Me | H | Me | H | 2,4,6-triMe—Ph |
| 69. | N | Me | H | Me | Me | 2,4,6-triMe—Ph |
| 70. | N | Me | H | Me | H | 2,4,6-triMe—Ph |
| 71. | N | Me | H | Me | H | 2,4,6-triMe—Ph |

TABLE 3

| EX | X | W | R1 | R2 | R3 | R4 | A—B—N[R$^6$]—R$^5$ |
|---|---|---|---|---|---|---|---|
| 72. | N | NMe | Me | H | H | 2,4,6-triMe—Ph | (CH2)2—NH—(CH2)2—(4-OMe—Ph) |
| 73. | N | NMe | Me | H | H | 2,4,6-triMe—Ph | (CH2)2—NH-cPent |
| 74. | N | NMe | Me | H | H | 2,4,6-triMe—Ph | (CH2)2—NH-cHex |
| 75. | N | NMe | Me | H | H | 2,4,6-triMe—Ph | (CH2)2—NH-(4-OH-cHex) |
| 76. | N | NMe | Me | H | H | 2,4,6-triMe—Ph | (CH2)2—NH-(tetrahydropyran-4-yl) |
| 77. | N | NMe | Me | H | H | 2,4,6-triMe—Ph | (CH2)2—NH-(1-(pyrimidin-2-yl)-piperidin-4-yl) |
| 78. | N | NMe | Me | H | H | 2,4,6-triMe—Ph | (CH2)2—NH—(CH2)2—(3-OMe-4-EtO—Ph) |
| 79. | N | S | Me | H | H | 2,4,6-triMe—Ph | (CH2)2—NH—(CH2)2—(4-OMe—Ph) |
| 80. | N | S | Me | H | H | 2,4,6-triMe—Ph | (CH2)2—NH-cPent |
| 81. | N | S | Me | H | H | 2,4,6-triMe—Ph | (CH2)2—NH-cHex |
| 82. | N | S | Me | H | H | 2,4,6-triMe—Ph | (CH2)2—NH-(4-OH-cHex) |
| 83. | N | S | Me | H | H | 2,4,6-triMe—Ph | (CH2)2—NH-(tetrahydropyran-4-yl) |
| 84. | N | S | Me | H | H | 2,4,6-triMe—Ph | (CH2)2—NH-(1-(pyrimidin-2-yl)-piperidin-4-yl) |
| 85. | N | S | Me | H | H | 2,4,6-triMe—Ph | (CH2)2—NH—(CH2)2—(3-OMe-4-EtO—Ph) |

TABLE 4

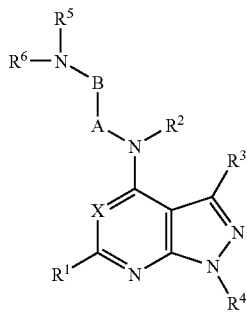

| # EX | X | R1 | R2 | R3 | R4 |
|---|---|---|---|---|---|
| 86. | N | Me | H | H | 2,4,6-triMe—Ph |
| 87. | N | Me | H | H | 2,4,6-triMe—Ph |
| 88. | N | Me | H | H | 2,4,6-triMe—Ph |
| 89. | N | Me | H | H | 2,4,6-triMe—Ph |
| 90. | N | Me | H | H | 2,4,6-triMe—Ph |

TABLE 4-continued

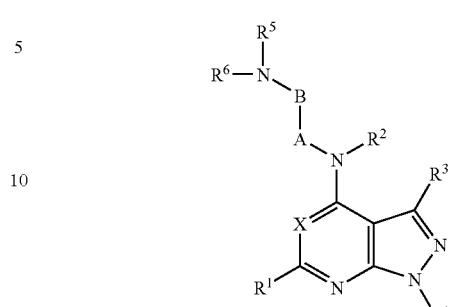

| # EX | X | R1 | R2 | R3 | R4 |
|---|---|---|---|---|---|
| 91. | N | Me | H | H | 2,4,6-triMe—Ph |
| 92. | N | Me | H | H | 2,4,6-triMe—Ph |

TABLE 5

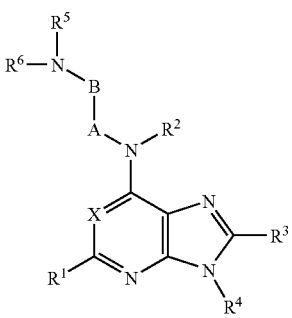

$R^1$ is methyl

| EX | X | R2 | R3 | R4 | A—B—N[$R^6$]—$R^5$ |
|---|---|---|---|---|---|
| 93. | CH | H | Me | 2,4,-diCl—Ph | (CH2)2—NH—(CH2)2—(2-OiPr-5-pyridyl) |
| 94. | CH | H | Me | 2,4,-diCl—Ph | (CH2)2—NH-cHex |
| 95. | CH | H | Me | 2,4-diCl—Ph | (CH2)2—NH—(CH2)2—((3-OMe-4-OiPr)-Ph) |
| 96. | CH | H | Me | 2,4,6-triMe-3-Py | (CH2)2—NH—(CH2)2—(3-OMe-4-iPrO—Ph) |
| 97. | CH | H | Me | 2,4,6-triMe—Ph | (CH2)2—NH-cBu |
| 98. | CH | H | Me | 2,4,6-triMe—Ph | (CH2)2—NH-cPent |
| 99. | CH | H | Me | 2,4,6-triMe—Ph | (CH2)2—NH-(4-OH-cHex) |
| 100. | CH | H | Me | 2,4,6-triMe—Ph | (CH2)2—NH-(tetahydropyran-4-yl) |
| 101. | CH | H | Me | 2,4,6-triMe—Ph | (CH2)2—NH-(1-pyrimidin-2-yl)-pipendin-4-yl) |
| 102. | CH | H | Me | 2,4,6-triMe—Ph | (CH2)2—NH—(CH2)2—(2-OiPr-5-pyridyl) |
| 103. | CH | H | Me | 2,4,6-triMe—Ph | (CH2)2—NH—(CH2)2—(3-OMe-4-EtO—Ph) |
| 104. | CH | H | Me | 2,4,6-triMe—Ph | (CH2)2—NH—(CH2)2—(3-OMe-4-iPrO—Ph) |
| 105. | CH | H | Me | 2,6-diCl-4-OMe—Ph | (CH2)2—NH-cPent |
| 106. | CH | H | Me | 2,6-diCl-4-OMe—Ph | (CH2)2—NH-cHex |
| 107. | CH | H | Me | 2,6-diCl-4-OMe—Ph | (CH2)2—NH-(4-OH-cHex) |
| 108. | CH | H | Me | 2,6-diCl-4-OMe—Ph | (CH2)2—NH-(tetrahydropyran-4-yl) |
| 109. | CH | H | Me | 2,6-diCl-4-OMe—Ph | (CH2)2—NH-(1-(pyrimidin-2-yl)-piperidin-4-yl) |
| 110. | CH | H | Me | 2,6-diCl-4-OMe—Ph | (CH2)2—NH—(CH2)2—(3-OMe-4-EtO—Ph) |
| 111. | N | H | Me | 2-Br-4-iPr—Ph | (CH2)2—NH-cPent |
| 112. | N | H | Cl | 2,4,6-triMe—Ph | (CH2)2—NH-cPent |
| 113. | N | H | Me | 2,4,6-triMe—Ph | (CH2)2—NH-cPent |
| 114. | N | H | Me | 2,4,6-triMe—Ph | (CH2)2—NH-cHex |
| 115. | N | H | Me | 2,4,6-triMe—Ph | (CH2)2—NH-(4-OH-cHex) |
| 116. | N | H | Me | 2,4,6-triMe—Ph | (CH2)2—NH-(tetrahydropyran-4-yl) |
| 117. | N | H | Me | 2,4,6-triMe—Ph | (CH2)2—NH-(1-(pyrimidin-2-yl)-piperidin-4-yl) |

TABLE 5-continued

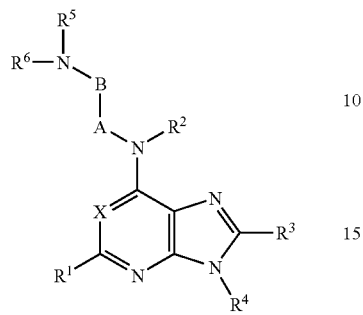

R¹ is methyl

| EX | X | R2 | R3 | R4 | A—B—N[R⁶]—R⁵ |
|---|---|---|---|---|---|
| 118. | N | H | Me | 2,4,6-triMe—Ph | (CH2)2—NH—(CH2)2—(3-OMe-4-EtO—Ph) |
| 119. | N | H | Me | 2,4,6-triMe—Ph | (CH2)2—NH—(CH2)2—(3-OMe-4-iPrO—Ph) |
| 120. | N | H | Cl | 2,4,6-triMe—Ph | (CH2)2-NH-cPent |
| 121. | N | H | Cl | 2,4,6-triMe—Ph | (CH2)2—NH—(CH2)2—(3-OMe-4-EtO—Ph) |
| 122. | N | H | Me | 2,6-diCl-4-OMe—Ph | (CH2)2—NH-cPent |
| 123. | N | H | Me | 2,6-diCl-4-OMe—Ph | (CH2)2—NH-cHex |
| 124. | N | N | Me | 2,6-diCl-4-OMe—Ph | (CH2)2—NH-(4-OH-cHex) |
| 125. | N | H | Me | 2,6-diCl-4-OMe—Ph | (CH2)2—NH-(tetahydropyran-4-yl) |
| 126. | N | H | Me | 2,6-diCl-4-OMe—Ph | (CH2)2—NH—(CH2)2—(3-OMe-4-EtO—Ph) |

TABLE 6

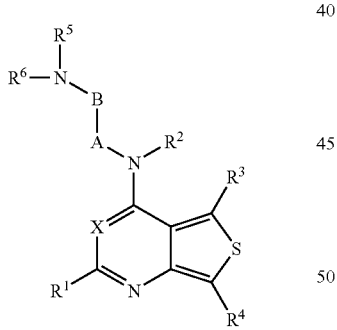

R¹ is mrthyl

| EX | X1 | R2 | R3 | R4 | A—B—N[R⁶]—R⁵ |
|---|---|---|---|---|---|
| 127. | CH | H | Me | 2,4,6-triMe—Ph | (CH2)2—NH-cPent |
| 128. | CH | H | Me | 2,4,6-triMe—Ph | (CH2)2—NH-cHex |
| 129. | CH | H | Me | 2,4,6-triMe—Ph | (CH2)2—NH-(4-OH-cHex) |
| 130. | CH | H | Me | 2,4,6-triMe—Ph | (CH2)2—NH-(tetrahydropyran-4-yl) |
| 131. | CH | H | Me | 2,4,6-triMe—Ph | (CH2)2—NH-(1-(pyrimidin-2-yl)-piperidin-4-yl) |
| 132. | CH | H | Me | 2,4,6-triMe—Ph | (CH2)2—NH—(CH2)2—(3-OMe-4-EtO—Ph) |

TABLE 7

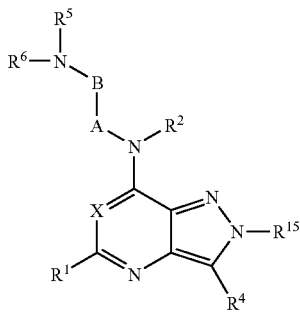

| EX | X | R1 | R2 | R15 |
|---|---|---|---|---|
| 133. | N | Me | H | Me |
| 134. | N | Me | H | Me |
| 135. | N | Me | H | Me |
| 136. | N | Me | H | Me |
| 137. | N | Me | H | Me |
| 138. | N | Me | H | Me |
| 139. | N | Me | H | Me |
| 140. | N | Me | H | Me |
| 141. | N | Me | H | Me |
| 142. | N | Me | H | Me |

TABLE 7-continued

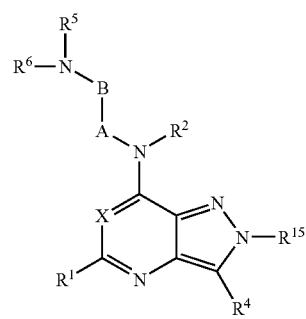

| EX | X | R1 | R2 | R15 |
|---|---|---|---|---|
| 143. | N | Me | H | Me |
| 144. | N | Me | H | Me |
| 145. | N | Me | H | Me |
| 146. | N | Me | H | Me |
| 147. | N | Me | H | Me |
| 148. | N | Me | H | Me |
| 149. | N | Me | H | Me |

TABLE 8

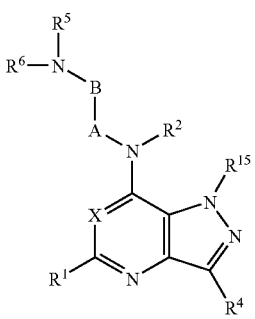

| EX | X | R1 | R2 | R15 | R4 | A—B—N[R6]—R5 |
|---|---|---|---|---|---|---|
| 150. | N | Me | H | Me | 2,4,6-triMe—Ph | (CH2)2—NH-cPent |
| 151. | N | Me | H | Me | 2,4,6-triMe—Ph | (CH2)2—NH-cHex |
| 152. | N | Me | H | Me | 2,4,6-triMe—Ph | (CH2)2—NH-(4-OH-cHex) |
| 153. | N | Me | H | Me | 2,4,6-triMe—Ph | (CH2)2—NH-(tetrahydropyran-4-yl) |
| 154. | N | Me | H | Me | 2,4,6-triMe—Ph | (CH2)2—NH-(1-(pyrimidin-2-yl)-piperidin-4-yl) |
| 155. | N | Me | H | Me | 2,4,6-triMe—Ph | (CH2)2—NH—(CH2)2—(3-OMe-4-EtO—Ph) |
| 156. | N | Me | H | Me | 2,6-diCl-4-OMe—Ph | (CH2)2—NH-cPent |
| 157. | N | Me | H | Me | 2,6-diCl-4-OMe—Ph | (CH2)2—NH-cHex |
| 158. | N | Me | H | Me | 2,6-diCl-4-OMe—Ph | (CH2)2—NH-(4-OH-cHex) |
| 159. | N | Me | H | Me | 2,6-diCl-4-OMe—Ph | (CH2)2—NH-(tetahydropyran-4-yl) |
| 160. | N | Me | H | Me | 2,6-diCl-4-OMe—Ph | (CH2)2—NH-(1-(pyrimidin-2-yl)-piperidin-4-yl) |
| 161. | N | Me | H | Me | 2,6-diCl-4-OMe—Ph | (CH2)2—NH—(CH2)2—(3-OMe-4-EtO—Ph) |

TABLE 9

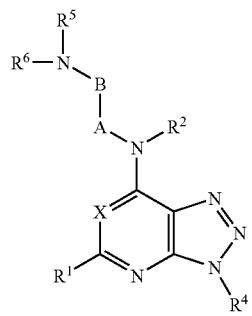

| EX | X | R1 | R2 | R4 | A—B—N[R6]—R5 |
|---|---|---|---|---|---|
| 162. | CH | Me | H | 2,4,6-triMe—Ph | (CH2)2—NH—(CH2)2-(3-OMe-4-iPrO—Ph) |
| 163. | CH | Me | H | 2,4,6-triMe—Ph | (CH2)2—NH-cBu |
| 164. | CH | Me | H | 2,4,6-triMe—Ph | (CH2)2—NH-cHex |
| 165. | CH | Me | H | 2,4,6-triMe—Ph | (CH2)2—NH-(4-OH-cHex) |
| 166. | CH | Me | H | 2,4,6-triMe—Ph | (CH2)2—NH-(tetrahydropyran-4-yl) |
| 167. | CH | Me | H | 2,4,6-triMe—Ph | (CH2)2—NH-(1-(pyrimidin-2-yl)-piperidin-4-yl) |
| 168. | CH | Me | H | 2,4,6-triMe—Ph | (CH2)2—NH—(CH2)2—(3-OMe-4-EtO—Ph) |
| 169. | CH | Me | H | 2,6-diCl-4-OMe—Ph | (CH2)2—NH-cPent |
| 170. | CH | Me | H | 2,6-diCl-4-OMe—Ph | (CH2)2—NH-cHex |
| 171. | CH | Me | H | 2,6-diCl-4-OMe—Ph | (CH2)2—NH-(4-OH-cHex) |
| 172. | CH | Me | H | 2,6-diCl-4-OMe—Ph | (CH2)2—NH-(tetrahydropyran-4-yl) |
| 173. | CH | Me | H | 2,6-diCl-4-OMe—Ph | (CH2)2—NH-(1-(pyrimidin-2-yl)-piperidin-4-yl) |
| 174. | CH | Me | H | 2,6-diCl-4-OMe—Ph | (CH2)2—NH—(CH2)2—(3-OMe-4-EtO—Ph) |

TABLE 10

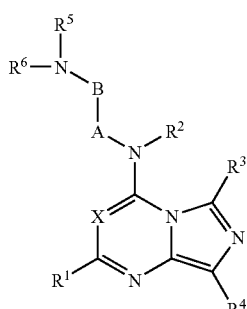

| EX | X | R1 | R2 | R3 | R4 |
|---|---|---|---|---|---|
| 175. | CH | Me | H | Me | 2,4,6-triMe—Ph |
| 176. | CH | Me | H | Me | 2,4,6-triMe—Ph |
| 177. | CH | Me | H | Me | 2,4,6-triMe—Ph |
| 178. | CH | Me | H | Me | 2,4,6-triMe—Ph |
| 179. | CH | Me | H | Me | 2,4,6-triMe—Ph |
| 180. | CH | Me | H | Me | 2,4,6-triMe—Ph |

TABLE 11

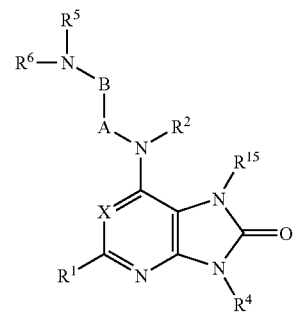

| EX | X | R1 | R2 | R15 |
|---|---|---|---|---|
| 181. | CH | CH | H | Me |
| 182. | CH | CH | H | Me |
| 183. | CH | CH | H | Me |
| 184. | CH | CH | H | Me |
| 185. | CH | CH | H | Me |
| 186. | N | CH | H | Me |
| 187. | N | CH | H | Me |
| 188. | N | CH | H | Me |
| 189. | N | CH | H | Me |
| 190. | N | CH | H | Me |
| 191. | N | CH | H | Me |

TABLE 12

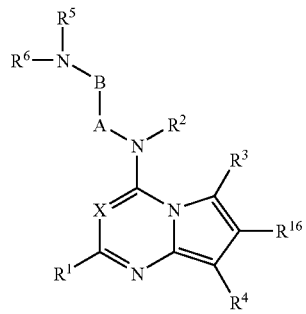

| EX | X | R1 | R2 | R3 | R16 | R4 | A—B—N[R⁶]—R⁵ |
|---|---|---|---|---|---|---|---|
| 192. | CH | Me | H | Me | H | 2,4,6-triMe—Ph | (CH2)2—NH-cPent |
| 193. | CH | Me | H | Me | H | 2,4,6-triMe-Ph | (CH2)2—NH-cHex |
| 194. | CH | Me | H | Me | H | 2,4,6-triMe-Ph | (CH2)2—NH-(4-OH-cHex) |
| 195. | CH | Me | H | Me | H | 2,4,6-triMe-Ph | (CH2)2—NH-(tetrahydropyran-4-yl) |
| 196. | CH | Me | H | Me | H | 2,4,6-triMe-Ph | (CH2)2—NH-(1-(pyrimidin-2-yl)-piperidin-4-yl) |
| 197. | CH | Me | H | Me | H | 2,6-diCl-4-OMe—Ph | (CH2)2—NH-cPent |
| 198. | CH | Me | H | Me | H | 2,6-diCl-4-OMe—Ph | (CH2)2—NH-cHex |
| 199. | CH | Me | H | Me | H | 2,6-diCl-4-OMe—Ph | (CH2)2—NH-(4-OH-cHex) |
| 200. | CH | Me | H | Me | H | 2,6-diCl-4-OMe—Ph | (CH2)2—NH-(tetrahydropyran-4-yl) |
| 201. | CH | Me | H | Me | H | 2,6-diCl-4-OMe—Ph | (CH2)2—NH-(1-(pyrimidin-2-yl)-piperidin-4-yl) |
| 202. | N | Me | H | Me | Me | 2,4,6-triMe—Ph | (CH2)2—NH—(CH2)2-(4-OMe—Ph) |
| 203. | N | Me | H | Me | H | 2,4,6-triMe—Ph | (CH2)2-NH-cPent |
| 204. | N | Me | H | Me | Me | 2,4,6-triMe-Ph | (CH2)2-NH-cPent |
| 205. | N | Me | H | Me | H | 2,4,6-triMe-Ph | (CH2)2-NH-Et |
| 206. | N | Me | H | Me | H | 2,4,6-triMe-Ph | (CH2)2-NH-(1-(pyrimidin-2-yl)-piperidin-4-yl) |
| 207. | N | Me | H | Me | Me | 2,4,6-triMe-Ph | (CH2)2—NH—(CH2)2-(3-OMe-4-EtO—Ph) |

TABLE 13

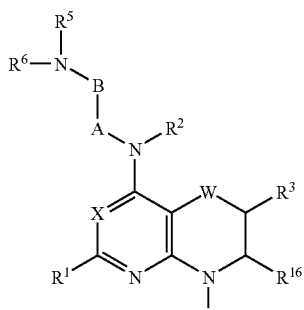

| EX | X | W | R1 | R2 | R3 | R16 | R4 |
|---|---|---|---|---|---|---|---|
| 208. | CH | NH | Me | H | Me | H | 2,4,6-triMe—Ph |
| 209. | CH | NH | Me | H | Me | H | 2,4,6-triMe—Ph |
| 210. | CH | NH | Me | H | Me | H | 2,4,6-triMe—Ph |
| 211. | CH | NH | Me | H | Me | H | 2,4,6-triMe—Ph |
| 212. | CH | NH | Me | H | Me | H | 2,4,6-triMe—Ph |
| 213. | CH | NH | Me | H | Me | H | 2,4,6-triMe—Ph |
| 214. | CH | NH | Me | H | Me | H | 2,6-diCl-4-OMe—Ph |
| 215. | CH | NH | Me | H | Me | H | 2,6-diCl-4-OMe—Ph |
| 216. | CH | NH | Me | H | Me | H | 2,6-diCl-4-OMe—Ph |
| 217. | CH | NH | Me | H | Me | H | 2,6-diCl-4-OMe—Ph |
| 218. | CH | NH | Me | H | Me | H | 2,6-diCl-4-OMe—Ph |
| 219. | N | NH | Me | H | Me | H | 2,4,6-triMe—Ph |
| 220. | N | NH | Me | H | Me | H | 2,4,6-triMe—Ph |
| 221. | N | NH | Me | H | Me | H | 2,4,6-triMe—Ph |
| 222. | N | NH | Me | H | Me | H | 2,4,6-triMe—Ph |
| 223. | N | NH | Me | H | Me | H | 2,4,6-triMe—Ph |
| 224. | N | NH | Me | H | Me | H | 2,4,6-triMe—Ph |

TABLE 14

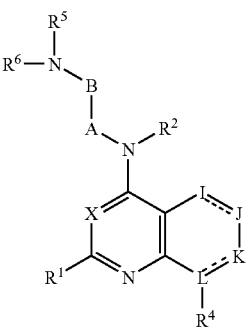

| EX | X | R1 | R2 | I | J | K |
|---|---|---|---|---|---|---|
| 225. | CH | Me | H | CH | CH | CH |
| 226. | CH | Me | H | CH | CH | CH |
| 227. | CH | Me | H | CH | CH | CH |
| 228. | CH | Me | H | CH | CH | CH |
| 229. | CH | Me | H | CH | CH | CH |
| 230. | CH | Me | H | CH | CH | CH |
| 231. | CH | Me | H | CH | CH | CH |

TABLE 15

$$\begin{array}{c} R^5 \\ | \\ R^6-N \\ | \\ B \\ | \\ A \quad R^2 \\ \backslash / \\ N \\ | \\ \text{[pyrimidine ring with X, Y, R}^1\text{, Q-R}^4\text{]} \end{array}$$

| EX | X | Y | R1 | R2 | Q | R4 | A—B—N[R⁶]—R⁵ |
|---|---|---|---|---|---|---|---|
| 232. | CH | CMe | Me | H | O | 2,4,6-triMe—Ph | (CH2)2—NcPent-(tetrahydropyran-4-yl) |
| 233. | CH | CMe | Me | H | O | 2,4,6-triMe—Ph | (CH2)2—NH-(1-(pyrimidin-2-yl)-piperidin-4-yl) |
| 234. | CH | CMe | Me | H | O | 2,4,6-triMe—Ph | (CH2)2—NH-cPent |
| 235. | CH | CMe | Me | H | O | 2,4,6-triMe—Ph | (CH2)3—NH-(1-Ac-piperidin-4-yl) |
| 236. | CH | CMe | Me | H | O | 2,4,6-triMe—Ph | (CH2)3—NH-(1,2,3,4-tetrahydro-naphthalen-2-yl) |
| 237. | CH | CMe | Me | H | O | 2,4,6-triMe—Ph | (CH2)4—NH-(1-(pyrimidin-2-yl)-piperidin-4-yl) |
| 238. | CH | CMe | Me | H | O | 2,4,6-triMe—Ph | (CH2)4—NH-(1-Ac-piperidin-4-yl) |
| 239. | CH | CMe | Me | H | O | 2,4,6-triMe—Ph | (CH2)4—NH-(1,2,3,4-tetrahydro-naphthalen-2-yl) |
| 240. | CH | CMe | Me | H | O | 2,4,6-triMe—Ph | CH2—CHMe—NH-(1-(pyrimidin-2-yl)-piperidin-4-yl) |
| 241. | CH | CMe | Me | H | O | 2,4,6-triMe—Ph | (CH2)2—NH-cHex |
| 242. | CH | CMe | Me | H | O | 2,4,6-triMe—Ph | (CH2)2—NH-(4-OH-cHex) |
| 243. | CH | CMe | Me | H | O | 2,4,6-triMe—Ph | (CH2)2—NH-(tetrahydropyran-4-yl) |
| 244. | N | CH | Me | H | NH | 2,4,6-triMe—Ph | (CH2)2—NH-cPent |
| 245. | N | CH | Me | H | NH | 2,4,6-triMe—Ph | (CH2)2—NH-cHex |
| 246. | N | CH | Me | H | NH | 2,4,6-triMe—Ph | (CH2)2—NH-(4-OH-cHex) |
| 247. | N | CH | Me | H | NH | 2,4,6-triMe—Ph | (CH2)2—NH-(tetrahydropyran-4-yl) |
| 248. | N | CH | Me | H | NH | 2,4,6-triMe—Ph | (CH2)2—NH-(1-(pyrimidin-2-yl)-piperidin-4-yl) |
| 249. | CH | N | Me | H | NEt | 2,4,6-triMe—Ph | (CH2)2—NH-cPent |
| 250. | CH | N | Me | H | NEt | 2,4,6-triMe—Ph | (CH2)2—NH-cHex |
| 251. | CH | N | Me | H | NEt | 2,4,6-triMe—Ph | (CH2)2—NH-(4-OH-cHex) |
| 252. | CH | N | Me | H | NEt | 2,4,6-triMe—Ph | (CH2)2—NH-(tetrahydropyran-4-yl) |
| 253. | CH | N | Me | H | NEt | 2,4,6-triMe—Ph | (CH2)2—NH-(1-(pyrimidin-2-yl)-piperidin-4-yl) |
| 254. | CH | N | Me | H | NEt | 2,4,6-triMe—Ph | (CH2)2—NH—(CH2)2-(3-OMe-4-EtO—Ph) |
| 255. | N | N | Me | H | NEt | 2,4,6-triMe—Ph | (CH2)2—NH-cPent |
| 256. | N | N | Me | H | NEt | 2,4,6-triMe—Ph | (CH2)2—NH-cHex |
| 257. | N | N | Me | H | NEt | 2,4,6-triMe—Ph | (CH2)2—NH-(4-OH-cHex) |
| 258. | N | N | Me | H | NEt | 2,4,6-triMe—Ph | (CH2)2—NH-(tetrahydropyran-4-yl) |
| 259. | N | N | Me | H | NEt | 2,4,6-triMe—Ph | (CH2)2—NH-(1-(pyrimidin-2-yl)-piperidin-4-yl) |
| 260. | N | N | Me | H | NEt | 2,4,6-triMe—Ph | (CH2)2—NH—(CH2)2-(3-OMe-4-EtO—Ph) |

Example 261

Characterization of NPY Receptor Interactions and In Vivo Function

A. Assay for Human $NPY_1$ Receptor Binding Activity: Compounds are assayed for activity using the following method: A cDNA encoding human NPY1 (SEQ ID NO:1) is ligated in the appropriate orientation for expression into the commercial expression vector pBacPAK9 (Clontech, Palo Alto, Calif.) for expression in SF9 cells. Each Baculoviral expression vector is co-transfected along with BACUL-OGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing $2 \times 10^6$ Sf9 cells in 5 mL of insect medium. After five days of incubation at 27° C., supernatant medium is harvested from each of the T25 infections for use as passage 1 inoculum. Recombinant baculoviral clones are then subjected to a second round of amplification, using 1 ml of passage 1 stock to infect $1 \times 10^8$ cells in 100 ml of insect medium divided into 2 T175 flasks. Forty-eight h post infection, passage 2 medium is harvested from each 100 ml prep and plaque assayed for titer. The cell pellets from the second round of amplification are assayed for affinity binding of radiolabeled ligand (see below) to verify recombinant receptor expression. A third round of amplification is then initiated using an M.O.I. of 0.1 to infect a liter of Sf9 cells. Forty h post-infection the supernatant medium is harvested to yield passage 3 baculoviral stock and the cell pellet assayed for affinity binding. Titer of the passage 3 baculoviral stock is determined by plaque assay and an M.O.I. and Incubation Time Course experiment is carried out to determine conditions for optimal receptor expression.

Log-phase Sf9 cells are infected with stocks of recombinant baculovirus encoding the proteins of interest (e.g., human NPY1 and three g-proteins), followed by culturing in insect medium at 27° C. 72 h post-infection, a sample of cell suspension is analyzed for viability by trypan blue dye exclusion, and the remaining Sf9 cells are harvested via centrifugation (3000 rpm/10 minutes/4° C.).

B. Preparation of purified membranes: Sf9 cell pellets are resuspended in homogenization buffer (10 mM HEPES, 250 mM sucrose, 0.5 □g/ml leupeptin, 2 □g/ml Aprotinin, 200 □M PMSF, and 2.5 mM EDTA, pH 7.4) and homogenized using a POLYTRON homogenizer (setting 5 for 30 seconds). The homogenate is centrifuged (536×g/10 minutes/4° C.) to pellet the nuclei. The supernatant containing isolated membranes is decanted to a clean centrifuge tube, centrifuged (48,000×g/30 minutes, 4° C.) and resuspended in 30 ml, or preferably 20 ml of homogenization buffer. This centrifugation and resuspension step is repeated twice. The final pellet is resuspended in ice cold Dulbecco's PBS containing 5 mM EDTA and stored in frozen aliquots until needed at −80° C. The protein concentration of the resulting membrane preparation is measured using the Bradford protein assay (Bio-Rad Laboratories, Hercules, Calif.). By this measure, a 1-liter culture of cells typically yields 50–100 mg of total membrane protein.

CO-infection for GTP$\gamma^{35}$S binding assay: Four baculoviral expression vector stocks are used to infect a culture of Sf9 cells with an MOI of 1:1:1:1. These four consisted of one vector encoding the human NPY1 receptor and a different commercially obtained baculoviral expression vector stock encoding each of the three subunits of a heterotrimeric G-protein, in particular, the G-protein-encoding virus stocks are obtained from BIOSIGNAL Inc., Montreal, and are 1) a G$\alpha$ G-protein subunit-encoding virus stock (either the rat G$\alpha_{i2}$ G-protein-encoding virus stock BIOSIGNAL #V5J008 or the rat G$\alpha_o$ G-protein-encoding virus stock BIOSIGNAL #V5H010), 2) a bovine β1 G-protein-encoding virus stock (BIOSIGNAL #V5H012), and 3) a human γ2 G-protein-encoding virus stock (BIOSIGNAL #V6B003). Agonist-stimulated GTP$\gamma^{35}$S binding on purified membranes is assessed using hNPY 1–36 (American Peptide Co., Sunnyvale, Calif.) as agonist in order to ascertain functional activity as measured by GTP$\gamma^{35}$S binding.

GTP$\gamma^{35}$S binding assay: Purified Sf9 cell membranes are resuspended by Dounce homogenization (tight pestle) in GTP$\gamma^{35}$S binding assay buffer (50 mM Tris pH 7.0, 120 mM NaCl, 2 mM MgCl2, 2 mM EGTA, 0.1% BSA, 0.1 mM bacitracin, 100 KIU/mL Aprotinin, 5 μM GDP) and added to reaction tubes at a concentration of 30 μg/reaction tube. After adding increasing doses of the agonist hNPY 1–36 (American Peptide Co., Sunnyvale, Calif.), reactions are initiated by the addition of 100 pM GTP$\gamma^{35}$S. Following a 30-minute incubation at ambient temperature, the reactions are terminated by vacuum filtration over GF/C filters (presoaked in wash buffer, 0.1% BSA) followed by washing with ice-cold wash buffer (50 mM Tris pH 7.0, 120 mM NaCl).

Bound GTP$\gamma^{35}$S is determined by liquid scintillation spectrometry of the washed filters. Nonspecific binding is determined using 10 mM GTPγS. Data are generally expressed as % maximal response and are derived by determining the maximal agonist stimulated % above basal stimulation. Computer analysis may be conveniently used to calculate estimated $EC_{50}$, $IC_{50}$ and $K_i$ values from GTP$\gamma^{35}$S binding experiment data, e.g., using SigmaPlot software. The binding affinity for the preferred compounds of the invention, expressed as $K_i$ values, ranges from about 0.1 nanomolar to about 5 micromolar. Particularly preferred compounds yield a $K_i$ value of less than 100 nanomolar, most preferably less than 10 nanomolar.

Assay for affinity binding of radiolabeled ligand: Purified membranes are washed with PBS and re-suspended by gentle pipetting in binding buffer (50 mM Tris(HCl), 5 mM KCl, 120 mM NaCl, 2 mM CaCl2, 1 mM MgCl2, 0.1% bovine serum albumin (BSA), pH 7.4). Membranes (5 μg) are added to siliconized (Sigmacote, Sigma) polypropylene tubes in addition to 0.050 nM [125I]NPY (porcine, New England Nuclear Corp., Boston, Mass.) for competition analysis or 0.010–0.500 nM [125I]NPY (porcine) for saturation analysis. For evaluation of guanine nucleotide effects on receptor affinity, GTP is added at a final concentration of 100 μM. Cold displacers are added at concentrations ranging from 10−12 M to 10−6 M to yield a final volume of 0.250 mL. Nonspecific binding is determined in the presence of 1 μM NPY (human, American Peptide Co., Sunnyvale, Calif.) and accounts for less than 10% of total binding. Following a 2-hour incubation at ambient temperature, the reaction is terminated by rapid vacuum filtration. Samples are filtered over presoaked GF/C Whatman filters (1.0% polyethyleneimine for 2 hours) and rinsed 2 times with 5 mL cold binding buffer lacking BSA. Remaining bound radioactivity is measured by gamma counting. To estimate the Bmax, Kd and Ki, the results of binding experiments are analyzed using SigmaPlot software (SPSS Science, Chicago, Ill.). The binding affinity for the compounds of the invention, expressed as a Ki value, ranges from about 0.1 nanomolar to about 10 micromolar. The most preferred compounds of the invention have a Ki of less than 100 nanomolar and a binding selectivity of >100-fold relative to other G-protein coupled receptors, including $NPY_5$ and $CRF_1$ receptors.

C. In Vivo Analysis—Food Deprivation

Subjects. Experimentally naive and experienced male Sprague-Dawley rats (Sasco, St. Louis, Mo.) weighing 210–300 g at the beginning of the experiment are used. Animals are triple-housed in stainless steel hanging cages in a temperature (22 C±2) and humidity (40–70% RH) controlled animal facility with a 12:12 hour light-dark cycle. Food (Standard Rat Chow, PMI Feeds Inc., #5012) and water are available ad libitum.

Apparatus. Consumption data is collected while the animals are housed in Nalgene Metabolic cages (Model #650–0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment.

The second assembly includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, and body weight may be measured with an Ohaus Portable Advanced scale (±0.1 g accuracy).

Procedure. Prior to the day of testing, animals are habituated to the testing apparatus by placing each animal in a Metabolic cage for 1 hour. On the, day of the experiment, animals that have been food deprived the previous night are weighed and assigned to treatment groups. Assignments are made using a quasi-random method utilizing the body weights to assure that the treatment groups had similar average body weight. Animals are then administered either vehicle (0.5% methyl cellulose) or drug (a compound of the invention). At that time, the feeding drawer is filled with pulverized chow, the filled water bottle, and the empty urine and feces collection tubes are weighed. Two h after drug treatment, each animal is weighed and placed in a Metabolic Cage. Following a one-hour test session, animals are removed and body weight obtained. The food and water containers are then weighed and the food and water consumption data recorded.

Drugs. Drug suspended in vehicle, or vehicle alone as a control, is administered orally (PO) using a gavage tube connected to a 3 or 5 ml syringe at a volume of 10 ml/kg. Drug is made into a homogenous suspension by stirring and ultrasonicating for at least 1 hour prior to dosing.

Statistical Analyses. The means and standard errors of the mean (SEM) for food consumption, water consumption, and body weight change are obtained. One-way analysis of variance using Systat (5.2.1) is used to test for group differences. A significant effect is defined as having a p value of <0.05.

The following parameters are defined: Body weight change is the difference between the body weight of the animal immediately prior to placement in the metabolic cage and its body weight at the end of the one hour test session. Food consumption is the difference in the weight of the food drawer prior to testing and the weight following the 1-hour test session. Water consumption is the difference in the weight of the water bottle prior to testing and the weight following the 1-hour test session. Preferred compounds of the invention reduce food intake and body weight gain, preferably to a statistically significant degree as determined by standard parametric analysis such as a student's T-test.

Example 262

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 263

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound selected from Formulae II, IV, V, VII–IX and XI

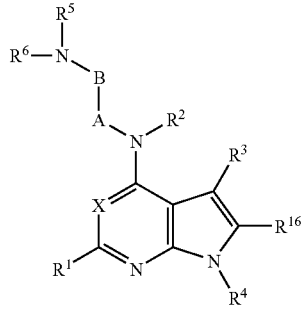

II

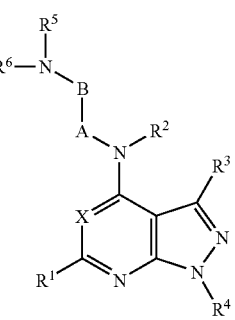

IV

-continued

V
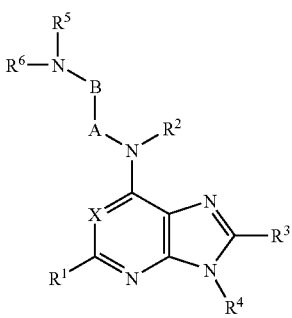

VII
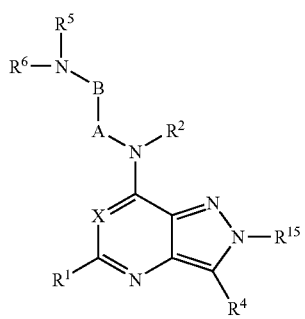

VIII
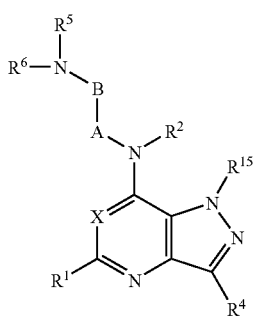

IX
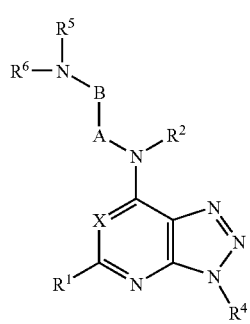

XI
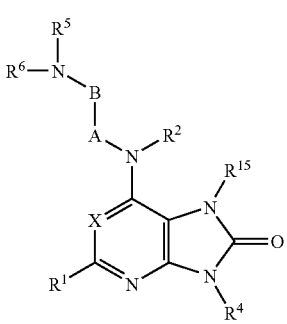

or a pharmaceutically acceptable salt thereof, wherein
X is C (carbon);
$R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$;

$R^2$ is H,
$C_1$–$C_6$ alkyl which optionally forms a $C_3$–$C_6$ aminocarbocycle or a $C_2$–$C_5$ aminoheterocycle with A or B, each optionally substituted at each occurrence with $R^7$, $C_3$–$C_{10}$ cycloalkyl, or
($C_3$–$C_{10}$ cycloalkyl) $C_1$–$C_6$ alkyl;
or $R^2$ and $R^6$ jointly form with the 2 nitrogen atoms to which they are bound a $C_2$–$C_5$ aminoheterocycle optionally substituted at each position with $R^7$;

A is $(CH_2)_m$ where m is 1, 2 or 3 and is optionally mono- or di-substituted on each occurrence with $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$, or
A and B jointly form a $C_3$–$C_6$ carbocycle, optionally substituted at each position with $R^7$ or,
A and $R^2$ jointly form a $C_3$–$C_6$ aminocarbocycle or a $C_2$–$C_5$ aminoheterocycle optionally substituted at each position with $R^7$;

B is $(CH_2)_n$ where n is 1, 2 or 3 and is optionally mono- or di-substituted on each carbon atom with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$, or
B and $R^2$ jointly form a $C_3$–$C_6$ aminocarbocycle or a $C_2$–$C_5$ aminoheterocycle optionally substituted at each carbon occurrence with $R^7$;

$R^3$ and $R^{16}$ are independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halogen, $C_1$–$C_6$ haloalkyl, $OR^7$, $C_1$–$C_6$ alkyl-$OR^7$, $C_1$–$C_6$ cyanoalkyl, $NR^8R^9$, $C_1$–$C_6$ alkyl-$NR^8R^9$;

$R^4$ is selected from aryl or heteroaryl, each optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), with the proviso that at least one of the positions ortho or para to the point of attachment of the aryl or heteroaryl ring to the heterocyclic core is substituted;

$R^5$ is selected from:
$C_1$–$C_6$ alkyl, ($C_3$–$C_{10}$ cycloalkyl) $C_1$–$C_6$ alkyl, $C_2$–$C_6$ alkenyl, $C_2$–$C_6$ alkynyl, each of which is substituted with 1 to 5 groups independently selected at each occurrence from halo, $C_1$–$C_2$ haloalkyl, $OR^7$, cyano, $NR^8R^9$, $CONR^8R^9$, $COOR^7$, $SO_2NR^8R^9$, $SO_2R^7$, $NR^{11}COR^{12}$, $NR^{11}SO_2R^7$;

$C_1$–$C_6$ arylalkyl, $C_1$–$C_6$ heteroarylalkyl, $C_5$–$C_8$ arylcycloalkyl, or $C_5$–$C_8$ heteroarylcycloalkyl, where aryl is phenyl or naphthyl, and heteroaryl is 2-,3-, or 4-pyridyl, 2-, 4- or 5-pyrimidinyl, triazinyl, 1-, 2- or 4-imidazolyl, 2-, 4-, or 5-oxazolyl, isoxazolyl, indolyl, pyrazolyl, quinolyl, isoquinolyl, 2-, 4-, or 5-thiazolyl, benzothiadiazolyl, 1-, 3- or 4-pyrazolyl, 1-, 3- or 4-triazolyl, 2-triazinyl, 2-pyrazinyl, 2-, or 3-furanyl, 2-, or 3-thienyl, 2-, or 3-benzothienyl, or 1-, 2- or 5-tetrazolyl, each of which is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein 2 adjacent alkyl substituents can optionally form together a $C_3$–$C_{10}$ cycloalkyl ring, a $C_3$–$C_{10}$ cycloalkenyl ring or a heterocycloalkyl ring; $C_3$–$C_{10}$ cycloalkyl, ($C_3$–$C_{10}$ cycloalkyl) $C_1$–$C_6$ alkyl, $C_3$–$C_{10}$ cycloalkenyl, $C_2$–$C_6$ alkenyl, $C_2$–$C_6$ alkynyl, each of which is optionally with 1 to 6 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, with the proviso that when two $OR^7$ or $NR^8R^9$ substituents are geminally located on the same carbon $R^7$ is not H and they can form together a $C_2$–$C_4$ ketal, oxazoline, oxazolidine, imidazoline, or imidazolidine heterocycle, $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein 2 adjacent alkyl substituents can optionally form together a $C_3$–$C_{10}$ cycloalkyl ring, $C_3$–$C_{10}$ cycloalkenyl ring or a heterocycloalkyl ring; aryl or heteroaryl, optionally substituted with 1 to 5 substituents independently selected at each occurrence from halogen, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein 2 adjacent alkyl substituents can optionally form together a $C_3$–$C_{10}$ cycloalkyl ring, a $C_3$–$C_{10}$ cycloalkenyl ring or a heterocycloalkyl ring; or 3- or 4-piperidinyl, 3-pyrrolidinyl, 3- or 4-tetrahydropyranyl, 3-tetrahydrofuranyl, 3- or 4-tetrahydropyranyl, 3-tetrahydrofuranyl, 3- or 4-tetrahydrothiopyranyl, 3- or 4-(1,1-dioxo)tetrahydrothiopyranyl, 1-azabicyclo[4.4.0]decyl, 8-azabicyclo[3.2.1]octanyl, norbornyl, quinuclidinyl, each optionally substituted with 1 to 5 substituents independently selected at each occurrence from $R_7$, $C_1$–$C_6$ alkyl-$OR^7$, $C_1$–$C_6$ alkyl-$NR^8R^9$, $CONR^8R^9$, $COOR^7$;

$R^6$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_1$–$C_6$ arylalkyl, $C_1$–$C_6$ heteroarylalkyl where aryl or heteroaryl are optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^7$, CN, $SO_2NR^8R^9$, $SO_2R^7$, or $R^6$ and $R^2$, as mentioned above, jointly form, with the 2 nitrogen atoms to which they are bound, a $C_2$–$C_5$ aminoheterocycle optionally substituted at each position with $R^7$;

$R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that when $R^7$ is $SO_2R^{13}$, $R^{13}$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that for $SO_2NR^8R^9$, $SO_2R^{13}$, $R^{13}$ cannot be H; and $R^{15}$ is selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_2$–$C_6$ alkyl-$OR^7$, $C_2$–$C_6$ cyanoalkyl, $C_2$–$C_6$ alkyl-$NR^8R^9$.

* * * * *

SEQUENCE LISTING

```
<160> NUMBER OF SEQ ID NOS: 1

<210> SEQ ID NO 1
<211> LENGTH: 1605
<212> TYPE: DNA
<213> ORGANISM: Homo sapiens

<400> SEQUENCE: 1
ccttctttaa tgaagcagga gcgaaaaaga caaattccaa agaggattgt tcagttcaag      60
ggaatgaaga attcagaata attttggtaa atggattcca atatggggaa taagaataag     120
```

-continued

```
ctgaacagtt gacctgcttt gaagaaacat actgtccatt tgtctaaaat aatctataac    180
aaccaaacca atcaaaatga attcaacatt attttcccag gttgaaaatc attcagtcca    240
ctctaatttc tcagagaaga atgcccagct tctggctttt gaaaatgatg attgtcatct    300
gcccttggcc atgatattta ccttagctct tgcttatgga gctgtgatca ttcttggtgt    360
ctctggaaac ctggccttga tcataatcat cttgaaacaa aaggagatga gaaatgttac    420
caacatcctg attgtgaacc tttccttctc agacttgctt gttgccatca tgtgtctccc    480
ctttacattt gtctacacat taatggacca ctgggtcttt ggtgaggcga tgtgtaagtt    540
gaatcctttt gtgcaatgtg tttcaatcac tgtgtccatt ttctctctgg ttctcattgc    600
tgtggaacga catcagctga taatcaaccc tcgagggtgg agaccaaata atagacatgc    660
ttatgtaggt attgctgtga tttgggtcct tgctgtggct tcttctttgc ctttcctgat    720
ctaccaagta atgactgatg agccgttcca aaatgtaaca cttgatgcgt acaaagacaa    780
atacgtgtgc tttgatcaat ttccatcgga ctctcatagg ttgtcttata ccactctcct    840
cttggtgctg cagtattttg gtccactttg ttttatattt atttgctact tcaagatata    900
tatacgccta aaaaggagaa acaacatgat ggacaagatg agagacaata agtacaggtc    960
cagtgaaacc aaaagaatca atatcatgct gctctccatt gtggtagcat ttgcagtctg   1020
ctggctccct cttaccatct ttaacactgt gtttgattgg aatcatcaga tcattgctac   1080
ctgcaaccac aatctgttat tcctgctctg ccacctcaca gcaatgatat ccacttgtgt   1140
caacccccata ttttatgggt tcctgaacaa aaacttccag agagacttgc agttcttctt   1200
caactttgt gatttccggt ctcgggatga tgattatgaa acaatagcca tgtccacgat   1260
gcacacagat gtttccaaaa cttctttgaa gcaagcaagc ccagtcgcat ttaaaaaaat   1320
caacaacaat gatgataatg aaaaaatctg aaactactta tagcctatgg tcccggatga   1380
catctgttta aaaacaagca caacctgcaa catactttga ttacctgttc tcccaaggaa   1440
tggggttgaa atcatttgaa aatgactaag attttcttgt cttgcttttt actgcttttg   1500
ttgtagttgt cataattaca tttgaacaa aaggtgtggg cttgggtc ttctggaaat    1560
agttttgacc agacatcttt gaagtgcttt ttgtgaattt accag                  1605
```